(12) United States Patent
Mangano et al.

(10) Patent No.: US 7,572,623 B2
(45) Date of Patent: Aug. 11, 2009

(54) CELL SEPARATION USING ELECTRIC FIELDS

(76) Inventors: Joseph Mangano, 1530 N. Key Blvd., Arlington, VA (US) 22209; Henry Eppich, 47 Wildrose Dr., Andover, MA (US) 01810

(*) Notice: Subject to any disclaimer, the term of this patent is extended or adjusted under 35 U.S.C. 154(b) by 274 days.

(21) Appl. No.: 10/422,310

(22) Filed: Apr. 23, 2003

(65) Prior Publication Data

US 2003/0199050 A1 Oct. 23, 2003

Related U.S. Application Data

(62) Division of application No. 09/489,116, filed on Jan. 21, 2000, now Pat. No. 6,589,786, which is a division of application No. 09/148,620, filed on Sep. 4, 1998, now Pat. No. 6,043,066.

(60) Provisional application No. 60/057,809, filed on Sep. 4, 1997.

(51) Int. Cl.
*C12M 1/42* (2006.01)
*C12N 13/00* (2006.01)
*C12N 15/87* (2006.01)

(52) U.S. Cl. .............. 435/285.2; 435/173.1; 435/173.4; 435/173.5; 435/173.8; 435/287.2; 435/288.3; 435/288.4; 435/461; 435/470; 435/173.6; 264/81; 264/105; 427/122; 427/249.6

(58) Field of Classification Search .............. 435/173.6, 435/173.1, 173.4, 173.5, 173.8, 285.2, 287.2, 435/288.3, 288.4, 461, 470; 264/81, 105; 427/122, 249.6

See application file for complete search history.

(56) References Cited

U.S. PATENT DOCUMENTS 4,714,680 A 12/1987 Civin

2003/0119080 A1 6/2003 Mangano (Continued)

FOREIGN PATENT DOCUMENTS

WO 99/54439 A1 10/1999

OTHER PUBLICATIONS

Supplementary Partial European Search Report dated Feb. 22, 2005 for corresponding European Patent Application No. EP 98948084 and the claims as pending for corresponding European Patent Application No. EP 98948084.

(Continued)

*Primary Examiner*—William H Beisner
*Assistant Examiner*—Nathan A Bowers
(74) *Attorney, Agent, or Firm*—Wolf, Greenfield & Sacks, P.C.

(57) ABSTRACT

The present invention involves methods and devices which enable discrete objects having a conducting inner core, surrounded by a dielectric membrane to be selectively inactivated by electric fields via irreversible breakdown of their dielectric membrane. One important application of the invention is in the selection, purification, and/or purging of desired or undesired biological cells from cell suspensions. According to the invention, electric fields can be utilized to selectively inactivate and render non-viable particular subpopulations of cells in a suspension, while not adversely affecting other desired subpopulations. According to the inventive methods, the cells can be selected on the basis of intrinsic or induced differences in a characteristic electroporation threshold, which can depend, for example, on a difference in cell size and/or critical dielectric membrane breakdown voltage. The invention enables effective cell separation without the need to employ undesirable exogenous agents, such as toxins or antibodies. The inventive method also enables relatively rapid cell separation involving a relatively low degree of trauma or modification to the selected, desired cells. The inventive method has a variety of potential applications in clinical medicine, research, etc., with two of the more important foreseeable applications being stem cell enrichment/isolation, and cancer cell purging.

20 Claims, 28 Drawing Sheets

E = 0

U.S. PATENT DOCUMENTS

| | | | |
|---|---|---|---|
| 4,822,470 A | | 4/1989 | Chang |
| 4,852,571 A | * | 8/1989 | Gadsby et al. .............. 600/396 |
| 4,923,814 A | * | 5/1990 | Marshall, III ............ 435/173.6 |
| 4,965,204 A | | 10/1990 | Civin |
| 5,035,994 A | | 7/1991 | Civin |
| 5,048,404 A | | 9/1991 | Bushnell et al. |
| 5,130,144 A | | 7/1992 | Civin |
| 5,147,590 A | * | 9/1992 | Preidel et al. ................. 264/81 |
| 5,173,158 A | * | 12/1992 | Schmukler .................. 435/450 |
| 5,235,905 A | * | 8/1993 | Bushnell et al. ............... 99/451 |
| 5,283,194 A | * | 2/1994 | Schmukler ............... 435/285.2 |
| 5,635,040 A | * | 6/1997 | Bakhir et al. ............... 204/260 |
| 5,744,347 A | | 4/1998 | Wagner et al. |
| 5,750,397 A | | 5/1998 | Tsukamoto et al. |
| 5,824,857 A | * | 10/1998 | Beachy et al. ............... 800/287 |
| 5,873,849 A | * | 2/1999 | Bernard ....................... 604/20 |
| 6,617,154 B1 | * | 9/2003 | Meserol ................... 435/285.2 |

OTHER PUBLICATIONS

Eppich, H. et al. "Pulsed electric fields function to size-select hematopoietic cells and deplete tumor cell contaminants," *Abstracts for the Thirty-Ninth Annual Meeting of the American Society of Hematology Dec. 5-9, 1997*, Abstract No. 4326.

Eppich, H. et al. "Pulsed electric fields for size-selection of hematopoietic cells and depletion of tumor cell contaminants," *Nature Biotechnology*, vol. 18, Aug. 2000, pp: 882-887.

Orlowski, S. et al. "Cell electropermeabilization: a new tool for biochemical and pharmacological studies," *Biochemica et Biophysica ACTA*, vol. 1154, No. 1, Jun. 8, 1993, pp: 51-63.

Audet, J. et al., "Advances in hematopoietic stem cell culture", *Current Opinion in Biotechnology*, 9:146-151, 1998.

Banchereau, J. et al., "Long-Term Human B Cell Lines Dependent on Interleukin-4 and Antibody to CD40", *Science*, vol. 251, pp. 70-72, Jan. 1991.

Berardi, A. et al., "Functional Isolation and Characterization of Human Hematopoietic Stem Cells", Science, vol. 267, pp. 104-108, Jan. 1995.

Berg, H.et al., "Electric Field Effects on Biological Membranes: Electroincorporation and Electrofusion," Ettore Majorana Int. Sci. Ser.: *Phys. Sci.*, vol. 32(Bioelectrochem. 2: Membr. Phenom.), pp. 135-166,1987.

Berger, S.L., "Lymphocytes as Resting Cells", Methods in Enzymology, Chapter entitled Specific Cell Lines, vol. LVIII, Sec. 42, pp. 486-494, 1979.

Castro, A.J. et al., "Microbial Inactivation of Foods by Pulsed Electric Fields", *J. of Food Processing and Preservation*, 1993, vol. 17, No. 1, p. 47.

Dey, S.B. and G.A. Hofmann, "Clinical Applications of Electroporation", Electrical Manipulation of Cells, P.T. Lynch and M.R. Davey editors, pp. 187-191, 1996.

Grahl, T. et al., "Killing of microorganisms in fluid media by high-voltage pulses", DECHEMA Biotechnology Conferences 5, pp. 675-678, 1992.

Graziadei, L. et al., "Introduction of Unlabeled Proteins into Living Cells by Electroporation and Isolation of Viable Protein-Loaded Cells Using Dextran-Fluorescein Isothiocyanate as a Marker for Protein Uptake," *Analytical Biochemistry*, vol. 194, pp. 198-203, 1991.

Hamilton, W.A. and A.J.H. Sale, "Effects of High Electric Fields on Microorganisms II. Mechamism of Action of the Lethal Effect", *Bichimica et Biophysica Acta*, BBA 25877, vol. 148, pp. 789-800, Jul. 1967.

Hofmann, G.H. and G.A.Evans, "Electronic Genetic-Physical and Biological Aspects of Cellular Electromanipulation," IEEE Engineering in Medicine and Biology Magazine, pp. 6-23, Dec. 1986.

Hülsheger, H. and E.G. Niemann, "Lethal Effects of High-Voltage Pulses on E. Coli K12", *Radiation and Environmental Biophysics*, vol. 18, pp. 281-288, 1980.

Hülsheger, H. et al., "Electric Field Effects on Bacteria and Yeast Cells", *Radiation and Environmental Biophysics*, vol. 22 pp. 149-162, 1983.

Hülsheger, H. et al., "Killing of Bacteria with Electric Pulses of High Field Strength", *Radiation and Environmental Biophysics*, vol. 20, pp. 53-65, 1981.

Kinosita K., Jr. and T.Y. Tsong, "Voltage-Induced Pore Formation and Hemolysis of Human Erythrocytes", *Biochimica et Biophysica Acta*, vol. 471, pp. 227-242, 1977.

Kinosita, K., Jr. and T.Y. Tsong, "Hemolysis of human erythrocytes by a transient electric field", *Proc. Natl. Acad. Sci.* USA, vol. 74, No. 5, pp. 1923-1927, May 1977.

Lechner, J.F. et al., "Normal Human Prostate Epithelial Cell Cultures", *Methods in Cell Biology*, vol. 21B, Chapter 9, pp. 195-225, 1980.

Mischke, S. et al., "A versatile low-cost apparatus for cell electrofusion and other Electrophysiological treatments," *Journal for Biochemical and Biophysical Methods*, vol. 13, pp. 65-75, 1986.

Sale, A.J.H. and W.A. Hamilton, "Effects of High Electric Fields on Microorganisms I. Killing of Bacteria and Yeasts", *Biochimica et Biophysica Acta*, BBA 25876, vol. 148, pp. 781-788, Jul. 1967.

Sale, A.J.H. and W.A. Hamilton, "Effects of High Electric Fields on Micro-Organisms III. Lysis of Erythrocytes and Protoplasts", *Biochimica et Biophysica Acta*, BBA 75160, vol. 163, pp. 37-43, 1968.

Sato, T. et al., "Establishment of a human leukaemic cell line(CMK) with megakaryocytic characteristics from a Down's syndrome patient with acute megakaryoblastic leukaemia",, *British Journal of Haematology*, vol. 72, pp. 184-190, 1989.

Schanne, O.F. and E.R.P.-Ceretti, Impedance Measurements in Biological Cells, Chapter 5.3, pp. 331-337, 1978.

Sixou, S. and J. Teissié, "Specific electropermeabilization of leucocytes in a blood sample and application to large volumes of cells", *Biochimica et Biophysica Acta*, BBAMEM 75004, vol. 1028, pp. 154-160, 1990.

Teissie J. and T.Y. Tsong, "Electric Field Induced Transient Pores in Phospholipid Bilayer Vesicles", *Biochemistry*, vol. 20, No. 6, pp. 1548-1554, 1981.

Tsong, T.Y., "Electrically Stimulated Membrane Breakdown", Electrical Manipulation of Cells, P.T. Lynch and M.R. Davey editors, Chapter 2, pp. 15-36, 1996.

Vallé, A. et al., "Activation of human B lymphocytes through CD40 and interleukin 4", *Eur.J.Immunol.*, vol. 19, pp. 1463-1467, 1989.

Zipori, D. and F. Lee, "Introduction of Interleukin-3 Gene Into Stromal Cells From the Bone Marrow Alters Hemopoietic Differentiation but Does not Modify Stem Cell Renewal", *Blood*, vol. 71, No. 3, pp. 586-596, Mar. 1988.

* cited by examiner

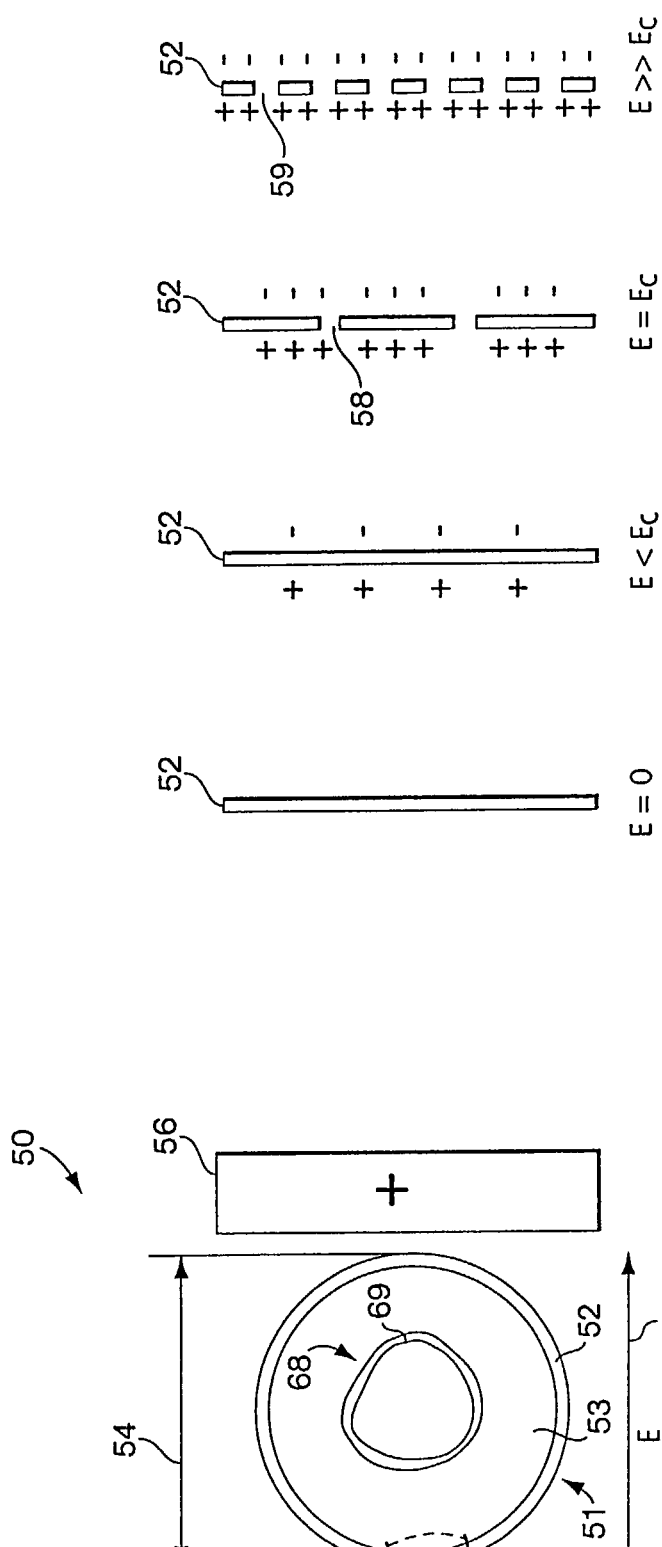

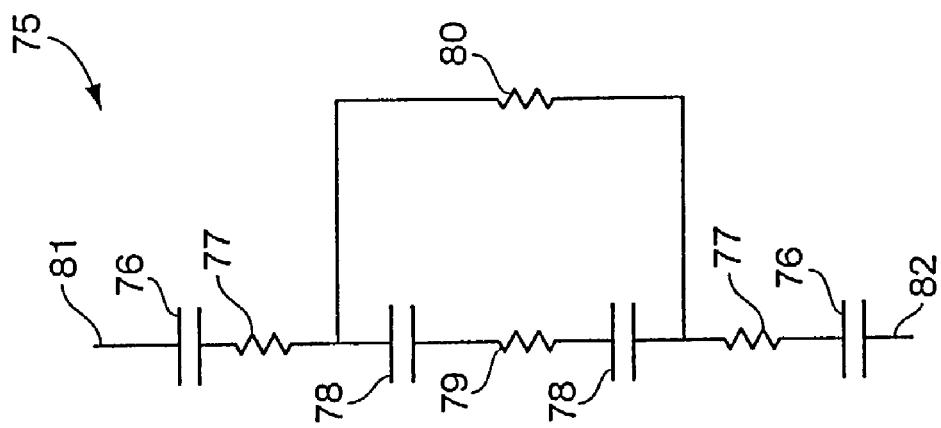
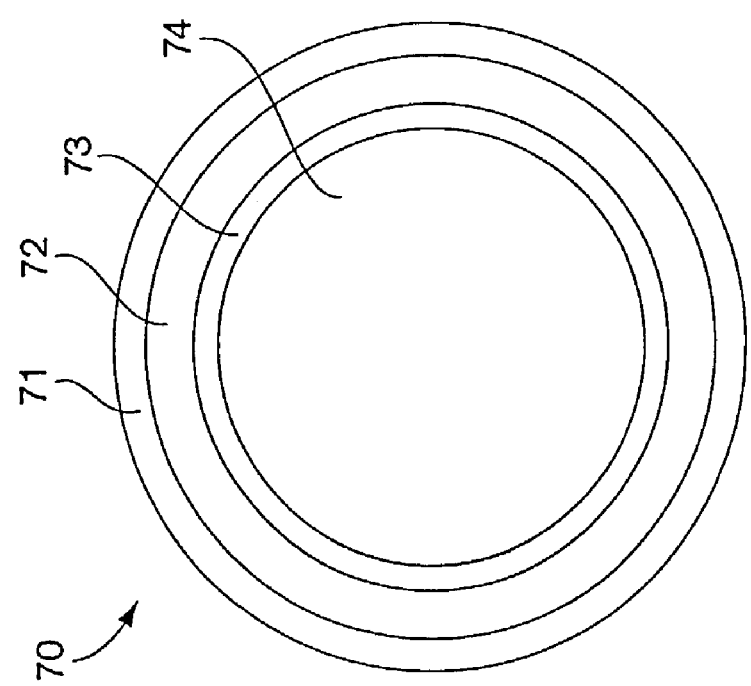
Fig. 2b
Fig. 2a

MONOCYTES        LYMPHOCYTES

CELL SEPARATION USING ELECTRIC FIELDS

RELATED APPLICATIONS

This application is a division of U.S. application Ser. No. 09/489,116, filed Jan. 21, 2000 and issued on Jul. 8, 2003 as U.S. Pat. No. 6,589,786, which is a division of U.S. application Ser. No. 09/148,620, filed Sep. 4, 1998 and issued on Mar. 28, 2000 as U.S. Pat. No. 6,043,066, which claims priority from provisional specification No. 60/057,809 filed Sep. 4, 1997, each of which is incorporated herein by reference.

STATEMENT REGARDING FEDERALLY SPONSORED RESEARCH OR DEVELOPMENT

The U.S. Government has a paid-up license in this invention and the right in limited circumstances to require the patent owner to licence others on reasonable terms as provided for by the terms of subcontract No. 04027 awarded the National Technology Transfer Center at Wheeling Jesuit University supported by the Ballistic Missile Defense Organization, Technology applications Program—NASA Cooperative Agreement no. NCC W-0065.

FIELD OF THE INVENTION

This invention relates to methods and apparatuses for selecting specific cell types from cell suspensions, specifically those employing applied electric fields.

BACKGROUND OF THE INVENTION

The ability to isolate specific sub-populations of cells from cell suspensions is of critical importance to many applications in the biological sciences as well as to many therapies in clinical medicine. For example, the basis of many medical therapies for treating a variety of human diseases and for countering the effects of a variety of physiological injuries involves the isolation, manipulation, expansion, and/or alteration of specific biological cells. One particularly important example involves the reconstitution of the hematopoietic system via bone marrow or progenitor cell transplantation. More specific examples include: autologous, syngeneic, and allogenic stem cell transplants for immune system reconstitution following the myeloablative effects of severe high dose chemotherapy or therapeutic irradiation; severe exposure to certain chemical agents; or severe exposure to environmental radiation, for example from nuclear weapons or accidents involving nuclear power generators.

Intensive chemotherapy and/or irradiation for the treatment of a variety of cancers, including breast cancer, has become a commonly used approach in cancer care centers. Such treatments are associated with severe ablation of the bone marrow cells required for function of the blood and immune systems. Such bone marrow cells are derived from a small number of progenitor cells known as hematopoietic stem cells in the normal bone marrow. Therefore, patients receiving such therapies require life-saving transplants of stem cells in order to survive the effects of the treatment. Stem cell containing tissue for transplant may be derived from donor marrow (allogeneic transplant) or from the patient's own bone marrow or peripheral blood after mobilization (autologous transplant). In both instances, there is a need for effective cell separation methods to enrich the transplant tissue in stem cells and reduce the number of undesirable and deleterious cells (e.g. mature T cells for allogeneic transplants and residual cancerous cells for autologous transplants). For example, for autologous adjuvant stem cell transplant therapy following myeloablative cancer treatments, it is believed that reinfusion of residual tumor cells is a major cause of post therapy relapse. Clearly, removing such cells from transplanted tissue would be beneficial to the patient.

A number of cell isolation, cell separation, and cell purging strategies have been employed in the prior art for purifying or removing cells from a suspension. Prior art cell separation methods used to isolate cells or purge cell suspensions typically fall into one of three broad categories: physical separation methods typically exploit differences in a physical property between cell types, such as cell size or density (e.g. centrifugation or elutriation); chemical-based methods typically employ an agent that selectively kills or purges one or more undesirable cell types; and affinity-based methods typically exploit antibodies that bind selectively to marker molecules on a cell membrane surface of desired or undesired cell types, which antibodies may subsequently enable the cells to be isolated or removed from the suspension. While physical separation methods can be advantageous with regard to their ability to separate cells without causing undo damage to desired cells, current physical separation methods typically have relatively poor specificity and do not typically yield highly purified or highly purged cell suspensions. While many chemical and affinity methods have better selectivity than typical physical methods, they can often be expensive or time consuming to perform and can cause considerable damage to, or activation of, desired cells, for example stem cells, and/or can add undesirable agents to the purified or isolated cell suspensions (e.g. toxins, proliferation-inducing agents, and/or antibodies). An additional potential problem with antibody-based cell separation techniques typically employed for purification of stem cells, is that they select stem cells solely on the basis of cell surface markers (e.g., CD34) and will not select cells lacking such markers.

In addition to cancer therapy, there are a number of other important medical therapies which exist, or are under development, that are based on cells derived from a variety of different types of stem cells. Examples include pre-exposure prophylaxis or post-exposure therapies under development for a variety of biological exposures that may occur naturally (e.g., viral exposure for example with Ebola, etc.) or be inflicted by mankind (i.e., biological warfare agents). A variety of gene therapies involving genetically manipulated stem cells, are being contemplated or are under development for treating a variety of blood-related diseases (e.g., AIDS, leukemia, other cancers, etc.). Gene therapy techniques based on genetically manipulated stem and/or germ cells may also be useful in cloning organisms, such as animals. However, genetically manipulating stem cells using many current technologies is difficult, typically employing viruses or gene carriers that can be time consuming and expensive, or may be dangerous to perform and may not have high yields. Current research findings also suggest that the practical implementation of animal organ transplants into human recipients also may require procedures involving stem cells from both the donor and recipient. Many of these promising therapies would require cryopreservation and storage of donor specimens including human stem cells, for example, as derived from the stem cell-rich umbilical cord blood of newborns, which can provide such donors with a therapeutic basis for hematopoietic reconstitution or gene therapy should a health emergency occur later in life. If such storage demands are to be realistically met, the specimens will need to have minimal volume, and, therefore, successful implementation of such technologies may rest on the development and availability of effective methods for isolating trace numbers of stem cells from sources such as umbilical cord blood and the fetal liver. In order to achieve broad implementation of the therapies discussed above and others, rapid and cost effective methods are needed to isolate, with high purity, desired target cells from suspensions having a diverse mix of cell types and concentrations.

The use of applied electric fields to physically manipulate cells is known. Applied electric fields have been employed in the prior art for cell inactivation and sub-lethal cell membrane electroporation. For example, U.S. Pat. No. 5,048,404 to Bushnell discloses a system and method for sterilizing liquid foodstuffs by killing microorganisms with exposure to pulsed electric fields.

Sale and Hamilton ("Effects of High Electric Fields on Microorganisms 1. Killing of Bacteria and Yeasts," *Biochim et Biophys Acta,* 148:781 (1967); and "Effects of High Electric Fields on Microorganisms 11. Mechanism of Action of the Lethal Effect," *Biochim et Biophys Acta,* 148:789 (1967)) studied the effect of pulsed electric fields on suspensions of bacteria or suspensions of yeasts. Specifically, they investigated the effect on the degree of cell kill by the field as a function of field strength and exposure time. The effect of pulsed electric fields on the killing of bacteria was also studied by Hülsheger et al. ("Lethal Effects of High-Voltage Pulses on *E. Coli* K12," *Radiat Environ Biophys,* 18:281 (1980); and "Killing of Bacteria with Electric Pulses of High Field Strength," *Radiat Environ Biophys,* 20:53 (1981)). Hülsheger et al. studied the effects on bacterial cell death of a variety of experimental parameters and were able to demonstrate a 99.9% reduction in the number of living bacterial cells in suspensions after exposure to certain pulsed electric field parameters.

The lysis of erythrocytes in erythrocyte suspensions by pulsed electric fields has also been studied both for bovine (Sale and Hamilton, "Effects of High Electric Fields on Microorganisms III. Lysis of Erythrocytes and Protoplasts," *Biochem et Biophys Acta,* 163:37 (1967)) and human (Kinosita and Tsong, "Voltage-Induced Pore Formation and Hemolysis of Human Erythrocytes," *Biochim et Biophys Acta,* 471:227 (1977); and Kinosita and Tsong, "Hemolysis of Human Erythrocytes by a Transient Electric Field," *Proc Natl Acad Sci.* 74:1923 (1977)) erythrocytes. Knowledge derived from the studies above indicates that applied electric fields resulting in cellular transmembrane potentials on the order of 1 Volt can result in colloidal osmotic lysis of the erythrocytes.

Electric fields have also been used to sublethally porate the plasma membrane of nucleated cells, such as leukocytes and Chinese Hamster Ovary (CHO) cells (Sixou and Teissié, "Specific Electropermeabilization of Leukocytes in a Blood Sample and Application to Large Volumes of Cells," *Biochim et Biophys Acta,* 1028:154 (1990)). Sixou and Teissié investigated electropermeabilization conditions to enable reversible poration of cell membranes, while maintaining long-term cell viability, for the purpose of enabling the reversibly porated cells to uptake drugs and act as immunocompatible drug delivery vehicles within the body. Sixou and Teissié studied the effect of pulsed electric field parameters on the reversible poration of suspensions comprising single cell types and suspensions comprising mixtures of two cell types (e.g. CHO cells and erythrocytes, and leukocytes and erythrocytes). The authors showed that reversible electropermeabilization is a function of the cell size and that large cells are reversibly porated at lower electric field strengths than small cells.

While the above mentioned methods and systems for cell separation and cell electropermeabilization represent, in some cases, valuable and useful techniques for some applications, there remains a need in the art for simple, fast, and clean methods to selectively isolate or remove specific cell sub-populations from cell suspensions without causing undo damage or activation to the remaining cells and without employing undesirable or toxic agents.

SUMMARY OF THE INVENTION

Accordingly, the present invention can provide relatively simple, fast, and clean methods for cell isolation or purging based on physical differences between different cell types present in a suspension. Furthermore, the invention provides systems and methods that enable selective isolation of viable cells, selective cell inactivation, as well as stem cell electropermeabilization, using applied electric fields.

In one aspect, the invention provides a method for creating from a biological sample having a given cell population, a suspension of cells that contain a selected viable subpopulation of the given cell population. The method is based on a characteristic electroporation threshold of the cells. The subpopulation of cells selected by the method is substantially limited to cells that have a characteristic electroporation threshold that is greater than a predetermined electroporation threshold. The selected suspension of cells is produced from the biological sample by first subjecting the sample to an electric field that has a magnitude that is sufficient to porate a substantial fraction of the cells in the sample that have a characteristic electroporation threshold less than the predetermined electroporation threshold. The electric field, however, does not porate a substantial fraction of cells that have a characteristic electroporation threshold greater than the predetermined electroporation (threshold. Essentially, all of the porated cells in the sample that is subjected to the electric field are also inactivated.

In another aspect, the invention provides a method for creating a selected subpopulation of discreet objects from a sample having a given population of discreet objects. A discreet object comprises an inner conductive core which is surrounded by a dielectric membrane. The method is based on a characteristic electroporation threshold of the discrete objects. The subpopulation of discrete objects selected by the method is substantially limited to discrete objects that have a characteristic electroporation threshold that is greater than a predetermined electroporation threshold. The selected suspension of discrete objects is produced from the sample by first subjecting the sample to an electric field that has a magnitude that is sufficient to cause irreversible dielectric breakdown of the dielectric membrane of a substantial fraction of the discrete objects in the sample that have a characteristic electroporation threshold less than the predetermined electroporation threshold. The electric field, however, does not cause irreversible dielectric breakdown of the dielectric membrane of a substantial fraction of cells that have a characteristic electroporation threshold greater than the predetermined electroporation threshold.

In yet another aspect, the invention provides a method for porating cells. The method includes supplying a suspension of cells in a treatment volume, where the treatment volume includes at least two electrodes that are in fluid contact with the suspension. The method further involves applying a time varying bi-polar electrical potential across the electrodes that is sufficient to create an electric field that is sufficient to porate at least one cell in the suspension. The bi-polar electrical potential is varied so that the average current across the sample over the entire treatment time is essentially zero.

In another aspect, the invention provides a method for reversibly porating stem cells. The method involves supplying in a treatment volume a suspension of cells including a plurality of stem cells, which stem cells have a characteristic size, a characteristic shape, a plasma membrane, and a nuclear membrane. A pulsed electric field that has a pulse duration and magnitude sufficient to porate the plasma membrane of a cell having a characteristic size and shape essentially identical to the stem cells, but having an effective membrane thickness substantially exceeding the average membrane thickness of the plasma membrane of the stem cells is then applied to the suspension.

In another aspect, the invention involves a system for creating from a biological sample having a given cell population, a suspension containing a selected viable subpopulation of the given cell population. The selected cell population is substantially limited to cells that have a characteristic electroporation threshold greater than a predetermined electroporation threshold. The system functions by inactivating a substantial fraction of the cells in the sample not included in the selected subpopulation. The system includes a generating mechanism that generates an electric field of a magnitude and duration sufficient to irreversibly porate a substantial fraction of the cells not included in the selected subpopulation, while not irreversibly porating a substantial fraction of the cells included in the selected subpopulation. The system further includes a treatment cell that is electrically connected to the generating mechanism and is adapted to contain a cell suspension.

In yet another aspect, the invention provides a system for selectively inactivating biological cells based on a difference in a characteristic electric poration threshold. The system includes a generating mechanism that generates an electric signal constructed and arranged to create desired electric field parameters. The system also includes a treatment cell that is electrically connected to the generating mechanism, includes at least one electrode, and includes a treatment volume adapted to contain a cell suspension. The electrode is in fluid contact with the cell suspension during operation of the system and is constructed of a porous, biocompatible material, which is sealed in order to reduce the release of gases from the electrode during operation of the system.

In another aspect, the invention involves a cell suspension comprising a plurality of biological cells suspended in a liquid. The suspension includes one population of cells, which have a maximum of characteristic size not more than a predetermined value, that are substantially viable, and another population of cells, having a maximum characteristic size greater than the predetermined value, that are substantially non-viable. The cell suspension is obtained from a precursor suspension of substantially viable cells that contains as subpopulations the two cell populations mentioned above. The cell suspension is obtained by subjecting the precursor cell suspension to an electric field having a magnitude and duration that is sufficient to irreversibly porate a substantial fraction of the cells in the precursor suspension that have a maximum characteristic size above the predetermined value.

In yet another aspect, the invention involves a cell suspension comprising a plurality of biological cells suspended in a liquid where each of the biological cells is enclosed by a plasma membrane. The cell suspension includes a subpopulation of biological cells that possess a maximum characteristic size in excess of a predetermined value. Furthermore, the cells in the subpopulation of cells having a maximum characteristic size in excess of the predetermined value also have a maximum transmembrane electrical potential that exceeds that required to cause irreversible dielectric breakdown of the plasma membrane of the cells.

In another aspect, the invention provides a cell suspension comprising a plurality of non-cultured biological cells, including a plurality of viable stem cells that have a given characteristic size, suspended in a liquid. The cell suspension further includes a plurality of irreversibly porated cells, essentially all of which irreversibly porated cells have a characteristic size that is greater than the characteristic size of the stem cells.

In another embodiment, the invention provides a cell suspension including a plurality of viable, reversibly electroporated stem cells.

In yet another aspect, the invention involves a suspension comprising viable, human pluripotent lympho-hematopoietic stem cells, which are capable of differentiating into members of the lymphoid, erythroid, and myeloid lineages. The suspension is essentially free of mature and lineage committed cells and is derived from a precursor cell suspension comprising substantially viable cells. The suspension is derived from the precursor suspension by subjecting the precursor suspension to an electric field of sufficient duration and magnitude to inactivate a substantial fraction of the mature and lineage committed cells in the precursor suspension.

Other advantages, novel features, and objects of the invention will be become apparent from the following detailed description of the invention when considered in conjunction with the accompanied drawings, which are schematic and which are not intended to be drawn to scale. In the figures, each identical or nearly identical component is illustrated in various figures is represented by a single numeral. For purposes of clarity, not every component is labeled in every figure.

BRIEF DESCRIPTION OF THE DRAWINGS

FIG. 1*a* is a schematic illustration showing a cross-section of a cell suspended in an electric field between two electrodes;

FIG. 1*b* is a schematic illustration of a portion of the cell membrane from the cell in FIG. 1 for an applied electric field strength of zero;

FIG. 1*c* is a schematic illustration of a portion of the cell membrane from the cell in FIG. 1 for an applied electric field strength less than the critical applied electric field strength;

FIG. 1*d* is a schematic illustration of a portion of the cell membrane from the cell in FIG. 1 for an applied electric field strength approximately equal to the critical applied electric field strength;

FIG. 1*e* is a schematic illustration of a portion of the cell membrane from the cell in FIG. 1 for an applied electric field strength exceeding the critical applied electric field strength;

FIG. 2*a* is a schematic illustration showing a cross-section of a typical stem cell;

FIG. 2*b* is an electrical circuit diagram illustrating how a cell charges in response to an applied electric field;

DETAILED DESCRIPTION OF THE INVENTION

Figure 3:
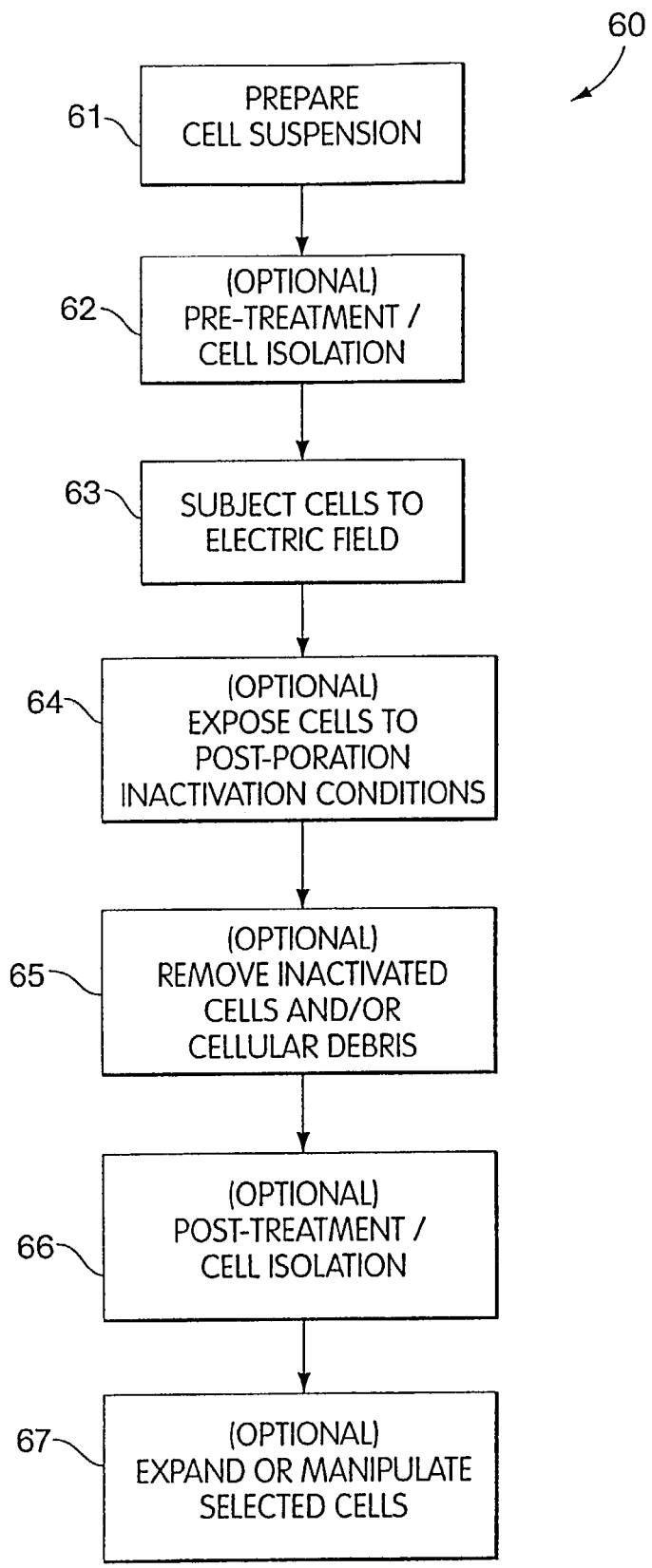
FIG. 3 is a flow chart outlining the steps of certain embodiments of the inventive method.

The present invention provides novel methods and systems for selectively inactivating biological cells, or any discrete objects having an inner conducting core surrounded by a dielectric layer, for example a lipid bilayer membrane. Specifically the invention provides methods and apparatus for selectively inactivating such cells or discrete objects by subjecting a suspension containing such cells or discrete objects to an applied electric field of sufficient duration and magnitude to cause dielectric breakdown or electroporation of the dielectric layer. The methods provided by the present invention can be used advantageously to selectively inactivate subpopulations of cells or discrete objects from a precursor population that contains a mixture of different cells or discrete objects, or mixtures of cells and non-cell discrete objects, on the basis of a characteristic electroporation threshold, thus providing a means for selectively purging or isolating cells or discrete objects from larger populations. One embodiment of the inventive method involves subjecting a sample having a given population of cells or discrete objects to electric field conditions sufficient to porate a substantial fraction of cells or discrete objects that have a characteristic electroporation threshold below a selected predetermined value, while not simultaneously porating a substantial fraction of the cells or discrete objects having a characteristic electroporation above the predetermined value, and subsequently, or simultaneously inactivating the porated cells or discrete objects.

The term "biological cell" or "cell" as used herein has its commonly understood meaning and includes viable, potentially viable, or previously viable cells derived from a biological sample. Such cells include prokaryotic cells such as bacteria, and algae, and eukaryotic cells, such as yeasts, fungus, plant cells, and animal cells. Such cells typically have an inner, electrically conducting core comprised of cytoplasm, surrounded and enclosed by at least one dielectric membrane, for example the cytoplasmic or, equivalently, plasma membrane. Eukaryotic cells, in addition, typically also possess a dielectric nuclear membrane surrounding a conductive nucleus within the interior of the cell.

The term "discrete objects having an inner conducting core surrounded by a dielectric layer" or simply "discrete object" as used herein refers to any object comprising a substance exhibiting a relatively low electrical resistivity surrounded and enclosed by a dielectric layer or dielectric membrane having a much higher electrical resistivity. Such discrete objects include biological cells as previously described, but also include objects such as certain viruses, sub-cellular organelles, liposomes, micelles, and others. Throughout the remainder of this detailed description, many of the methods and apparatus of the invention are described in relation to biological samples comprising biological cells. It should be understood that the invention is not so limited and that the invention may similarly be applied to discrete objects, as defined herein, other than cells. Also, whenever the term "discrete object" is used herein, it should be understood that the term includes, as a subset, biological cells. The term "dielectric layer," or "dielectric membrane," or "membrane" as used herein refers to a continuous layer or coating having a finite thickness and having an electrical resistivity ($\Omega \cdot cm$) exceeding that of a conducting core which the membrane encloses. Typically, the electrical resistivity of the dielectric layer will exceed that of the inner conducting core by at least a factor of 10, and more typically, for example as is the case with most biological cells, by at least a factor of $10^4$-$10^9$. In the context of biological cells, the dielectric layer is defined by at least one lipid bilayer membrane, together with any associated structures or substances associated therewith which affect the effective membrane thickness or resistivity of the dielectric layer. "Effective," as used herein in the context of membrane thickness or resistivity, refers to a thickness or resistivity of an equivalent membrane not possessing any associated structures or substances affecting its dielectric properties associated therewith that possesses the same dielectric properties as the actual membrane having such associated structures or substances.

The term "inactivating" as used herein refers to destruction of at least one property of a discrete object. In the context of biological cells, inactivating is equivalent to rendering unviable, or killing the cell. As applied to non-cell discrete objects, inactivate can refer to physical destruction of the object, or simply a destruction of the permi-selective diffusional barrier properties of the dielectric layer with respect to at least one molecular, ionic, or atomic species. In certain embodiments involving cells, inactivation may involve not only rendering the cells non-viable, but also irreparably lysing and physically disrupting and destroying the physical structure of the cell.

The invention provides, in some embodiments, relatively fast and effective methods for purifying certain desired cells in a viable state from a suspension or eliminating certain undesired cells from a cell population. As mentioned, the methods involve exposing a suspension containing a population of cells to an applied electric field, which field has a magnitude and is applied for a duration selected to porate, and in some embodiments inactivate, a substantial fraction of certain subpopulations of cells based on their characteristic electroporation threshold. The term "suspension of cells" as used herein refers to a mixture of cells suspended in a carrier liquid. The carrier liquid may be naturally part of the biological sample from which the cells derive, for example blood is a suspension of blood cells suspended in plasma, or, for cells which are not normally present in a suspension, the carrier liquid can be any suitable diluent or medium. Preferred carrier fluids are non-toxic and physiologically compatible with the cells they suspend, at least for a time period equal to that of the electric field application procedure. Preferred carrier fluids are also electrically conductive. The electrical conductivity can be any value greater than zero, but preferably will range from about 10%-200% that of the conductive core of the cell. In certain embodiments, the conductivity or resistivity of the carrier fluid will be essentially equal to that of the conductive core of the cell. In other embodiments, in order to reduce the power consumption of the electric field generating apparatus and/or reduce the degree of heating of the cell suspension, as will discussed in greater detail herein, it can be preferable to utilize a carrier fluid having a resistivity that is greater than that of the conductive core of the cell. In order to provide a more uniform electrical field throughout a cell suspension being treated according to the invention, the cell suspension should be essentially free of gas bubbles. The cells in the suspension should also be individually suspended and as free from clumping and aggregation as possible during application of the electric field in order to provide the maximum resolution and selectivity attainable for a given set of electric field exposure conditions. The concentration of cells in a cell suspension, as will be discussed in more detail, can also affect the selection and performance of the applied electric field. Typically, for mammalian cells, the range of total cell concentrations in treated samples can range from about $10^2$-$10^{10}$ cells/ml, with preferred suspensions having from about $10^4$-$10^8$ cells/ml.

The term "substantial fraction" or "substantially depleted" as used herein, in the context of discrete objects having a characteristic electroporation threshold less than a predetermined value, refers to at least 25% of such cells being porated by the applied electric field and inactivated, preferably at least 50%, more preferably at least 90%, in some embodiments preferably at least 99%, in some embodiments preferably at least 99.99999%, and in some embodiments preferably essentially all of the discrete objects. The term "electroporation threshold" or "critical electroporation threshold" as used herein refers to the susceptibility of a particular cell or subpopulation to membrane poration by an applied electric field. As will be discussed in greater detail herein, the characteristic electroporation threshold of a cell or subpopulation of cells is a function of the physical and chemical properties of the cell that influence its interaction with an applied electric field. Differences between one or more of these properties between different cells or subpopulations may be advantageously exploited to provide a basis for selective isolation and inactivation according to the invention. Such properties include characteristic cell size, effective dielectric membrane thickness, cell shape, cell and/or membrane morphology, cell membrane capacitance, cytoplasmic electrical resistivity, etc. The term "predetermined electroporation threshold" as used herein refers to a chosen value of electroporation threshold below which a significant fraction of cells having such electroporation thresholds will be porated by the applied electric field, and above which a significant fraction of cells having such electroporation thresholds will not be porated. The predetermined electroporation threshold, as will be discussed in greater detail herein, can be a function of the parameters of the applied electric field (e.g. field strength, field duration, etc.) and the electrical properties of the cell suspension (e.g. fluid carrier resistivity, total suspension capacitance, etc). An important feature of the invention is the selection of such electric field parameters and suspension properties in order to provide conditions that selectively inactivate a significant fraction of one or more subpopulations of cells in a sample based on one or more differences in their properties that affect their characteristic electroporation threshold.

The methods and apparatus provided by the present invention can be applied to a wide variety of discrete object separation applications, and to a wide variety of biological and non biological samples. One important embodiment of the invention provides a method of isolating or inactivating discrete objects based on a characteristic size. "Characteristic size" or "size" as used herein with respect to dimensions of cells or discrete objects, refers a linear dimension of a cell or discrete object as measured in the direction of an applied electric field to which the cells or objects are subjected and from an external surface of the outermost dielectric membrane on one side of the geometric center of the cell or object, through the geometric center of the cell or object, to an external surface of the outermost dielectric membrane on the other side of the geometric center of the cell or object. For example, for a spherical cell or object, the characteristic size would be the external diameter of the cell or object. Specifically, the method involves porating and inactivating a substantial fraction of discrete objects above a certain predetermined threshold size, which is a function of the electric field and suspension properties as discussed, while leaving in an uninactivated state a significant fraction of discrete objects below the threshold size. The method can be used, for example, to inactivate cells present in viral preparations used in treatment, diagnosis, or research of viral diseases such as AIDS. It is often desirable to obtain suspensions of pure virus that are essentially uncontaminated with viable cells infected with such virus. Because virus-carrying cells will typically be substantially larger than viruses, the inventive method can be use to selectively inactivate the cells without causing undue damage to the virus. Another application involves isolation of certain sub-cellular organelles from cells. In this case, the cells can initially be porated using the inventive method in order to liberate the intracellular contents of the cells into the suspension. Subsequently, an electric field having different parameters can be applied to the suspension to selectively isolate one or more subpopulations of organelles on the basis of a difference in a characteristic electroporation threshold, for example due to a difference in characteristic size. An example of the inventive method as applied to a non-biological sample is the selective disruption of liposomes on the basis of size. Liposomes are commonly used as vehicles for drug delivery or for transfection of genetic material into cells. The performance of the liposome for its intended task and also potentially its pharmacokinetics within the body can be a function of the size of the liposome. Thus, the current invention can provide a relatively fast and easy means for performing a size selection of manufactured liposomes.

Two important applications where the present invention has particular utility involve the purging of cancer cells from cell suspensions and the isolation and enrichment of stem cells or germ cells from cell suspensions. A "germ cell" as used herein, refers to haploid cells, or gametes, such as sperm or egg cells. These applications are important components in many clinical treatment therapies involving, for example, cancer treatment, organ transplant, and gene therapy. The present method exploits a difference in a critical electroporation threshold between the above mentioned cell types and the other cell types present in the cell suspension to effect a selection of desired cells and/or a purging of undesired cells. In particular, in particular embodiments, differences in characteristic cell size (e.g. average cell diameter) provide, at least in part, for the above mentioned difference in critical electroporation threshold. Cancer cells, for example, are often significantly larger than the desired population of cells, for example stem cells, in a sample and will generally have an electroporation threshold below that of the desired cells. Thus, by subjecting the suspension to a selected electric field having predetermined characteristics, a substantial fraction of the cancer cells can be inactivated without inactivating the desirable cells. Preferably, when a suspension initially containing such cancer cells is subjected to the inventive cell selection method, the concentration of viable cancer cells remaining is decreased by at least a factor of 10 (1 log reduction) and most preferably by at least a factor of 100,000 (5 log reduction). Similarly, because for many biological samples stem cells are the smallest cells present, the inventive method can be used to enrich such a sample in viable stem cells by selectively inactivating non-stem cells in the sample. Preferably, the concentration of viable stem cells, with respect to the total number of viable cells present in the sample, is increased in the sample through application of the inventive method by at least a factor of two, more preferably by at least a factor of five, and in certain preferred embodiments, by a factor of $10^6$ or more, while, correspondingly, the concentration of viable non-stem cells in the sample is substantially depleted. One feature of the inventive method when applied to the purification and enrichment of stem cells, is that unlike typical antibody-based stem cell isolation methods, isolation of stem cells using applied electric fields does not rely on the presence of surface markers on the stem cells (e.g. CD34). The most primitive stem cells may not possess the cell surface markers targeted by typical antibody-based methods and thus, such cells will not be recovered by those methods. Conversely, stem cells isolated by the present methods are selected on the basis of their critical electroporation threshold. Therefore, the stem cell suspensions provided according to the inventive methods, will include stem cells that do not possess the surface markers typically used by antibody-based methods to select stem cells if such stem cells were initially present in the sample before application of the inventive methods. Specifically, one embodiment of the present invention can provide a suspension enriched in stem cells, which is essentially free of mature and lineage committed cells, and which includes as a subpopulation, stem cells not expressing CD34 on their surface.

The stem cell and/or cancer cell containing suspensions can be derived from a variety of sources including, but not limited to, bone marrow, mobilized or unmobilized peripheral blood, umbilical cord blood, fetal liver tissue, other organ tissue, skin, nerve tissue, etc. A variety of stem cells may advantageously be isolated and enriched according to the invention including, but not limited to, hematopoietic stem cells, embryonic stem cells, mesenchymal stem cells, epithelial stem cells, gut stem cells, skin stem cells, neural stem cells, liver progenitor cells, and endocrine progenitor cells. One embodiment of the invention involves the isolation of lympho-hematopoietic stem cells, which are capable of differentiating into members of the lymphoid, erythroid, and myeloid lineages, from cell suspensions including mature and lineage committed cells to provide a suspension of lympho-hematopoietic stem cells that is essentially free of mature and lineage committed cells. The enriched stem cell suspensions according to the present method will also be advantageously enriched in pluripotent stem cells, which have the ability to differentiate into the full complement of mature cells derived from a particular type of stem cell. Also, in some embodiments, the enriched stem cell suspensions produced according to the invention will contain, in addition to pluripotent stem cells, stem cells which are committed colony forming cells. For example, for samples including hematopoietic stem cells, the enriched suspensions can advantageously include viable colony forming cells for granulocytes and macrophages (CFC-GM), colony forming cells for erythrocytes (BFU-E), colony forming cells for eosinophils (CFC-Eo), multipotent colony forming cells (CFC-GEMM), and immature lymphoid precursor cells.

Thus, it is apparent that the present invention provides a novel method for cancer purging and stem cell isolation useful for a variety of medical therapies, an important one of which is stem cell transplantation for hematopoietic reconstitution after myleoablative therapies. A particularly attractive application for the teachings of this invention is the isolation of hematopoietic stem cells from bone marrow, mobilized peripheral blood, umbilical cord blood or fetal liver tissue, which is a crucial first step in an overall protocol for delivering genetically manipulated, stem-cell-based, pathogen countermeasures that have the potential to provide pre-exposure prophylaxes or post-exposure therapies, and immune system reconstitution. Isolation of stem cells to high purity prior to their genetic manipulation is essential for eliminating the interference and complications that occur should other leukocytes be present/viable during gene transfection and expansion. Cryostorage of large numbers of stem cell specimens will be required for large scale implementation of such stem cell-based-countermeasures. Efficient, practical cryostorage of large numbers of specimens demands small specimen volumes. Since the relative concentrations of stem cells in bone marrow mononuclear cell (BMMC) and mobilized peripheral blood mononuclear cells (MPBMC) specimens are approximately $1:10^5$, stem cell isolation and enrichment will be important for achieving small specimen volumes advantageous for efficient cryostorage. To eliminate interference from non-stem cells during expansion and gene transfection, and to reduce volume requirements for cryostorage, isolation strategies should be capable of enriching stem cell concentrations by up to $10^6$ for BMMC and MPBMC specimens.

Many presently available methods typically in use for stem cell isolation or cancer cell purging depend on antibody binding to cell surface structures or toxin-based cell inactivation strategies. These strategies can be sub-optimal for stem cell-enrichment because they provide in some cases relatively low degrees of enrichment and can add detrimental substances to the suspension, such as exogenous antibodies or toxins, that damage or can activate the isolated stem cells or be detrimental to a patient upon reinfusion of such cells. Other currently available stem cell isolation strategies involve a culture-based protocol requiring a long processing time, for example up to one week. In addition, many currently available cell isolation methods do not easily scale, and, therefore, are not optimal for handling the large throughput required for a widespread implementation of many stem-cell-based therapies. Thus, in the prior art, there exists a need for stem cell isolation strategies for effective implementation of the stem-cell-based countermeasures, which the present invention, in some embodiments, potentially can fill.

The methods and apparatus provided according to the present invention can provide significant improvements and advantages over many prior art methods for performing cell separations and isolations. The present method is based on intrinsic differences between cell types, for example characteristic size and/or characteristics that effect the membrane breakdown voltage, such as the dielectric strength of the membrane or the effective membrane thickness, and does not require, in many embodiments, the addition or use of exogenous agents, such as antibodies or toxins, which can adversely affect the viability or state of activation of the isolated cell fraction. "Dielectric membrane breakdown voltage" or "membrane breakdown voltage" refers the voltage across the dielectric membrane layer of a cell or discrete object at the onset of poration of the membrane. In addition, the present method is substantially faster than many prior art cell separation techniques. Cell inactivation and isolation using the inventive method can be performed in times ranging from milliseconds to minutes. Finally, with appropriate selection of operating parameters, as discussed herein, and routine optimization of the selected parameters and method, the inventive method can potentially provide high degrees of enrichment or purging of selected cell subpopulations.

As discussed in more detail later herein, cell selection with electric fields according to the invention can be used as a stand alone method or may be combined with one or more other cell separation methods, such other methods being a pre-treatment or post-treatment step. Also the method according to the invention can be applied to a cell suspension so that the applied electric field both porates and inactivates one or more subpopulations of cells in a single step, or, alternatively, the applied field may porate some or all of the cells to be inactivated without inactivating all of such cells, with the inactivation step performed in a subsequent step. In the former case, the applied electric field is sufficient, under the conditions of its application, to cause irreversible breakdown or irreversible poration of the dielectric membrane of the cell. "Irreversible breakdown" or "irreversible poration" refers to poration that is sufficient to cause death, inactivation, and/or physical disruption of a discrete object without a need for a secondary inactivating step. Inactivation and cell death due to poration are believed to be caused by a loss of the permi-selective nature of the membrane leading to cell death and/or membrane disruption, or a direct physical disruption of the membrane caused by extensive poration. In the case of a loss of the permi-selective nature of the membrane, the inactivation or cell death is ultimately caused by diffusion of previously excluded molecular species, especially small ionic species such as $Na^+$, $K^+$, and $Ca^{++}$, across the membrane followed by an uptake of water across the membrane into the cell in an attempt to achieve osmotic equilibrium with the suspending fluid medium, which can lead to colloidal osmotic lysis and irreparable (fatal) cell lysis, or to a lethal disruption of cellular metabolism. For embodiments involving a method where the applied field porates some or all of the cells to be inactivated without inactivating all of such cells, where the inactivation step is performed in a subsequent step, the poration induced by the applied field is typically less extensive and not irreversible, at least for a certain portion of the porated cells. Given sufficient time, the reversibly porated cells in such samples could seal their pores and retain long-term viability if left in the same fluid carrier or suspending media in which they were subjected to the electric field. The reversibly porated cells may, however, be effectively inactivated by resuspending them in a different post-poration media, adjusting the temperature of the poration media, and/or adding a supplemental agent to the poration media which accelerates cell death, colloidal osmotic lysis, or prevents the resealing of membrane pores. More specific techniques and conditions are discussed below.

The electric field is preferably applied to the cell suspension within a spatially defined treatment cell. The treatment cell can be designed as a static non-flow volumetric container in which the cell suspension to be treated is placed, or more preferably, the treatment cell will include an inlet and an outlet constructed and arranged to enable a cell suspension to continuously flow through the treatment volume. Systems including flow-through treatment cells may be arranged so that the cell suspension passes through the treatment cell only once (one pass) or a plurality of times (recirculating). In addition, either the flow or static systems may include multiple treatment cells. For flow systems, multiple treatment cells can be arranged in a series or parallel configuration.

The treatment cell will include at least one electrode in electrical communication with the cell suspension to be treated. Preferably the treatment cell will include two electrodes placed on either side of and in electrical communication with the cell suspension during operation to which an electric potential is applied to produce an electric field within the treatment volume. In preferred embodiments, the treatment cell and electrodes are constructed and arranged to impose an electric field that is substantially spatially uniform within the treatment volume so that all cells in the suspension are exposed to similar electric field conditions. In some embodiments, the electric field applied to the cell suspension is created by an electric signal applied to the electrodes; however, it is also contemplated that the electric field can be induced in the sample cell via induction by a magnetic field.

In order to reduce the tendency for the electrical potential applied to the electrodes to discharge by arcing, and in order to reduce the degree of electrical heating that occurs in the cell suspension, in certain preferred embodiments, the applied electric field is pulsed for short durations, such durations, except as otherwise described herein, being shorter than the residence time of the treated cell suspension in the treatment volume during the step of subjecting the suspension to the applied electric field. Such electric fields are hereinafter referred to as "pulsed electric fields" or PEFs. The shape of the electric field pulse is preferably substantially rectangular in shape, thus providing very short voltage rise and fall times and a substantially constant magnitude over the entire pulse length. Such rectangular pulse shapes yield the best performance and poration threshold resolution obtainable with the inventive method. While rectangular pulses are preferred, any pulse shape known in the art may be employed in performing the methods of the invention, especially when high resolution is not required, as, for example, when inactivating a cell type that is substantially larger than the desired cell type.

As described previously, the electric field parameters required to effect a desired cell inactivation or isolation depend upon the nature of the cells, the suspension and suspending fluid, and the characteristics of the electric field application apparatus. The exact parameters for any given sample that will yield desired results must be found in practice via routine experimentation. What follows herein is a theoretical development and description of the inventive method, apparatus for performing the method, and important parameters affecting the performance and selectivity of the method to provide guidance to those of skill in the art in selecting parameters to develop successful cell or discrete object isolation and inactivation strategies.

The Fundamental Basis of Electric Field Cell Isolation

The mechanism by which electric fields, and particularly pulsed electric fields (PEFs), isolate cells can be best understood by examining the response of a single discrete object, as exemplified by a biological cell, to an externally applied electric field. A schematic illustration of such a system 50 is shown in FIGS. 1*a-e*. The externally applied electric field 57 can be established by applying a constant voltage or voltage pulse across a pair of electrodes 55 and 56 that are in electrical communication with, and preferably in physical contact with, a cellular suspension containing a plurality of cells, one of which 51 is shown in FIG. 1*a*. Alternatively, the electric field 57 can be applied inductively by creating a time-varying magnetic field throughout the cellular suspension. To preserve the viability of the desired target cells, the carrying fluids in which the biological cells are suspended are typically buffered saline solutions having, in some embodiments, a standard physiological osmolality (e.g. 275-300 mOs/kg-water for most mammalian cells), and a pH in the physiological range (e.g. about 7.0-7.6 for most mammalian cells). The ionic strength of the solutions in certain embodiments is essentially the same as the ionic strength of the intracellular fluid 53 (e.g. about 0.15 M NaCl equivalent for most mammalian cells). As such, these are conducting solutions. Electric field effects on cells can be estimated from the potential theory developed by Coulson (Coulson C A: *Electricity*, Oliver and Boyd, London, Chapter 9, 1951) incorporated herein by reference. This theory implies that induced transmembrane potentials depend on cell size and shape. Formally, the external electric field induces a potential across the cell 51, $V_{cell}$, given by $$V_{cell} = flE \text{ where } f = l \Big/ \left(l - \frac{1}{3}d\right)$$  Eq. 1 and where E is the field strength of the imposed electric field; d is the cell diameter 54, l is the projected length of the cell in the electric field direction 57; and f is a form factor, which is equal to 1.5 for a spherical cell (where l is equal to d) and is approximately unity for large aspect ratio cylindrically shaped cells (where l>>d). In the development to follow, the cells of interest will be assumed to be spherical so that d will be used for l in the following equations and f will be set equal to 1.5. For a more detailed discussion on the effects of non-spherical cell shape and angular orientation with the applied electric field, the reader is referred to Kinosita and Tsong (Kinosita K and Tsong T Y, Voltage-induced pore formation and hemolysis of human erythrocytes, *Biochim et Biophys Acta*. 471:227-242, 1977).

Biological cells have an outer, semipermeable plasma membrane 52 that allows the cell to control its internal environment by its selective permeability. The proper function of this membrane is crucial to the viability of the cell. If the function of this membrane is altered or destroyed, cell death often follows. Plasma membranes are typically lipid bilayers which behave electrically as dielectrics, i.e., they behave as electrical insulators. For eukaryotic cells, as shown in FIG. 1a, the cell nucleus 68 and accompanying nuclear membrane 69 reside within the outer membrane 52, with cytoplasm 53 filling the gap between the nuclear and outer membranes. For prokaryotic cells, there is no nucleus or nuclear membrane, so the cytoplasm, which supports the cell's genetic information (one or more DNA molecules in the form of nucleoids) fills the entire intracellular volume. Cytoplasm, which refers collectively to the substance filling the gap 53 between the outer and nuclear membrane for eukaryotic cells, or the entire intracellular volume for prokaryotic cells, is mainly composed of cytosol, which is a semifluid concentrate having an electrical resistivity that is similar to that of aqueous solutions having a standard physiological ionic strength. As such, the cytosol is electrically conductive, which dictates that the intracellular volume of both eukaryotic and prokaryotic cells is electrically conductive. Thus, biological cells can be viewed as a conducting intracellular region surrounded by a dielectric (insulating) membrane 52. With this conceptual view of biological cells, application of an external electric field 57 causes charge separation to occur inside the biological cell 51 resulting in a nearly constant intracellular potential that has a value corresponding to the boundary average of the potential established on the outer surface of the cell's dielectric membrane 52. If the poles of the cell 51, of which there are two, are defined as the two points formed on the surface of the cell 51 by the intersection of a ray parallel to the electric field direction passing through the center of the cell, then application of an external electric field causes one half of the pole-to-pole potential drop outside of the biological cell 51 to develop across the membrane 52 at each pole of the cell. That is, the externally applied electric field 57 produces a maximum transmembrane potential, $V_m$, at each pole of the cell 51 that scales as $$V_m = V_{cell}/2$$  Eq. 2 or equivalently $$V_m = 3dE/4$$  Eq. 3 for a spherical cell.

Since, in response to an externally applied electric field 57, the potential drop, $V_{cell}$, that develops over a cell's diameter 54 or projected length is transferred approximately equally across the two poles of the cell's membrane 52, the maximum electric field thereby imparted to a cell's membrane 52 is $$E_m = V_{cell}/2t_m,$$  Eq. 4 or, for spherical cells $$E_m = 3Ed/4t_m$$  Eq. 5 or equivalently $$E_m = V_m/t_m$$  Eq. 6 where $E_m$ is the electric field imparted to the membrane 52 for an externally applied electric field 57 of strength E; d is the diameter 54 of the biological cell 51; and $t_m$ is the thickness of the membrane. Thus it is apparent from equation 5, that the imposed electric field within the cell membrane is directly proportional to cell size and applied electric field strength and inversely proportional to the thickness of the cell membrane. Since the size of many typical biological cells falls within a range of 1<d<50 µm and a typical thickness of cell membrane 52 lipid bilayer is approximately 5 nm, the electric field strength imparted to the membrane 52 can be two to three orders of magnitude greater than the strength of the externally applied electric field 57. More specifically, for a typical lipid bilayer membrane thickness of about 5 nm, a transmembrane potential, $V_m$, of approximately one Volt will impart a 2 MV/cm electric field, $E_m$, to the lipid bilayer membrane 52. So for a 10 µm diameter spherical cell, which, for example, is about the mean size of peripheral blood cells, a 2 kV/cm externally applied electric field E would generate the 2 MV/cm electric field, $E_m$, in the lipid bilayer membrane. Since the dielectric strength of many polymers, in response to electric fields, is in the range 0.1-0.5 MV/cm, it is reasonable to expect that a 2 MV/cm electric field imparted to the membrane 52 of a 10 µm diameter cell by an externally applied 2 kV/cm electric field 57 would produce membrane pores by dielectric breakdown. Thus, the electric field magnification provided by the electrical behavior of biological cells can lead to the dielectric breakdown of a cell's membrane 52 when the externally applied electric field has sufficient strength, thereby forming irreversible pores in the membrane which lead to cell death. From equations 1 and 5, it is apparent that the susceptibility of a given cell to poration by an applied electric field 57 is proportional to the magnitude of the applied electric field, E, that is required to produce a given electric field, $E_m$, in the lipid bilayer membrane (which is directly related to membrane poration) and is related to the size of the cells, the thickness of the dielectric membrane, the dielectric strength of the membrane (V/m), the shape of the cells and the orientation of non-spherical cells in the applied electric field. Thus, a difference in one or more of these properties between different cell types can lead to a difference in their characteristic electroporation threshold and can potentially be exploited to effect a selective cell isolation or inactivation using an applied electric field, as described in greater detail to follow. These relations are rigorously valid when the cell is immersed in a conducting fluid, but such fluid may not be required in some embodiments for the inventive method to be functional.

For lipid bilayer membranes, which are typical of many mammalian cells and bacterial cells, the onset of membrane dielectric breakdown in response to an externally applied electric field has been relatively consistently observed in the prior art when the transmembrane potential, $V_m$, reaches a particular critical value, namely $V_m = V_{mc}$, where $V_{mc}$ is the critical transmembrane potential for dielectric breakdown, or, equivalently, the dielectric membrane breakdown voltage. Table 1 summarizes data from cell poration experiments assembled by Castro, et al. (Castro A J, et al: Microbial Inactivation of Foods by Pulsed Electric Fields. Washington State University, Department of Food Science and Human Nutrition, Pullman, Wash., 99164-6376, 1993) (hereinafter "Castro) showing the critical dimensions of various viable cells and their critical membrane potentials for cell membrane poration. The critical dielectric membrane breakdown voltage $V_{mc}$ for these cells were obtained by using Eq. 3 together with results from cell inactivation experiments which measured the critical threshold applied electric field, $E_c$.

TABLE 1

Cell size and induced membrane potential for several microorganisms.

| Microorganism | d (μm) | l (μm) | v (μm³) | f | $V_{mc}$ (V) |
|---|---|---|---|---|---|
| E. coli (4 hr) | 1.15 | 6.9 | 7.2 | 1.06 | 0.26 |
| E. coli (30 hr) | 0.88 | 2.2 | 1.4 | 1.15 | 1.05 |
| K. pneumoniae | 0.83 | 3.2 | 1.7 | 1.09 | 1.26 |
| P. aeruginosa | 0.73 | 3.9 | 1.6 | 1.07 | 1.26 |
| S. aureus | 1.08 | n/a | 0.6 | 1.50 | 1.00 |
| L. monocytogenes I | 0.76 | 1.7 | 0.8 | 1.17 | 0.99 |
| C. albicans | 4.18 | n/a | 38.0 | 1.50 | 2.63 |

In the table, v, is the volume of the cells. With the important exception of young cells (e.g., E. coli, 4 hr culture, in the logarithmic growth phase), the critical membrane potentials $V_{mc}$ of cells in their stationary phase is approximately 1 Volt. A variety of parameters can effect dielectric membrane breakdown voltage, $V_{mc}$. Such parameters include, but are not limited to, the membrane thickness, the dielectric strength of the membrane, the dimensional and chemical uniformity of the membrane, etc. Since, for a given dielectric material, the threshold transmembrane electric field strength, $E_{mc}$, for dielectric breakdown is often similar, and since most of the cells in Table 1 have similar dielectric membranes (lipid bilayers together with any associated protein and/or carbohydrate components), Eq. 6 would suggest that the electrical properties, specifically the membrane thickness, of the membranes having similar $V_{mc}$ are similar. In addition to rapidly growing cells, another important exception to the general rule of 1 Volt being a critical transmembrane potential for cell poration and inactivation are spores in their quiescent state which have been shown to be much more insensitive to electric fields and appear to be sensitive only during germination and outgrowth when the cortex disappears and the spore coat layers dissolve as the cell swells (Hülsheger H., Potel J., and Niemann E-G. Electric Field Effects on Bacteria and Yeast Cells, Radiat. Environ. Biophys. 22:149-162, 1983. (hereinafter "Hülsheger 1983); and Grahl T., Sitzman W., Markl H. Killing of Microorganisms in Fluid Media by High-Voltage Pulses. Presented at 10th Dechema Annual Meeting of Biotechnologists. Karlsruhe, Germany, Jun. 1-3, 1992.). This behavior may be due to the quiescent spores having a much thicker effective dielectric membrane thickness due to the presence of the coat layers. Thus for a given critical transmembrane electric field strength, $E_{mc}$, which is a function of, for example the resistivity and material properties of the dielectric layer, a larger effective membrane thickness would, according to Eq. 6, yield a larger $V_{mc}$, and would thus require a larger critical applied electric field, $E_c$, for cell inactivation (see Eq. 3).

As shown in FIGS. 1b-e, when $V_m$ achieves the critical value $V_{mc}$, membrane dielectric breakdown results in the formation of pores in the cell membrane 52, some of which may reseal upon removal of the externally imposed electric field. FIG. 1b illustrates the condition of a section of cell membrane 52 from near one pole of the cell with no external applied electric field (E=0). When an external field is applied that is below the critical field strength required for poration (E<$E_c$, FIG. 1c) there is a separation of charge across the membrane 52 and a resulting transmembrane potential $V_m$ but no pore formation. This situation for the condition E=$E_c$, is shown in FIG. 1d, where E is the strength of the externally applied electric field and, from Eq. 3:

$$E_c = 4V_{mc}/3d \qquad \text{Eq. 7}$$

which is the critical electric field strength for spherical cells that defines the onset of membrane pore 58 formation for a specific cell size and critical transmembrane potential. When $V_m$ is less than $V_{mc}$ (i.e., when E<$E_c$ in FIG. 1c), pore formation, or at least irreversible pore formation, does not occur. As $V_m$ is increased beyond $V_{mc}$ (i.e., when E>>$E_c$ in FIG. 1e), membrane pores 59 become more numerous, larger, and irreversible. Thus, application of sufficiently strong electric fields, or PEFs to cellular suspensions can result in the inactivation of cells by the formation of irreversible pores which can destroy the function of the semipermeable cell membrane 52. As noted earlier, the proper function of a cell's semipermeable membrane is required to control a cell's intracellular environment and, therefore, to maintain its viability. The critical applied electric field, $E_c$, necessary to form irreversible pores is thus, as is apparent from Eq. 6, directly proportional to the critical transmembrane potential $V_{mc}$, and thus membrane thickness, and inversely proportional to cell diameter d for spherical cells.

PEF Parameters for Cell Purging and Cell Isolation

As noted above, the lethal effect of pulsed electric fields on biological cells is caused by irreversible electroporation of their semipermeable membranes or reversible poration followed by a subsequent treatment to prevent membrane repair or accelerate colloidal osmotic lysis and thereby cause cell inactivation. An electric field applied across the cell electrically polarizes the cell membrane causing charge separation and build up of a transmembrane potential. The critical transmembrane potential required for membrane poration will be a function of the nature and thickness of the membrane, as previously mentioned, and must be determined experimentally for any given system; however, as previously discussed and illustrated by the data in Table 1, for a wide variety of biological cells the critical transmembrane potential associated with an externally applied field is approximately $V_{mc}$=1 Volt. The pores resulting in the membrane structure of the cell due to exposure to field strengths above the critical value can, in certain cases, irreversibly increase cell membrane permeability leading to cell death. The dielectric membrane breakdown concept of cell inactivation is illustrated in FIGS. 1b-e.

Electric field strength, total exposure time, and pulse duration, for PEFs, can be selected to preferentially inactivate biological cells in a suspension which are more susceptible to electric fields due, for example, to their having one or more or a combination of the following properties with respect to other cells in the suspension: a larger average size; a thinner effective dielectric membrane thickness; a more spherical shape, etc. Of particular importance for many biological samples, especially those having cells with similar shapes, such as roughly spherical, and similar dielectric membrane thickness, is selective inactivation of cells based on a difference in characteristic size. Typically, the threshold electric field required for cell inactivation is inversely proportional to the characteristic size of the cell, i.e., from Eq. 7, $E_c(d)=4V_{mc}/3d$, where $V_{mc} \approx 1$ Volt is the critical transmembrane potential for the onset of irreversible pore formation for a wide variety of cell types and d is the diameter or characteristic size of the cell. If the undesirable cells are larger in diameter than the desirable cells, then the pulsed electric field method can be used to selectively inactivate the larger cells. By operating at electric field strengths just below the characteristic electroporation threshold for inactivation of the desirable cells, yet above the characteristic electroporation threshold for the undesirable cells, a substantial fraction of the undesirable cells can be preferentially inactivated while leaving a substantial fraction of the desirable cells (primitive stem cells for example) essentially unaltered and still viable. To further illustrate the utility of the concept, a specific example related to cell isolation from hematopoietic cell suspensions will be illustrated. Table 2 lists the types of blood cells that typically will be present in bone marrow specimens during tumor cell purging and stem cell isolation processing. The cell diameters, relative abundance, and projected threshold electric field strengths ($E_c$ as calculated from Eq. 7 assuming $V_{mc} \approx 1$ volt) for the onset of membrane damage are also provided in the table. Similar cell sizes as those listed would be expected for hematopoietic cells derived from mobilized peripheral blood, umbilical cord blood and fetal liver tissue, although the relative abundance of each may differ. Table 2 clearly shows that the electric field damage threshold for stem cells can be significantly greater than for the other leukocytes present in bone marrow specimens. Furthermore, the electric field threshold for stem cells can be more than a factor of two greater than for breast cancer cells. Since, as will be discussed below, the fraction of cells inactivated by an applied electric field scales exponentially with electric field strength (Hülsheger 1983) the factor of two difference in the critical electroporation threshold should allow essentially complete inactivation of breast cancer cells with preservation of the viability of the cells crucial for autologous transplantation (stem cells).

TABLE 2

Electric field damage thresholds for leukocytes and stem cells.

| Cell Type | Characteristic Size (μm) | Relative Abundance (%) | Projected Electric Field Damage Threshold (kV/cm) |
| --- | --- | --- | --- |
| Stem | 6[a,b] | 0.001[a] | 2.2 |
| Lymphocyte (resting) | 7[b] | 21[c] | 1.9 |
| Lymphocyte (active) | 12[d] | n/a | 1.1 |
| Neutrophil | 12[d] | 73[c] | 1.1 |
| Eosinophil | 13[d] | 4[c] | 1.0 |
| Basophil | 15[d] | 0.1[c] | 0.9 |
| Monocyte | 15[d] | 2[c] | 0.9 |
| Breast Cancer | >15[e] | n/a | <0.9 |

[a]Berardi AC, et al: Functional isolation and characterization of human hematopoietic stem cells. Science, 267:104-108, 1995.
[b]Zipori D, et al: Introduction of Interleukin-3 gene into stromal cells from the bone marrow alters hematopoietic differentiation but does not modify stem cell renewal. Blood 71:586, 1988.
[c]Jandl JH, Blood: Textbook of Hematology, Little, Brown and Company, Boston/Toronto, 1987.
[d]Henry JB: Clinical Diagnosis and Management by Laboratory Methods, 16th Ed., W.B. Saunders Company, Philadelphia, PA, Vol. 1, 1979.
[e]from observations by inventors Another feature which, in the present example, further can enhance the ability to perform preferential electric field isolation of stem cells and/or to purge relatively large tumor cells, such as breast cancer cells, involves the quiescent nature of stem cells. As discussed in Berardi, et al., stem cells are quiescent and are unaffected by an anti-metabolite treatment, whereas rapidly proliferating cells are inactivated by an anti-metabolite treatment. A similar phenomenon has been observed (Hülsheger 1983) with PEF inactivation of *Escherichia coli* (*E. coli*). The observations of Hülsheger 1983 indicate that the stationary growth phase *E. coli* cells (quiescent cells) are much less vulnerable to the lethal effects of PEF's than are the larger, rapidly dividing *E. coli* cells that are in the logarithmic growth phase. Based on these considerations, it is expected that stem cells, due to their quiescent nature and smaller size, will be much less vulnerable to the lethal effects of electric fields and PEFs and that electric field strength can be used to preferentially inactivate a substantial fraction of non-stem cell leukocytes and tumor cells while leaving a substantial fraction of the stem cells unharmed. Thus, it is expected that the inventive methods will be an effective approach for purging tumor cells from autologous transplant tissue. Similarly, the inventive methods may be applied to other cell suspensions or suspensions on non-cell discrete objects having differences in characteristic size between subpopulations in order to selectively isolate or inactivate selected subpopulations.

In addition to performing a selective cell isolation or inactivation on the basis of a difference in characteristic cell size by selecting an appropriate applied electric field strength, the method can also be employed to select cells that can be similar in size based on a difference in dielectric membrane breakdown voltage, for example, due to a difference in effective membrane thickness. For example, a variety of cells, such as some epithelial cells and cancer cells, can have a layer of mucopolysaccharide coating associated with their plasma membrane which may increase the effective thickness of the membrane and make the cells less susceptible to an applied electric field than would be predicted by Eq. 7 with $V_{mc}$ assumed to be 1 Volt. In fact, assuming that the critical electric field imparted to the membrane required for poration, $E_{mc}$, is similar for the cells present in the suspension, Eq. 6 indicates that the critical transmembrane potential $V_{mc}$ will be directly proportional to the effective thickness of the dielectric layer, and, therefore, from Eq. 7, the critical applied electric field strength, $E_c$, for poration will also be directly proportional to the effective membrane thickness. Thus, an applied electric field strength may be chosen that is sufficient to inactivate a substantial fraction of cells having an effective membrane thickness below a certain predetermined threshold without inactivating a substantial fraction of the cells having an effective membrane thickness above the threshold.

Although the threshold electric fields for the cells comprising harvested human bone marrow, as exemplified above, were theoretically estimated based on their size (see Table 1), the critical threshold electric fields for the cells listed in Table 1 have been previously measured. In addition to the importance of the magnitude of the applied electric field strength, total exposure time of the cells to the electric field is also an important parameter in determining the degree of inactivation of a given population of cells. In general, for cells that are selectively inactivated by electric fields on the basis of cell size, the electric field strength determines the size below which cells are preserved, and total electric field exposure time determines the relative reduction in cells having sizes above the critical size. Experiments in the prior art have been conducted over a wide range of pulsed electric field strengths and number of applied pulses and have led to an empirical model developed by Hülsheger 1983, herein incorporated by reference, for the surviving fraction of cells, s, following electric field treatment, as a function of the peak applied electric field strength, E, and the total time the cells are exposed to the electric field, t. The time t in the following model sums the on-time of the electric field over the total number of pulses, so that $t=N_p\tau_p$, where $N_p$ is the number of applied pulses and $\tau_p$ is the time duration of each pulse over which $E \geq E_c$. Hülsheger 1983 demonstrated that bacterial cell surviving fraction can be roughly modeled by an empirical expression that is a power law function of time and an exponential function of electric field strength. Equation 8 provides a variant of Hülsheger's rough model that behaves correctly as the exposure time approaches zero for $E > E_c$.

$$s = \left(\frac{t}{t_c}+1\right)^{-\frac{(E-E_c)}{k}} \quad \text{Eq. 8}$$

where, s is surviving fraction (ranging from $0 \rightarrow 1$), $E_c$ is the threshold value of the electric field strength for membrane breakdown, $t_c$ is an exposure tine normalization constant, and k is an electric field normalization constant. $E_c$, $t_c$ and k can be empirically determined for a given cell suspension by fitting Eq. 8, to data taken relating fractional inactivation as a function of exposure time and applied electric field strength using any suitable regression analysis apparent to one of skill in the art.

The equation for surviving fraction s can be utilized as a tool to analyze data collected for the surviving fraction of a particular cell population vs. applied electric field strength and exposure time, generated for a given cell suspension, and as a guide for selecting the field strength and duration required to achieve a desired survival fraction for cells which are to be porated and inactivated. By prescribing appropriate values for the electric field strength and total exposure time, required reductions in populations of cells of electroporation threshold below a critical value, for example having sizes larger than a critical diameter, can be achieved. Eq 8 indicates that s is a strong exponential function of electric field strength E and a weaker power law function of total electric field exposure time t.

Thus, isolation and inactivation of cells or discrete objects by size differences according to the present invention proceeds by selecting an appropriate applied electric field strength $E_c$ so that cells of size greater than (from Eq. 7), $d = 4V_{mc}/3\,E_c$ will be inactivated and then applying an appropriate number of electric field pulses and/or total electric field exposure time to reduce the viable fraction of cells above the critical size to the desired level.

Table 3 presents the results of cell inactivation experiments assembled by Castro on a variety of microorganisms using Hülsheger's original form of Eq. 8, which is obtained by removing the factor "+1" in Eq. 8 (Hülsheger 1983). The threshold electric field $E_c$ derived from lethality measurements for *E. coli* in the logarithmic growth phase is shown in Table 3 to be 0.7 kV/cm, while the threshold field for *E. coli* in the stationary phase is more than 10 times higher, i.e., 8.3 kV/cm. The lower threshold electric fields required to irreparably porate the membranes of growing cells are related to the fact that growing cells are larger and must take in nutrients from the external environment, making them more susceptible to electric fields.

TABLE 3

Experimental conditions, values, and confidence limits for model parameters.

| Microorganism | E (kV/cm) | t (ms) | $E_c$ (kV/cm) | $t_c$ (ms) | k (kV/cm) |
|---|---|---|---|---|---|
| *E. coli* (4 hr) | 4-20 | 0.7-1.1 | 0.7 ± 3.1 | 11 ± 9.6 | 8.1 ± 1.8 |
| *E. coli* (30 hr) | 10-20 | 0.7-1.1 | 8.3 ± 0.3 | 18 ± 5.7 | 6.3 ± 1.0 |
| *K. pneumoniae* | 8-20 | 0.7-1.1 | 7.2 ± 2.0 | 29 ± 16 | 6.6 ± 1.4 |
| *P. aeruginosa* | 8-20 | 0.7-1.1 | 6.0 ± 0.4 | 35 ± 6.1 | 6.3 ± 1.1 |
| *S. aureus* | 14-20 | 0.7-1.1 | 13 ± 0.9 | 58 ± 17 | 2.6 ± 0.7 |
| *L. monocytogenes* I | 12-20 | 0.7-1.1 | 10 ± 2.6 | 63 ± 12 | 6.5 ± 2.5 |
| *C. albicans* | 10-20 | 0.7-1.1 | 8.4 ± 7.5 | 110 ± 33 | 2.2 ± 0.9 |

One embodiment of the invention, involving cancer cell purging and stem cell isolation by applied electric fields such as pulsed electric fields, is based on the observation that non-stem-cells are typically larger in size than stem cells; therefore, Eq. 7 and the observation that $V_{mc}$ is typically about 1 Volt for a wide variety of cell types implies that an electric field strength, $E_c$, can be selected that will inactivate a substantial fraction of cells larger than the stem cell, including contaminating tumor cells. After selecting an appropriate predetermined critical electric field strength (which can be approximately E=2-2.2 kV/cm to preserve stem cell viability), total electric field exposure time, t, can then be selected with guidance from Eq. 8, and routine experimental optimization, in order to achieve the desired reduction in the unwanted, non-stem-cell populations, most importantly, tumor cell populations. Therefore, electric field conditions can be determined that lead to effective tumor cell inactivation and stem cell preservation, which is crucial for effective transplant tissue purging.

Unlike stem cell isolation and purging strategies based on anti-metabolites, mechanical cell sorting, or antibody binding strategies, the present invention has the potential to isolate stem cells without damage and without mutation of the basic genetic molecules (DNA/RNA) within the cell. Most importantly, the genetic material is shielded from the pulsed electric fields by the conductivity of the cell nucleus and cytoplasm. Furthermore, at the electric field strengths of interest for isolating stem cells (about 1-3 kV/cm), the potential developed across critical bonds in these complex RNA/DNA molecules is generally not sufficient to break these bonds. Hence, stem cell isolation with pulsed electric fields should not cause undo damage to the genetic material within the cells. An additional advantage of using the electric-field-based tumor cell purging, stem cell isolation strategy is centered on the fact that toxic or potentially activating agents, such as anti-metabolites or exogenous antibodies, are typically not placed in physical contact with the stem cells.

As previously mentioned, because of difficulties in applying a continuous potential across electrodes without arcing or discharge, electrochemical reactions, and excessive heat generation, the applied electric field is preferably supplied to the suspension as a series of short pulses, i.e. as a PEF. The maximum electric field pulse duration is typically limited by electric breakdown due to arcing between electrodes in the treatment volume and by single pulse heating effects. The pulse repetition rate is limited by the maximum temperature rise that can be sustained without causing undo damage to the sample. The minimum allowed pulse duration should be greater than the time constant at which the dielectric membrane charges in response to the electric field, as will be discussed in greater detail herein.

Thus far, the effect of applied electric field strength and exposure time on the performance of the inventive methods have been discussed in detail. In addition, as mentioned earlier, a variety of other parameters related to the PEF, suspension, pulsing medium (fluid carrier), and other processing steps can affect the performance of the inventive method and should be considered when developing an effective isolation or inactivation protocol. What follows is a description of a number of what are believed are important factors related to performance. Throughout the description, reference will be made to one embodiment of tumor cell purging and stem cell isolation from suspensions of hematopoietic cells in order to illustrate the concepts with a concrete example. It should be understood that the particular example chosen is purely exemplary, and the methods may be practiced on a wide variety of samples for a wide variety of desired applications. Table 4 below summarizes some of the more important parameters (column 2) that can influence PEF performance, particularly as related to tumor cell purging and stem cell isolation, along with contemplated preferred ranges (column 3) of some chosen parameters for tumor cell purging and stem cell isolation. The table will serve as an outline for the discussion to follow. The "PEF" group includes parameters related to the nature of the applied electric field. The "Pulsing Medium" group includes parameters related to the properties of the suspension. The "Post Processing" group discusses optional treatments subsequent to electric field exposure that can, in some cases, enhance performance, and the "Heat Transfer" group includes parameters related to the heating effects of the applied PEFs.

TABLE 4

Parameters influencing PEF tumor cell purging and stem cell isolation efficacy.

| Group | | Parameter Description | Range |
|---|---|---|---|
| PEF | — | Electric field pulse shape | "Rectangular" |
| | E | Electric field strength | 0.5-5 kV/cm |
| | t | Total electric field exposure time | <10 ms |
| | $\tau_p$ | Electric field pulse duration | 2-20 µs |
| Pulsing | $\eta_{ps}$ | Initial leukocyte concentration | $10^6$-$10^8$ cells/ml |
| Medium | $\mu_{ps}$ | Pulsing medium ionic strength | 0.015-0.15 M KCl equivalent |
| | $\gamma_{ps}$ | Pulsing medium osmolality | ≦300 mOsm/kg-water |
| | — | Agents for cell size modification | |
| | — | Agents for dielectric membrane breakdown voltage modification | |
| Post Processing | $\mu_{Is}$ | Inactivation medium ionic strength and composition | 0.15 M KCl equivalent, Ca$^{++}$ |
| | $\tau_{Is}$ | Inactivation medium residence time | |
| | — | Collection protocol | Gradient density centrifugation |
| Heat Transfer | $F_p$ | Electric field pulse rate | Apparatus & pulsing medium dependent |
| | $T_{ps}$ | Pulsing medium temperature | 5-41 °C. |

For embodiments involving PEFs, a substantially rectangular electric field pulse shape is preferred for achieving optimum size selectivity. Rectangular pulses are those that have rise and fall times that are short compared to the pulse duration, and preferably shorter than the charging time scale of the dielectric membrane of the cells or objects to be inactivated (typically rise and fall times are ≦0.5 µs for most applications of interest in the present invention), have essentially no overshoot during the rise- and fall-time transients, and have a substantially constant electric field strength between the rise and fall transients; preferably the difference in the maximum and minimum values in the substantially constant field strength region is less than 3%. Non-rectangular-shaped pulses, such as half-sinewave shaped or exponentially decaying pulses may be employed for some embodiments but will not provide as clearly defined an electric field strength, which can broaden the electroporation threshold demarcation line between uninactivated and PEF inactivated cells, thereby degrading the selectivity, resolution, and efficiency of the PEF cell inactivation method.

The range of electric field strengths given in Table 4 is based on the critical electric field strengths given in Table 2 and represents a reasonable range to employ for optimization trials involving the inactivation of specific cell types listed in Table 2 as a function of electric field strength and total exposure time. With this electric field range, the range of inactivation that can be expected would range from no lethal effects on any cells to essentially total inactivation of all cell types. Based on Eq. 8, total electric field exposure time t can be used to achieve a desired reduction in the number of viable unwanted cells. The maximum total electric field exposure time typically will be less than about 10 ms for essentially complete inactivation of tumor cell populations.

For embodiments involving PEFs, the inactivation of biological cells involves multiple steps which are dependent on the duration of the individual electric field pulses $\tau_p$. Early in the pulse, the membrane of the cell charges, thereby producing an elevated transmembrane potential. The membrane charging time scale $\tau_m$ for spherical cells is given by (Lynch P T and Davey M R, *Electrical Manipulation of Cells*, Chapman and Hall, pp. 18-20, 1996.; and Tessié J and Tsong T Y, Electric field induced transient pores in phospholipid bilayer vesicles, *Biochemistry* 20:(6)1548-1554, 1981.):

$$\tau_m = \tfrac{1}{2} c_m d(\rho_c + \rho_{ps}/2), \qquad \text{Eq. 9}$$

where $c_m$ is the membrane specific capacitance (typically ~1 µf/cm$^2$ for biological cell membranes (see Schanne OF and P. Cerreti ER, *Impedance Measurements in Biological Cells*, John Wiley and Sons, New York, p. 331, 1978.)), d is cell diameter, $\rho_c$ is the resistivity of the intracellular fluid (typically, for cytosol, ~100 Ω-cm), and $\rho_{ps}$ is the resistivity of the medium supporting the cells during PEF treatment (typical range of about 70-500 Ω-cm depending on the ionic strength of the solution). For a typical cell as exemplified by a hematopoietic cell, the maximum charging time constant will be on the order of about 0.5 µs. In preferred embodiments, in order to achieve thorough membrane charging, the duration of the portion of the electric field pulse supplying an electric field strength greater than the critical field strength, $E_c$, to porate the cell, for example the flat-topped portion of a rectangular field pulse, should be at least three to four times the membrane charging time constant $\tau_m$, (i.e., for $\tau_m$~0.4 µs, $\tau_p$>1.6 µs).

After membrane charging is complete, pore formation begins and transport of ionic species between the inside of the cell and the pulsing medium takes place. It is known (Kinosita K and Tsong T Y, Voltage-induced pore formation and hemolysis of human erythrocytes, *Biochim et Biophys Acta*. 471:227-242, 1977 (hereinafter "Kinosita 1977)). that ion transport processes can enhance PEF cell lysis by disrupting the osmotic balance across the cell membrane, which, in turn, can lead to cell swelling and irreversible lysis due to the uptake of water. It is also known (Kinosita 1977) that the efficacy of inducing irreversible cell lysis by PEFs decreases for human erythrocytes when the electric field pulse length is decreased below about 10 µs and improves as the pulse length is increased above 10 µs. This phenomenon probably reflects the need for an electric field pulse duration that is sufficient to allow extensive pore development and time for ion species transport. Based on these observations, reasonable pulse durations for cells having a size range of between about 6 μm and 20 μm, typical for hematopoietic cells, can range from about $\tau_p=2$ μs to about $\tau_p=20$ μs.

PEF cell inactivation and isolation efficacy can also be affected by the total concentration of cells in the PEF treatment volume. The effect of total concentration can be understood by comparing the total electric charge ($Q_m$) required to charge the membranes of all of the cells in the treatment volume to a transmembrane potential of $V_{mc}=1$ Volt, with the charge ($Q_p$) actually supplied to the test volume by the electric field pulse. $Q_m$ can be expressed as:

$$Q_m = \pi v_{TV} \eta_c d^2 c_m V_{mc}/4, \qquad \text{Eq. 10}$$

where $v_{TV}$ is the volume of the PEF treatment cell (cm³), $\eta_c$ is the concentration of cells in the PEF treatment volume (cells/cm³), d is the average diameter of the cells in the PEF treatment volume (assume for purposes of illustration ~10 μm), $c_m$ is membrane specific capacitance (assume for purposes of illustration ~1 μf/cm²), and $V_{mc}$ is the critical transmembrane potential for the onset of irreversible pore formation (assume for purposes of illustration that $V_{mc} \approx 1$ Volt). Note that $Q_m$ is proportional to the cell concentration, $\eta_c$. $Q_p$ can be expressed as:

$$Q_p = \tau_p v_{TV} E/\rho_{ps} w, \qquad \text{Eq. 11}$$

where $\tau_p$ is the electric field pulse length (sec), $v_{TV}$ is the PEF treatment volume (cm³), E is the electric field strength (V/cm), $\rho_{ps}$ is the resistivity of the medium supporting the cells (typically about 70-500 Ω-cm) in the PEF treatment volume, and w is the separation distance between the electrodes in the PEF treatment. Note that $Q_p$ is proportional to the electric field pulse length, $\tau_p$, and inversely proportional to the pulsing medium resistivity, $\rho_{ps}$. If the ratio $Q_m/(Q_m+Q_p)$ is not small, then cell concentration effects can degrade PEF cell inactivation efficacy by significantly increasing the effective charging time scale, $\tau_m$, of the cells in the treatment volume, i.e., a significant amount of the total charge supplied to the treatment volume is required to simply charge the cells. In fact, as this ratio approaches unity, the cell membranes approach the situation where they have just achieved complete charging by the end of the electric field pulse, so there would be essentially no additional time for pore development and transport of ionic species between the cell and the pulsing medium to take place. For best performance, the ratio $Q_m/(Q_m+Q_p)$ is preferably within the range of about $0.0004 \leq Q_m/(Q_m+Q_p) \leq 0.74$. The ratio $Q_m/(Q_m+Q_p)$ can be kept constant as the cell concentration ($\eta_c$) is increased by increasing the pulse length ($\tau_p$) proportionally and/or by appropriately reducing the pulsing medium resistivity ($\rho_{ps}$), for example by increasing the ionic strength. The upper limit of cell concentration given in Table 4 ($\eta_c=10^8$ cells/ml) has significance relative to a clinical PEF tumor cell purging system embodiment. For example, one liter of bone marrow, which is the approximate volume harvested for autologous transplants, contains approximately $10^{10}$ mononuclear cells, which must be purged before transplantation. If PEF conditions can be defined that provide high PEF tumor cell inactivation efficacy for a treatment volume cell concentration of $10^8$ cells/ml, then a 100 ml PEF treatment volume, or a flow-through system able to process 100 ml of cell suspension, can be used to process the entire bone marrow specimen, such a system is reasonable both in terms of system size and electric field pulse energy requirements.

In addition to the nature of the applied PEF, the medium within which cells are suspended can be a significant factor in the performance and efficacy of the invention. The pulsing medium, in which biological cells are suspended, in some embodiments can have an osmolality that preserves the osmotic balance between the intracellular and intercellular fluids, in other words isotonic, where isotonic defines a solution with an osmotic strength (osmolality) similar to that of the suspended cells so that the cells do not undergo substantial osmotic pressure-driven cell volume regulation (~300 mOsm/kg-water for many mammalian cells, such as hematopoietic cells). If the osmotic strength of the pulsing medium differs substantially from that of the cytosol of the cell, the cell can undergo changes in cell volume, such as shrinkage or swelling that can be detrimental to cell viability and the performance of the inventive method, especially for isolations based on characteristic cell size. In some embodiments however, it can be desirable to suspend a cell suspension in a somewhat hypotonic medium either prior to pulsing, with subsequent pulsing performed in isotonic medium, or during the PEF treatment itself. In these embodiments, the suspending medium should have an ionic strength selected to enable at least one cell type in the suspension to undergo osmotic swelling, while not being low enough to cause rupture or a substantial loss of viability to target cells within the time frame of the treatment. Pre-treatment, or PEF treatment using a hypotonic suspending fluid can potentially improve performance for certain cell isolations by causing cells to become larger and more spherical in shape, and thus potentially more sensitive to the effects of an applied electric field. Treating cell suspensions that are characterized by cells having a more uniform spherical shape can also improve performance by reducing the effects of cell orientation within the electric field on poration.

The ionic strength of the pulsing medium can be altered, while preserving the desired osmolality, by combining a solution comprising one or more solubilized electrolytes having a desired osmolality (e.g. an isotonic saline solution) with a solution comprising one or more solubilized non-electrolytes having a desired osmolality (e.g. an isotonic sucrose solution). There are several reasons why, for some embodiments, it can be desirable to reduce the ionic strength of the pulsing medium from standard physiological conditions (e.g. equivalent to a 0.15 M NaCl aqueous solution for many mammalian cells, such as hematopoietic cells). One reason is that it has been shown (Kinosita 1977) that PEF treatment using a pulsing solution having a below-physiological ionic strength followed by resuspension of PEF-treated cells in a standard physiological ionic strength solution can enhance cell destruction by colloidal osmotic lysis and result in a more rapid and extensive irreparable lysis of erythrocytes (red blood cells). This phenomenon has also been observed in the context of the present invention with leukocytes (white blood cells), where the PEF porated cells were subsequently reduced to small cell fragments by PEF treatment in low ionic strength medium (e.g. 10 v % PBS, 90 v % isotonic sucrose) followed by exposure to a physiological strength medium (e.g., isotonic PBS or Iscove's Modified Dulbecco's Medium (IMDM)). For embodiments of the inventive method utilizing a relatively lower ionic strength pulsing medium followed by exposure to a relatively higher ionic strength medium, the particular ionic strengths chosen for the pulse and post-treatment medium, and the exposure time of the PEF-treated cells in the post-treatment buffer will be selected based on routine experimentation with the particular cell suspension of interest to determine the conditions that yield the highest levels of inactivation of undesired cells with the best preservation of the viability of desired cells. Typically, the post-treatment medium will have an ionic strength similar to the physiological ionic strength of the cells in the treated suspension and the pulse medium will have an ionic strength ranging between 10% and 90% that of the post-treatment medium. The exposure time of the cells to the post-treatment medium can vary from a few seconds to an essentially indefinite period. It is important, however, that sufficient time be allowed for adequate diffusion and colloidal osmotic lysis to take place. In addition to, or instead of, having an ionic strength that is higher than that of the pulsing medium, the post-treatment medium may for some embodiments, have a higher osmolality than the pulsing medium and/or contain an agent that causes or enhances irreparable lysis of porated cells, such as, in some preferred embodiments, calcium ions. For some embodiments including a post-treatment step after PEF treatment designed to enhance or cause irreparable cell lysis, the cells porated by PEF exposure undergo irreversible poration of the cell membrane during PEF treatment, and post-treatment, as described, functions to irreparably lyse the cells that have already been inactivated by the PEF exposure. In other embodiments, exposure to the PEF porates, but does not necessarily irreversibly porate, the membranes of the cells to be inactivated, with inactivation and/or irreparable lysis occurring during a post-treatment inactivation step.

For some embodiments, it may be desirable to remove any inactivated cells, lysed cells, and cellular debris from PEF treated specimens. Small cell fragments and debris generated by cell rupture during irreparable cell lysis can be separated from the viable cells using a variety of techniques known in the art, for example single- or multi-gradient centrifugation techniques. For embodiments where PEFs or post-treatment can fragment affected cells, it is possible to separate viable cells from cellular debris using standard gradient density centrifugation techniques. For example, Ficoll-Paque gradient density centrifugation, which is a single gradient separation scheme can be used. Multi-gradient centrifugation can also be used for other applications as apparent to one of skill in the art. For embodiments where inactivated cells also undergo irreparable cell lysis, characterized by cell rupture, it can also be advantageous to add to the suspending medium an agent that is able to degrade cellular debris. A variety of such agents apparent to one of skill in the art can be employed to reduce the cellular debris to its molecular components. Particularly preferred are enzymatic agents, and especially preferred is DNase to breakdown DNA dispersed in the pulsing media, and trypsin digestion to breakdown cell membrane and proteinaceous material. Such agents may be present during the PEF treatment, or alternatively, may be added subsequent to PEF treatment.

Other advantages to reducing the ionic strength of the pulsing medium for some embodiments are related to the increased resistivity and reduced conductivity of pulsing solutions having a reduced ionic strength. The power density $W_p$(J/cm$^3$) and total charge density Q (Coulomb/cm$^3$) input into the PEF treatment volume are both functions of the resistivity of the pulsing medium:

$$W_p = E^2 \tau_p / \rho_{ps} \qquad \text{Eq. 12}$$

$$Q = E \tau_p / \rho_{ps} \qquad \text{Eq. 13}$$

where E is the magnitude of the applied electric field, $\tau_p$ is the pulse duration, and $\rho_{ps}$ is the resistivity of the pulsing medium. The resistivity of the pulsing medium varies inversely with ionic strength. Thus, according to Eq. 12, energy and power requirements of a PEF treatment cell can be reduced by a factor of ten, for example, by using a mixture of 10% by volume aqueous isotonic phosphate buffered saline and 90% by volume aqueous isotonic buffered sucrose as a pulsing medium instead of a standard physiological ionic strength medium. Additionally, reducing the ionic strength of the pulsing medium increases the resistance of the PEF treatment volume, which, for a given electric field strength and pulse duration, reduces the electron charge driven through the PEF treatment volume as shown by Eq. 13. Undesirable electrochemical reactions, such as free radical production, are typically proportional to the charge driven through the PEF treatment volume. Thus, reducing the ionic strength of the pulsing medium can proportionally decrease the production of free radicals, or other undesirable by-products of electrochemical reactions. Reduction of electrochemical reactions occurring in the PEF treatment volume during treatment can also reduce the pH swing of the pulsing medium during pulsing and also reduce the production of chlorine and hydrogen bubbles. Formation of bubbles during treatment is very undesirable, since the presence of bubbles can lead to non-uniform field distribution within the treatment volume and locally elevated electric field intensities, which can significantly reduce the size selectivity of the inventive cell isolation methods. In general, it is desirable to maintain the pH of the pulsing medium relatively constant during PEF treatment and within a range that is not detrimental to the viability of the cells being treated (typically about pH 7-7.6). A variety of buffer systems apparent to one of skill in the art for use in this range that are sufficiently non-toxic to cells can be employed including, but not limited to phosphate buffers, BES, MOPS, TES, HEPES, DIPSO, and TAPSO. Preferred for embodiments where precise pH control is especially important, are buffer systems including one or more strong organic buffers such as those referred to as "Good" buffers (Good, N. E., et al., *Biochemistry*, 5:467(1966); Good, N. E., and Izawa, S., *Meth. Enzymol.*, 24(Part B):53(1972); Ferguson, W. J. and Good, N. E., *Anal. Biochem.*, 104:300(1980)), and especially N-[2-Hydroxyethyl]piperazine-N'-[2-ethanesulfonic acid] (HEPES).

One important consideration in designing and implementing a PEF isolation or inactivation strategy is heat effects and temperature rise due to heat generated within the PEF treatment cell due to the energy deposited into the treatment cell by the electric field. One issue that depends heavily on heat transfer effects is whether the total exposure time of the treated suspension should be achieved with a single pulse or with a series of pulses. Since many biological cells can be non-selectively inactivated by overheating, which is not a function of electroporation threshold, and since a single long electric field pulse can, without sufficient heat removal, cause a greater amount of heating of the cells for a given total exposure time, it is preferable, for many embodiments, to apply the total electric field exposure time as a series of pulses, rather than as a single pulse of longer duration. Since cyclic heating and cooling is particularly destructive for blood cells, pulse duration should be kept short enough to minimize cell and cell suspension temperature excursions beyond the physiological range. The rate, or frequency, at which electric field pulses may be applied is related to the energy deposited in the pulsing medium per electric field pulse (Joule heating), the geometric shape and heat transfer characteristics of the particular PEF treatment volume and the density and thermal conductivity of the pulsing medium (which collectively dictate heat removal rates), and the heat capacity of the pulsing medium. There are two components to the total temperature rise in the PEF treatment volume as a function of the electrical energy input: the temperature jump $\Delta T_f$(° C.) that occurs for each individual electrical pulse; and the steady pulsing temperature rise $\Delta T_s$(° C.), which is a function of the volume and heat transfer characteristics of the PEF treatment cell. Each time a pulse is applied to the pulsing medium, the temperature will jump. The magnitude of the temperature jump is proportional to the power density $W_p$ given by Eq. 12, and can be expressed as:

$$\Delta T_J (°C.) = \tau_p E^2 \Phi_{pm} \rho_{ps} c_p, \quad \text{Eq. 14}$$

where $\Delta T_J$ is the temperature jump (° C.), $\tau_p$ is the electric field pulse length (with a typical range for cell isolations involving hematopoietic cells of about for example 2-20 μs), E is the electric field strength (with a typical range for cell isolations involving hematopoietic cells of about for example 0.5-5 kV/cm), $\Phi_{pm}$ is the density of the pulsing medium (typically ~1 g/cm³), $\rho_{ps}$ is the resistivity of the pulsing suspension (with a typical range for cell isolations involving hematopoietic cells of about for example 70-500 Ω-cm), and $c_p$ is the specific heat of the pulsing medium (typically ~4.19 J/g ° C.). Under the most extreme conditions presented in Table 4, and listed in parenthesis directly above, the maximum temperature jump per electric field pulse will be $\Delta T_J \approx 0.86°$ C. The steady temperature rise is a function of the heat input per pulse, the number of pulses per unit time (frequency), and the heat transfer rate of the PEF treatment cell tending to remove heat from the treatment volume. One dimensional conduction heat transfer considerations may be applied for the static PEF treatment cell embodiment to determine the steady pulsing, time average temperature rise at the midplane between the electrodes imparting the electric field to the treatment volume relative to the temperature of the bounding electrodes. This formulation assumes that convective transport driven by temperature induced density gradients are of negligible importance. Equation 14a below (see Holman J P. *Heat Transfer*, 5th Ed., McGraw-Hill, Inc., New York, 1981, p. 35) describes the average temperature rise for one dimensional steady pulsing volumetric heat deposition by PEFs into a treatment volume bounded by two plane electrodes.

$$\Delta T_{Cl, ave} = q w^2 / 8\kappa \quad \text{Eq. 14a}$$

Where q is the volumetric heat deposition rate given by:

$$q = F \tau_p E^2 / \rho_{ps} \quad \text{Eq. 14b}$$

And where w is the separation distance between the electrodes, κ is the thermal conductivity of the pulsing medium, F is the pulse repetition frequency, $\tau_p$ is the electric field pulse length, E is the strength of the imposed electric field, and $\rho_{ps}$ is the resistivity of the pulsing medium. Equations 14a and 14b indicate that the mid-plane temperature increases as the square of the electrode separation distance, linearly with pulse repetition frequency, the square of electric field strength, and inversely proportional to the resistivity of the pulsing medium. Since the average midplane temperature rise given by Eq.'s 14a and 14b, which constitutes the maximum average temperature rise in the PEF treatment volume, is inversely proportional to the resistivity of the pulsing medium, an increase in pulse repetition frequency by a factor of ten can be realized while maintaining the same midplane temperature rise by increasing the pulsing medium resistivity by a factor of ten. This can be accomplished by decreasing the ionic strength of the pulsing medium to 10% of standard physiological ionic strength by the methods described previously. The temperature jump given by Eq. 14 in response to the application of each electric field pulse can be imagined to be superimposed on the average steady pulsing temperature rise $\Delta T_{Cl, ave}$ as a periodic temperature spike with an exponential decay and a frequency corresponding to electric field pulse repetition frequency.

For illustrative purposes, if the electrode spacing is 0.318 cm and using the most extreme conditions presented in Table 4, which gave a maximum temperature jump per electric field pulse of $\Delta T_J = 0.86°$ C., the steady pulsing temperature rise at the midplane between the two electrodes will be $\Delta T_{Cl, ave}$(° C.)=5.16 F (Hz). Thus, if the electrodes are maintained at a temperature of 25° C. and one wishes not to exceed a midplane peak temperature no greater than 37° C., then the average midplane temperature cannot exceed $\Delta T_{Cl, ave}$=37−25−$\Delta T_J$, which is $\Delta T_{Cl, ave}$=11.14° C., which constrains the pulse repetition frequency to be no greater than F=11.14/5.16=2.16 Hz. If the ionic strength of the pulsing medium was reduced by a factor of ten, the pulsing medium resistivity would increase by a factor of ten, which would allow operating at a pulse repetition frequency of 21.6 Hz for which $\Delta T_{Cl, ave}$ would remain at 11.14° C.

For illustrative purposes, assuming a worst-case heating situation by neglecting any PEF treatment volume heat removal effects, the total electric field exposure time (t=$N_p \tau_p$, where $N_p$ is the number of applied electric field pulses) that may be applied without exceeding a predefined pulsing medium temperature rise can be expressed as:

$$t = \Phi_{pm} \rho_{ps} c_p \Delta T_{max} / E^2, \quad \text{Eq. 15}$$

where $\Delta T_{max}$ is the maximum predefined allowable temperature rise (° C.). For example, if pulsing is initiated with a PEF treatment cell pulsing medium temperature of 25° C. and we wish not to exceed a final pulsing medium temperature of 37° C., then the predefined maximum allowable temperature rise is $\Delta T_{max}$=12° C. Based on $\Delta T_{max}$, and the strength of the applied electric field the allowable total electric field exposure time for a given cell suspension in a PEF treatment cell can be determined by Eq. 15. Eq. 15 also shows that if a low ionic strength pulsing medium is used, the allowable electric field exposure time calculated for a given $\Delta T_{max}$ is directly proportional to the decrease in ionic strength; for example, reducing the ionic strength by a factor of ten would increase the allowable exposure time by about a factor of ten. Furthermore, since under low ionic strength conditions, the energy transferred to the PEF treatment volume is reduced, for a given desired total exposure time, the pulse frequency may be increased without exceeding the predefined maximum temperature rise, thus allowing for a more rapid isolation or inactivation. Accordingly, the inventive PEF strategy can be a very rapid approach to cell purging and cell isolation.

For a single- or multi-pass flow-through PEF treatment cell embodiment of the invention, Eq. 15 can be manipulated to a form that describes the temperature rise of a fluid element of the pulsing medium as it traverses from the inlet to the exit of the PEF treatment volume. This formulation represents an upper bound on the temperature rise since it neglects heat transfer to the bounding electrodes as the fluid element passes through the PEF treatment volume. If $N_p$ is the number of electric field pulses applied during the residence time of the pulsing medium in the PEF treatment volume and $\tau_p$ is the duration of each of the electric field pulses, then the total electric field exposure time is t=$N_p \tau_p$ and the resulting temperature rise is given by Eq. 15a below:

$$\Delta T_{res} = t E^2 / \Phi_{pm} \rho_{ps} c_p \quad \text{Eq. 15a}$$

As illustrated above for the static PEF treatment cell embodiment, reduction of the ionic strength of the pulsing medium, which results in an increase in the resistivity of the pulsing medium, can allow a corresponding increase in the number of pulses that can be applied during the residence time of the pulsing medium in the PEF treatment volume. Thus, for the flow-through PEF treatment cell embodiment, it can be beneficial to use the lowest ionic strength pulsing medium allowable in order to maximize the number of pulses that may be applied in a single pass without exceeding the temperature rise limitations beyond which thermal effects impact cell viability. The relationships given above provide guidance to the skilled practitioner for selecting reasonable pulse repetition frequencies that are appropriate, for a specific pulsing medium and electric field pulse intensity and duration, for inactivating selected cells from a cell suspension having a maximum allowable temperature rise.

Another previously mentioned factor that can influence the way in which an applied electric field interacts with a cell suspension, and the selectivity of an applied electric field at inactivating cells based on a critical electroporation threshold, is the shape and orientation of cells within the field. This factor is important for any cell inactivation involving non-spherical shaped cells. A problem arises with such samples because non-spherical cells, in a given sample, are typically randomly aligned with respect to the electric field direction. While such a random alignment is not a problem for hematopoietic stem cells or other essentially spherical cells, random orientation can reduce the effectiveness, especially for cells with large aspect ratios, of cell inactivation with applied electric fields. Eq. 1 shows that the transmembrane voltage, $V_m$, that results from an applied electric field E is directly proportional to the projected length, l, of the cell in the electric field direction. Thus, for cells with large aspect ratios, l can be highly variable depending on the orientation of the cell. Since it is typically desirable to apply an essentially time-invariant transmembrane voltage for a predetermined length of time in order to obtain more easily predictable and controllable poration results, it is therefore desirable to align cells that are not substantially spherical so that they have a more consistent and predictable orientation with respect to the electric field direction. For embodiments of the invention where it is desired to align the axes of cylindrical or oval shaped cells to achieve maximum PEF inactivation efficiency, an AC field can be applied across the sample to accomplish this function. The AC field is preferably selected to provide an essentially uniform oscillating electric field during the PEF treatment period, and has a magnitude selected to be sufficient to align the cells with their long dimensions parallel to the PEF field direction for optimum size selectivity by the PEF field, without porating the cells or unduly overheating the pulsing medium. The theoretical treatment of this cell alignment technique is discussed in detail by Lynch (Lynch P T and Davey M R. *Electrical Manipulation of Cells*, Chapman and Hall, New York, Chapter 4, 1996), herein incorporated by reference.

Some preferred embodiments of the invention include the use of an applied electric field for cell inactivation that is a bipolar electric field. A "bipolar electric field" as used herein refers to an electric field that is pulsed or otherwise applied to a sample so that the average current across the sample over the total treatment time is essentially zero. The use of bipolar electric fields in the context of the present invention provides several advantages over non-bipolar fields. When an electric field is applied across a sample, particularly a blood sample, electrochemical reactions can occur which can produce free radicals, other deleterious compounds, and species that can shift suspension pH and/or generate bubbles. Such electrochemical effects are, as previously indicated, undesirable. Within the context of the present invention, the inventors have found that undesirable electrochemical effects can be reduced or eliminated by utilizing a bipolar electric field pulsed so that the average current across the sample over the treatment time is essentially zero. Because the application of the bipolar electric field involves essentially equal current flows across the sample for each applied polarity, the reversible electrochemical reactions induced by the applied electric field component having a first polarity, can be substantially reversed by the applied electric field component having the opposite polarity, thus yielding a situation characterized by no net electrochemical reaction over the treatment time.

There are a variety of ways to apply a bipolar electric field to the sample as apparent to one skilled in the electrical engineering arts. For some embodiments, the pulses across the sample are of essentially equal magnitude, duration, and number, but alternate pulses are of opposite polarity, while for other embodiments, the pulse having a first polarity may be of greater magnitude but shorter duration while the pulse of the reverse polarity is of lower magnitude and longer duration, so that the total average current flow is essentially zero. In another embodiment, an electric field pulse having a first polarity is utilized together with a DC current having an opposite polarity selected so that the magnitude and duration of each is selected to yield an essentially zero net current in order to achieve no net electrochemical reaction within the sample. In yet another embodiment for creating a desired bipolar electric field, the pulse used to create the PEF field may also be utilized to charge a suitable capacitor. When the original PEF pulse terminates, the capacitor then discharges back through the solution containing the cells at a rate determined in part by a resistance in the discharge path to produce the desired bipolar field.

In addition to reducing undesired electrochemical reactions, bipolar PEFs can provide an additional advantage in the selective inactivation/lysing of larger cells. The additional advantage lies in that the first pulse component having a first polarity results in a charge across the membrane of the cell which remains for some period of time after the first pulse component terminates. If a second pulse component having an opposite polarity is applied across the cell during this time, the voltage across the cell can be effectively doubled for a short period of time. This doubling effect is greater for larger cells than for smaller cells because of the larger membrane charging time scale for larger cells (see Eq. 9). This effect can potentially enhance size-selective destruction of the larger cells, thereby enhancing the cell selectivity of the invention for certain applications.

Temperature may also be utilized to enhance cell inactivation by the inventive methods. In general, biological cells are less capable of repairing membrane damage at sub-physiological temperatures. This behavior can be utilized to increase inactivation of cells in response to an applied electric field. For example, in one embodiment the cells are subjected to a PEF in a solution that is maintained within a physiological range of temperatures (for most mammalian cells, approximately 33-39° C.), the porated cells are then resuspended in a solution at a lower temperature, for example room temperature (approximately 25° C.) or lower, but above the freezing temperature of the suspension. The lower temperature solution delays repair of porated membranes and thus can increase the degree of cell inactivation by colloidal osmotic lysis.

Alternatively, since cell repair (i.e. the closing of pores in a porated cell) will not take place when the cell temperature is dropped much below body temperature, the PEF exposure itself can be performed at a lower temperature, thereby permitting irreversible poration to occur at an electric field strength that can be lower than that which would otherwise be required. In addition, utilizing a lower PEF subjecting temperature for any given applied electric field strength can improve the kill rate (i.e. reduce the surviving fraction) from that suggested by Eq. 8 as determined for the same given field strength but a higher PEF subjecting temperature.

For embodiments of the invention involving applications where it is desired to selectively inactivate one or more cell types having a characteristic size greater than a predetermined value while simultaneously leaving substantially viable another desired cell type, or group of cell types, having a characteristic size below the predetermined value, the greater the difference between the predetermined value of size and the characteristic size of the desired cells, in general, the easier and more selective the isolation. "Substantially viable" as used herein indicates that at least about 10% of the cells in the population are viable, preferably at least 50%, more preferably at least 90%, and most preferably at least 95%, while conversely, "substantially non-viable" as used herein indicates that at least about 25% of the cells in the population are non-viable, preferably at least 75%, more preferably a least 90%, more preferably at least 95%, and most preferably essentially all of the cells in the population are non-viable. For applications where the difference in characteristic size of the desired cell type and the undesired cell type is small, a variety of strategies can be utilized to improve the performance of the PEF isolation protocol. One method is to remove the cells that are close in size to the desired cells by performing a preliminary cell separation step that separates cells on some basis other than a difference in size. Depending upon the particular application, suitable cell separation methods include but are not limited to: flow cytometry; affinity cell chromatography; and centrifugation.

For example, in an application involving the isolation of hematopoietic stem cells from other blood or bone marrow cells, both red blood cells (about 7 µm diameter) and resting lymphocytes (about 7 µm diameter) are dimensionally the closest to the stem cell (about 6 µm diameter). Because the number of red blood cells is much greater than the number of all of the nucleated cells combined, and because the red cells have a higher density than the nucleated cells, they are typically separated from a sample by density gradient centrifugation, using for example a Ficoll-Paque single gradient having a density of 1.07 g/cm$^3$ (which will also remove polymorphonuclear leukocytes such as neutrophils), before PEF application. If the size selectivity of the PEF isolation for a particular embodiment is not sufficient to select stem cells over the resting lymphocytes with the desired level of purity, the resting lymphocytes, or other small cells, can be removed from the pulsing medium prior to PEF treatment. This can be achieved, by a variety of cell separation methods known in the art including CD34 targeted antibody affinity binding techniques that are selective for CD34$^+$ cells, such as hematopoietic precursor cells including some stem cells. An alternative is to add an agent to the cell suspension that can preferentially modify (increase or decrease) the critical electroporation threshold of a subset of the cells to make them more or less susceptible to inactivation by electric fields. For example in one embodiment, the small resting cells, such as resting lymphocytes, may be eliminated by activating the resting lymphocytes using an agent that forces the resting lymphocytes into their active state so as to achieve their mature size (typically about 12 µm) where they can be more easily inactivated without adversely affecting the stem cell population. A variety of suitable activating agents are known in the art including protein agents, such as cytokines, lymphokines, chemokines, anti-cell surface marker antibodies, and cell receptor antagonists. Other suitable stimulants include lectins, such as Phaseolus vulgaris lectin (PHA), and concanavalin A. As specific examples, monoclonal anti-CD40 antibody, CD40 ligand, or interleukin-4 (IL-4) can efficiently activate resting B-cells (see Valle A, Zuber C E, Deffrance T, Djsou, et al., Activation of human B lymphocytes through CD40 and Interleukin 4. *Eur J Immuno* 19:1463-1467, 1991. Banchereau J, de Paoli P, Valle A, Garcia E, et al., Long term human B cell lines dependent on Interleukin 4 and anti-CD40. *Science* 251:70-72, 1991. both incorporated herein by reference), while interleukin-2 (IL-2) and concanavalin A can efficiently activate T-cells (Berger S L, Lymphocytes as resting cells. *Methods in Enzymology*. (eds) Jakoby W and Pastan I. Academic Press. Vol LVIII:486-494, 1979. Waxman J and Balkwill. (eds) Interleukin-2. Blackwell Science Publications, Oxford, 1992. both incorporated herein by reference).

Another factor that can affect the performance of selective cell inactivation by electric fields on the basis of a difference in a characteristic electroporation threshold based on cell size is a concurrent difference in the dielectric membrane breakdown voltage, for example, due to a difference in the effective membrane thickness, between cell types. In such cases, it can be advantageous to add an agent to the cell suspension, prior to or concurrently with electric field application, that can modify (increase or decrease) the dielectric membrane breakdown voltage of one or more cell types. For example, for applications where a larger, undesirable cell type possesses a thicker effective membrane thickness than a smaller desired cell type, as previously discussed, the larger cell having the thicker effective membrane thickness will typically have a higher critical dielectric membrane breakdown voltage and thus require a larger electric field strength for inactivation than a comparably sized cell having a thinner membrane. Depending on the difference in characteristic size and effective membrane thickness between the two cell types, the ability of the electric field to selectively porate the larger cells while not affecting the smaller cells can be diminished or eliminated. A specific example of an application where this phenomenon may arise is in the use of PEFs for selectively inactivating certain tumor cells from tissue samples or hematopoietic cell suspensions. A variety of tumor cells, for example many epithelial tumor cells, have associated with their plasma membrane a relatively thick layer of mucopolysaccharide, known as the glycocalyx, that can increase the effective thickness of the membrane dielectric layer making the cells less susceptible to the PEF. For applications where this phenomenon is an important consideration, e.g. when cell kills are substantially less than would be predicted based on cell size alone, the performance of the PEF method can be improved by removing the glycocalyx layer prior to subjecting the cell suspension to the PEF treatment. Agents that can be used for effectively reducing or eliminating the glycocalyx layer on cell membranes include enzymes such as hyaluronidase, collagenase, pronase, elastase, and trypsin (Gruenert D C, Basbaum C B, and Widdicombe J H. Long-term culture of normal and cystic fibrosis cells grown under serum-free conditions, *In Vitro Cell. Dev. Biol.* 26, 411-418, 1990. Lechner J F, Babcock M S, Marnell M, Narayan K S, and Kaighn M E. Normal human prostate epithelial cell cultures, *Methods in Cell Biology*, 21B, 195-225, 1980. Stamfer M R. Isolation and growth of human mammary epithelial cells, *Journal of Tissue Culture Methods*, 9, 107-115, 1985.). Alternatively, an agent that preferentially increases the dielectric membrane breakdown voltage of a desired cell type could be used, in addition to or instead of the above mentioned agents, in some embodiments to make the cells less susceptible to inactivation by electric fields.

In some embodiments, where it is desired to alter the apparent membrane breakdown voltage or characteristic size of one or more subpopulations of cells in a heterogeneous population of cells, for example when the electroporation thresholds of desirable and undesirable cellular subsets are comparable, such alterations can be effected by attaching material to cellular subsets using antibodies that have immunospecificity for the cells, especially monoclonal antibodies. For example, metallic beads coated with a monoclonal antibody that can bind the bead to a specific cell surface antigen can produce two distinctly different effects depending upon the surface density of the beads attached to the cell. If the surface density of the attached beads is very high, such that an almost continuous layer of metallic beads exists on the surface of the cell, then the resulting metallic structure will behave as a Faraday cage, which will shield the cell from the effects of the imposed electric fields. If the surface density of the beads on the cells is low, however, then the each bead will behave as an antenna, which can make the effective size of the cell larger, thereby making the cells more susceptible to the lethal effects of the imposed electric fields than implied by the original size of the cell. Thus, agents, such as antibody coated metallic beads, can be used to alter the electroporation thresholds of specific cells, thereby enhancing PEF selection or inactivation characteristics.

A typical stem cell, shown in FIG. 2a, also possess a unique morphology that can make them less susceptible to poration by electric fields than their size would suggest. Morphologically, stem cells are typically small in size (~6 μm in diameter for hematopoietic stem cells) with a faint halo of cytoplasm 72 between the nuclear sack 74 surrounded by nuclear membrane 73, and outer (plasma) membrane 71. The next larger nucleated hematopoietic cells, resting lymphocytes (~7-8 μm in diameter), typically have a much larger gap between their nuclear and outer membranes. The arrangement of the stem cell's nuclear 73 and outer membranes 71 being separated by a very small distance can cause the nuclear 73 and outer membrane 71 to become electrically coupled and to charge together as one effective dielectric layer of thickness approximately equal to the sum of the thicknesses of the nuclear and outer membranes. Provided the electric field pulse length is small compared to the discharge time scale of the nuclear membrane, electric field strengths considerably greater than the value implied by the diameter of the stem cell and the critical transmembrane voltage, $V_{mc}$, for the outer membrane 71 will be needed to form temporary or irreversible pores in stem cells. Specifically, for PEF pulse durations less than the characteristic discharge time scale of the nuclear membrane 73, the critical electric field required for the onset of poration would be:

$$E_{coup} \approx E_c(t_{om}+t_{nm})/t_{om} \qquad \text{Eq. 16}$$

where $E_{coup}$ is the required electric field strength to porate the cell for electrically coupled nuclear 73 and outer 71 membranes, $E_c$ is the critical field strength as calculated from Eq. 7, $t_{om}$ is the effective thickness of the outer membrane 71, and $t_{nm}$ is the effective thickness of the nuclear membrane 73.

FIG. 2b illustrates electrically the reasons the nuclear and outer membranes of the stem cell can charge as one membrane when the electric field pulse duration is small compared to the discharge time scale of the nuclear membrane. The poles 81, 82 of the cell are defined as those two points on the surface of the cell which are closest to the electrodes imposing the electric field. The membrane gap is defined as the smallest distance between the nuclear and outer membranes. The pole-to-pole membrane gap resistance 80 is the resistance in the membrane gap between opposite poles of the cell. The membrane gap resistance 77 is the gap resistance between the inner and outer membranes. When the membrane gap is very small, the membrane gap resistance 77 will be much less than pole-to-pole membrane gap resistance 80. This is typically the case for the stem cell. Under these conditions the nuclear and outer membranes will charge together as one membrane of thickness approximately equal to the sum of the thicknesses of the nuclear and outer membranes. When the gap is significant, which will be the case for most other cells in the blood and immune system, the pole-to-pole membrane gap resistance 80 is less than the membrane gap resistance 77, and the nuclear membrane does not participate significantly in electric field effects, so that just the outer membrane charges. If $R_{pp}$ is taken as the pole-to-pole membrane gap resistance 80 and $C_{pp}$ is the capacitance of the dual membrane system, then the discharge time scale of the nuclear membrane will be no greater than $\tau_{nm} < R_{pp}C_{pp}$. Provided the electric field pulse is significantly less than $\tau_{nm}$, the nuclear and outer membranes will behave electrically as one membrane of thickness equal to the sum of the nuclear and outer membrane thicknesses (see Eq. 16) and during this time, electric field strengths much greater than implied by the diameter of the stem cell (see Eq. 7) will be required to form irreversible pores. This effect can enhance the ability to isolate stem cells utilizing the PEF methods of this invention and can reduce the need to activate cells that are close in size to the stem cells in order to increase the difference in characteristic size.

While the discussion above has been with respect to the poration of larger cells to isolate or segregate stem cells which typically have a smaller size, there are also applications where it may be desirable to porate the stem cells. Heretofore, an effective technique for electroporating stem cells has not existed. Poration of stem cells can be achieved according to the present invention by initially using the PEF method to isolate stem cells, and subjecting the isolated stem cells to an electric field of appropriate magnitude for porating the stem cells. For example, if the electric field pulse duration, $\tau_p$, being utilized is less than $\tau_{nm}$, then the appropriate magnitude would be determined by employing Eq. 16 in combination with Eq. 7; however, if the pulse duration is longer than $\tau_{nm}$, then the appropriate magnitude would be determined by employing Eq. 7. The objective in porating stem cells can be reversible, non-lethal poration or irreversible poration to lyse or kill the cells. One embodiment of the present inventive methods can enable the temporary, reversible poration of the stem cells to allow, for example, genetic material to enter the stem cells, producing genetic mutations or recombinations for gene therapy. The inventive stem cell transfection technique may be preferable to many currently employed techniques, such as using viral transfection, since the PEF poration technique can enable the genetic material to enter a larger percentage of the stem cells and can result in a higher survival rate for the mutated stem cells. Such mutated stem cells can, for example, be utilized in a variety of gene therapy techniques, for cloning, or to provide immunity against specific adverse biological agents such as viruses, bacteria, and various toxins.

Since a variety of known methods exist for extracting viable cells from mixtures containing viable/dead cells and cellular debris, selective inactivation of cells by the methods provided by the present invention represents a potentially important step toward achieving high purity isolation. PEF cell inactivation can, via post-PEF spontaneous cell lysis (colloidal osmotic lysis), transform the PEF inactivated cells into ghost membranes and free nuclei dispersed in the cellular suspension. Single or multiple gradient centrifugation techniques can then be used to separate the viable cells, and, if desired, any residual intact non-viable cells, from the cellular debris composed primarily of ghost membranes and free nuclei. Viable cells can also be extracted from the PEF-treated mixture of viable/dead cells and cellular debris by using cell sorting, e.g. FACS or flow cytometry, or antibody binding strategies that are commercially available for a variety of cell types. Alternatively, if the population of selected viable cells are to be expanded, there may be no need to remove the post-PEF non-viable cells and debris, since the expansion process can produce a post-expansion population of viable cells that will render insignificant the relatively small numbers of inactivated cells and residual cellular debris, or the debris will simply decompose during the expansion culture.

FIG. 3 presents a flow chart summarizing the steps of a typical PEF cell isolation strategy according to the invention. It should be reemphasized that for any given cell suspension and desired cell isolation or inactivation, the PEF parameter values for optimal performance must be selected based on routine experimentation and optimization with guidance from the theoretical development presented previously. The general procedures described below may be employed both during screening tests to determine optimal PEF parameters for cell isolation, and during actual cell selections with predetermined optimal parameters.

Initially, before the beginning of the procedure, PEF operating parameters (e.g. electric field strength, total exposure time, pulse duration and frequency, etc.) are selected as described previously based, in part, upon a difference in a characteristic electroporation threshold difference between desired and undesired cells (determines choice of electric field strength) and a desired degree of cell inactivation (determines choice of exposure time). The first step 61 of the procedure 60 is to prepare the cell suspension. The cell suspension is prepared by uniformly dispersing and suspending cells in a physiologically compatible, conductive medium. In some cases, e.g. blood, the sample to be treated may already be suspended in a suitable medium, in other cases, e.g. cells from solid tissue or organs, the cells may need to be dispersed and resuspended in a suitable medium. The viability, concentration and identity of the cells present in the pre-PEF treated suspension can be determined by a variety of methods known in the art. Viability, for example, for many cells, such as mammalian cells, can be determined by trypan blue dye exclusion. Concentration may be determined by manual or automated cell counting techniques, for example manual counting with a hemacytometer, or automated counting by light scattering techniques. Individual cell types can be enumerated and marked for further tracking by standard immunophenotyping techniques known in the art, such as by using cell-specific dyes or dye-labeled antibodies (e.g. fluorescently labeled antibodies) that have specificity for certain cell surface antigens specific to certain cell types. The labeled cells can then be quantified by standard techniques, for example, fluorescence microscopy or flow cytometry.

The second step 62 of the procedure 60 includes various optional pre-treatment methods, or pre-PEF cell separations, used to enhance the performance of the PEF treatment. A variety of such methods were discussed previously and include: isolation of a subpopulation of cells by cell separation methods such as centrifugation, for example, density gradient centrifugation; osmotic cell lysis of red blood cells; cell affinity chromatography; fluorescence activated cell sorting (FACS); etc. Other treatments that can be employed at this step include treatments designed to enhance a difference in characteristic electroporation threshold, such as: hypotonic swelling of the cells; treatment with an agent to remove a glycocalyx layer from one or more cell types to reduce the effective membrane thickness; treating the cell suspension with an activating agent to increase the characteristic size of one or more cell types, etc. For applications involving the isolation of hematopoietic stem cells from blood or bone marrow, typically during this step, mononuclear cells are purified from the sample from step 1 by using a standard Ficoll-Paque density gradient centrifugation technique, followed by ACK (product 10-548, BioWhittaker, Walkersville, Md.) lysis of residual erythrocytes. The mononuclear cells are then washed and resuspended in an appropriate pulsing buffer. Optionally, an activating agent, such as those mentioned previously, may be added to the suspension to activate resting lymphocytes, or, if tumor cells having a thick glycocalyx layer are present, an enzyme may be added to at least partially remove this layer.

The third step 63 of the method 60 involves subjecting the cell suspension to the pulsed electric field. Electric field strengths and durations may be selected for this step that are sufficient to cause irreversible poration and inactivation of the porated cells, or alternatively, that are sufficient to reversibly porate but not inactivate porated cells. For some purposes, the PEF treated cell suspension produced during this step is in a final, usable form; however, for many applications, additional post-PEF steps are required or desirable for attaining a final cell suspension.

The fourth step 64 of the method 60 is an optional step performed to inactivate cells that are porated but not inactivated in the previous step 63. This step 64 is typically employed for embodiments where the PEF parameters chosen in step 63 are sufficient to porate but not inactivate the undesired cells; however, the step may also be employed for embodiments utilizing PEF conditions selected for inactivation in order to, for example, increase the total fraction of cells inactivated, speed up the inactivation process, or physically disrupt the structure of the inactivated cells by irreversible lysis. As previously discussed, the methods of this step typically involve resuspending the PEF treated cells in an inactivation medium, or adding one or more supplemental agents to the PEF medium to create an inactivation medium in situ, designed to accelerate colloidal osmotic lysis, prevent cell membrane repair, or both. As previously discussed, the inactivation medium for use in this step typically will have one or more of the following properties: a higher ionic strength than the pulsing medium; a higher osmolality than the pulsing medium; a lower temperature than the pulsing medium; or an agent (e.g. $Ca^{++}$) that specifically promotes colloidal osmotic lysis of porated cells.

The fifth step 65 is an optional step performed to remove inactivated cells and cellular debris from the suspension containing viable PEF isolated cells. This step can be performed by a variety of techniques apparent to the skilled artisan, including, but not limited to centrifugation, filtration, and adsorption. In some embodiments, suitable agents may be added in order to break up or reduce cellular debris, such agents including, for example DNase, trypsin, or other enzymes. For applications involving hematopoietic cell isolations, after PEF treatment, the stem cell enriched suspension is typically subjected to a Ficoll-Paque gradient density centrifugation to remove inactivated cells and cellular debris.

For selected applications, it may be desirable to further purify, isolate or treat a subpopulation of cells from the PEF treated cell suspension. Such secondary, or supplemental cell separation or other treatments comprise an optional sixth step 66. Any of the previously mentioned cell separation techniques can potentially be employed for this step. In some cases, the secondary purification may be used to further enrich or purify the subpopulation initially isolated by PEF treatment, while in other cases, the secondary isolation may involve separating a sub-subpopulation of cells from the PEF isolated subpopulation, which sub-subpopulation may not be distinct with respect to a critical electroporation threshold. Such a secondary separation is potentially useful, for example, for applications where it is desirable to separate a particular type of progenitor cell from a PEF isolated stem cell suspension. As previously discussed, preferred stem cell suspensions isolated by PEF can contain a variety of different lineage committed colony forming cells in addition to the pluripotent cells. One or more of these cell sub-types may be isolated by, for example, FACS by utilizing one or more labeled antibodies with immunospecificity to cell surface markers present on particular cell sub-types.

The final optional seventh step 67 comprises any treatments that are performed on or using the PEF treated cell suspensions. Such treatments can include, for example, expansion and/or differentiation of the selected cells by in vitro cell culture techniques, transfection or other genetic modification of selected cells, etc. For example for applications involving the isolation of stem cells, since the fraction of stem cells present in a typical pre-treatment sample is very small (about $1:10^6$ in bone marrow aspirate), depending on the volume of sample processed, the final quantity of isolated stem cells may not be sufficient to engraft a patient (typically about $10^6$ CD34$^+$ cells/kg body weight are required). In such cases, the quantity of stem cells can be amplified through standard stem cell amplification and expansion techniques (Zandstra, A. J., et al. "Advances in hematopoietic stem cell culture," *Curr Opin Biotechnol* 9:146-151(1998)). Cell culture techniques can also be employed to activate the isolated stem cells to differentiate along desired lineage paths, thus increasing the number of committed progenitor cells reinfused into a patient. An additional post-PEF isolation treatment that can optionally be performed on the isolated stem cells, for example for gene therapy applications, is reversible poration and transfection of the cells with genetic material using PEFs to electroporate the stem cells.

In most applications, and especially when screening to determine optimal PEF parameters, it is desirable to characterize the post-PEF treatment cell suspension with regard to cell quantity, cell viability, and cell identity in order to evaluate performance. The techniques described for characterizing the pre-treatment suspensions can also be employed to characterize the post-treatment populations. From comparison of the pre- and post-treatment cell suspensions, yield, selectivity, enrichment, and depletion determinations can be inferred. The inventors have found that for analyzing post-PEF suspensions of hematopoietic cells, an effective and convenient method to simultaneously determine cell viability, cell apoptosis, and cell concentration, and cell identity, is to stain the post-PEF cells obtained after the third step 63 or the fifth step 65 above with a combination of propidium iodide, Annexin-V, and fluorescently labeled antibodies specific to CD3, CD14, CD19, CD45, CD34, and CD38 cell surface markers. These cell specific fluorescently labeled markers allow enumeration of lymphocytes (CD3+, CD45+), monocytes (CD 14+, CD45+), primitive progenitor cells (CD34+), and certain hematopoietic stem cells (CD34+, CD38−). The viability stain propidium iodide is a DNA stain. Thus for cells with disrupted membranes, yet still containing a nucleus, this dye will stain non-viable cells. Annexin-V, however, stains phosphatidylserine (PS) which migrates from the inside to the outside of the plasma membrane during normal apoptosis. Thus it is normally used as an indicator of apoptotic, not yet non-viable cells. Whether or not the PS migrates to the external surface of the cell as a result of PEF treatment is unimportant. What is important is that should PEFs result in the discharge of the nucleus from the cell, Annexin-V will stain the PS on the inside of the plasma membrane, since this stain has access to the inside of the cell due to membrane disruption. Thus, ghost cells should have a bright Annexin-V fluorescence signature. Therefore, gating based on both PI and Annexin-V has been found by the investigators to give the best screening for viable cells. Additional markers specific to cancer cells can also be included for applications involving cancer cell purging.

While the above description in association with FIG. 3 is intended to illustrate some representative methods and strategies for performing the inventive cell isolations, it should be understood that the above description is only illustrative and exemplary, and that the invention can be performed otherwise than described above without departing from the spirit and scope of the invention as presented in the appended claims. Also, the above description presents and describes various methods and techniques that can for certain embodiments and applications be associated with the invention; however, additional or substitute methods may be used as apparent to the skilled artisan, and details and descriptions that, in some cases, may be necessary to perform the invention but that are known or available to those skilled in the art are not necessarily included or described herein.

Figure 4:
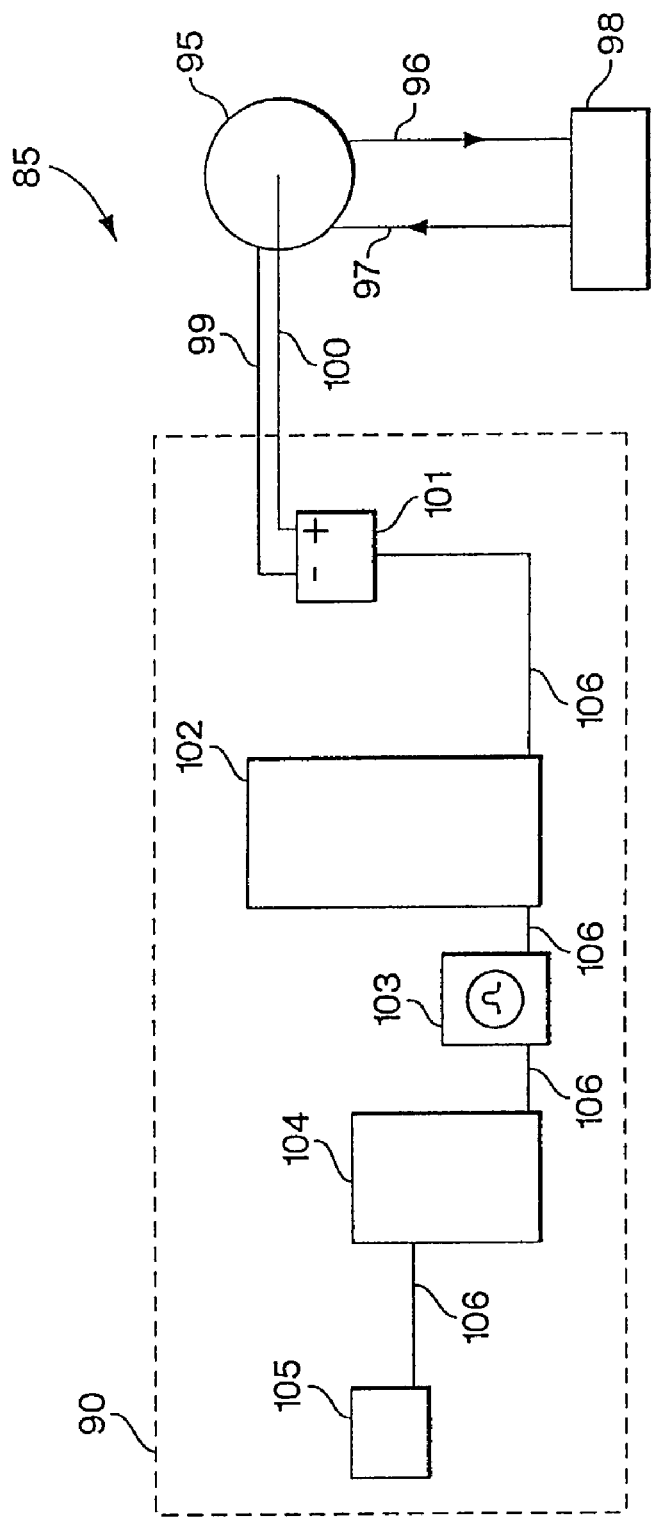
FIG. 4 is a schematic illustration of a batch treatment system according to one embodiment of the invention.

The inventive electric field cell/discrete object isolation/inactivation methods can potentially be performed using a wide variety of electroporation equipment known in the art (see for example: Gene Pulser II, BioRad, CA; ECM-2001, BTX, CA; Multiporator, Eppendorf, NY; Electroporator II, Invitrogen, CA; PA-4000, Cytopulse, MD). Although there are numerous electroporation systems available, they are not ideally suited for cell selection/inactivation discussed herein because they have been designed for electroporation or electrofusion applications for which cell preservation is key, not cell inactivation. They are also typically not capable of processing the number of cells appropriate for either research or clinical implementations of the cell selection/inactivation strategies discussed herein, since they are limited by the electric field pulse energies they can deliver. FIG. 4 shows one embodiment of a batch system 85 including elements useful for performing the inventive PEF methods. The main components of the illustrated system are: an electric field pulse driver 101, which applies voltage pulses to the PEF electrode enclosure assembly 95 (which includes the PEF treatment cell); a power supply 102, which can be external or internal to the pulse driver; an optional oscilloscope 103 for electric field waveform monitoring; a trigger generator 104; and a control/data acquisition system 105, preferably including a computer, for controlling the system and gathering and processing data. The control/data acquisition system 105, trigger generator 104, oscilloscope 103, power supply 102, and pulse generator 101 are electrically coupled via appropriate electrical connections 106, and together comprise an electric field generating mechanism 90. The pulse driver 101 of the generating mechanism 90 is electrically coupled to the PEF electrode enclosure assembly 95 via cathode connecting line 100 and anode connecting line 99. Also included in the overall system 85 is an optional forced circulation cooling system 98 which forces cooling fluid through the PEF electrode enclosure assembly 95 through lines 96 and 97 to remove heat from the treatment cell that is generated by the electric field and for controlling the temperature of the treatment cell.

Figure 5:
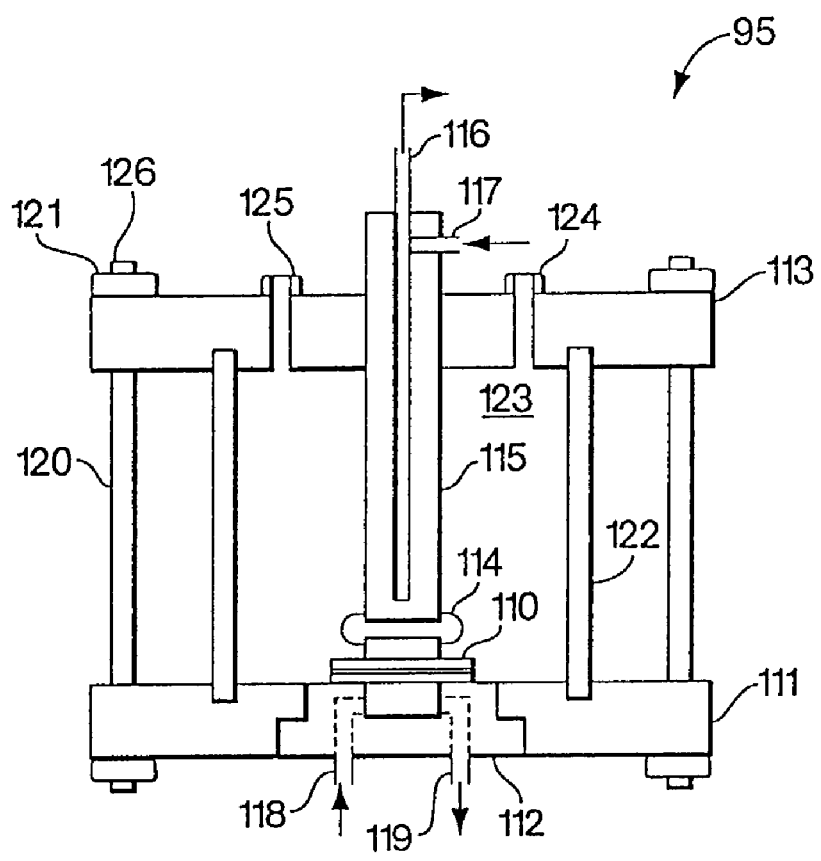
FIG. 5 is a schematic illustration showing a cross-sectional view of an electrode enclosure assembly according to one embodiment of the invention.

The PEF electrode enclosure assembly 95 of system 85 is shown in greater detail in FIG. 5. The electrode enclosure assembly 95 includes a PEF treatment cell 110 that is designed to physically mate with cathode 114 and anode 112. FIG. 5 is a cross-sectional view of the PEF electrode enclosure assembly 95 taken by slicing the PEF electrode enclosure assembly 95, as oriented in FIG. 4, into the plane of the drawing. The PEF electrode enclosure assembly 95 also includes an annular enclosure 122 that is sealingly mated to the top plate 113 and bottom plate 111. Top plate 113 and bottom plate 111 are connected to each other at spaced intervals using a plurality of spacer rods 120 which are transversed by a threaded rod 126 with threadingly attached nuts 121 which may be tightened to securely connect the top 113 and bottom 111 plates, or loosened and removed for disassembly of the PEF electrode enclosure assembly 95. Annular enclosure 122 circumscribes and defines an enclosed space 123 that may be evacuated via evacuation port 125 or pressurized with a gas via pressurization port 124 in order to more thoroughly insulate the electrical components of the assembly. The treatment cell 110 and cathode 114 is supported by a fluid-cooled cathode support rod 115 that includes cooling fluid channels 116 and 117. The anode 112 also preferably includes fluid cooling channels 118 and 119 to provide additional heat removal capacity from the treatment cell 110. The fluid cooling channels are in fluid communication with forced circulation cooling system 98 shown in FIG. 4. Forced circulation cooling system 98 is preferably sized and designed to maintain the cathode 114 and anode 112 at a selected temperature controlled to +/−0.1 degrees C. over a temperature range of at least 4-50 degrees C. Heat removal and temperature control of the pulsing medium is effected by conductive heat transfer from the medium to the temperature controlled anode 112 and cathode 114. The PEF electrode enclosure assembly 95 should be constructed with appropriate seals so that enclosed space 123 can be maintained under high vacuum without significant leakage. The PEF electrode enclosure assembly 95 can be constructed from a variety of materials apparent to one of skill in the art. The anode assembly 112, and cathode 114, should be constructed from conducting materials such as metals. In one particular embodiment, the cathode 114 and anode 112 are constructed of copper. In some preferred embodiments, anode assembly 112 is removable from bottom plate 111 to allow easy access and removal of test cell 110 without the need to disassemble the entire PEF electrode enclosure assembly 95. The top 113 and bottom 111 plates can be constructed of any strong stiff material. Preferred plates are constructed from an insulating material such as a strong plastic, for example Lexan. Annular enclosure 122 is preferably constructed from a transparent material such as plexiglass.

Figure 6:
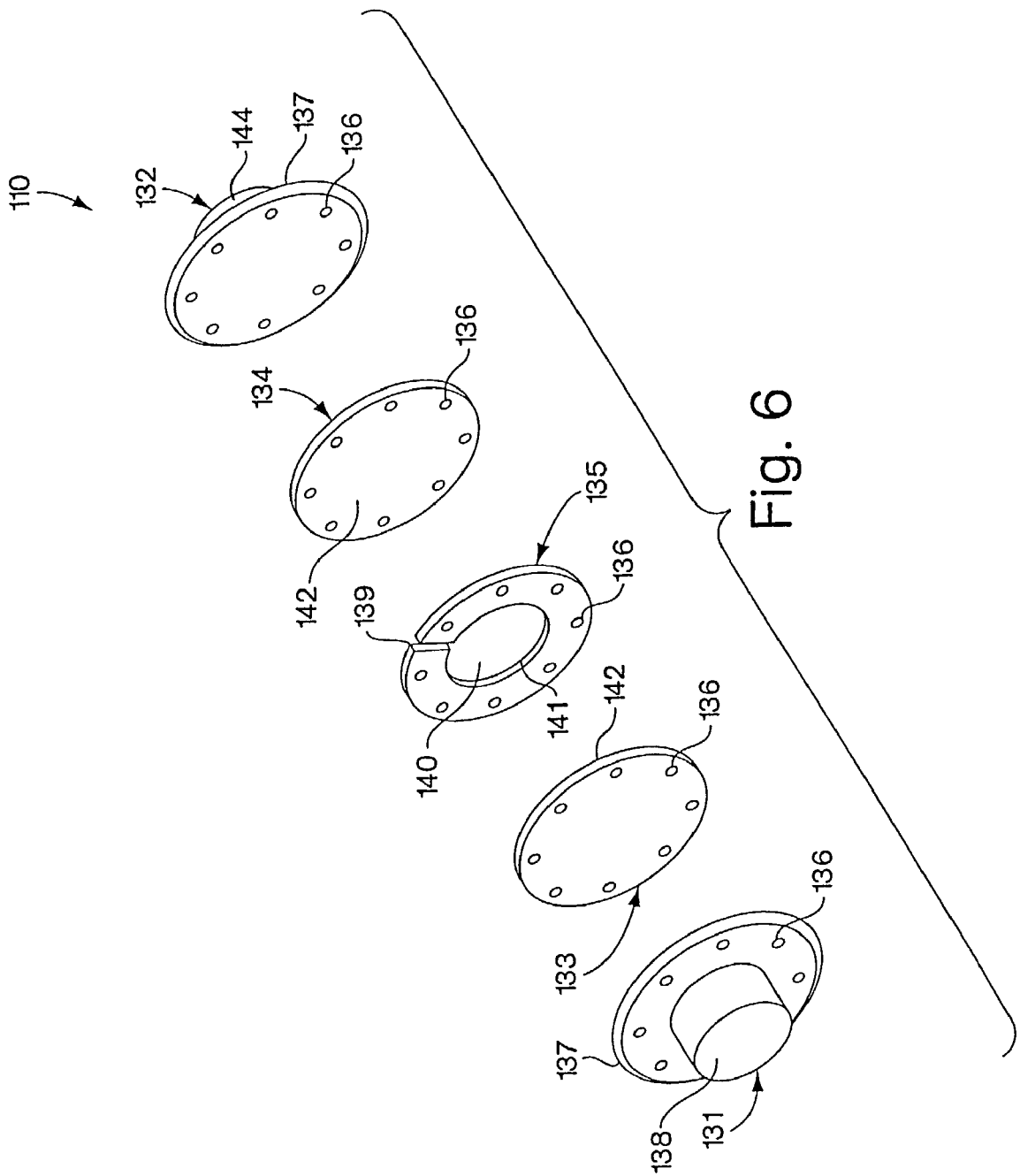
FIG. 6 is a schematic illustration showing a perspective view of a disassembled test cell according to one embodiment of the invention.

The static test cell 110 is shown in exploded view in FIG. 6. The test cell comprises an anode end block 131, which mates to anode 112 via element 138, a cathode end block 132, which mates to cathode 114 via element 144. Each end block includes a plate 137, which is circular in the illustrated embodiment, and a plurality of holes 136 through which connecting elements pass in order to assemble and seal the treatment cell 110. The end blocks are in contact with plate electrodes 133 and 134 which are in turn separated by the fluid containing annular spacer 135. Annular spacer 135 includes a channel 139 that, when the treatment cell 110 is assembled, provides a passage in fluid communication with an internal volume 140 defined by the annular wall 141 of the spacer 135 and the planar walls 142 of plate electrodes 133 and 134. In operation, the cell suspension to be treated is inserted and removed from the treatment volume 140 via channel 139. The treatment cell 110 is sized to provide a treatment volume having a desired total volume. Small scale experimental systems typically have a treatment volume of about 1-5 ml, while large scale clinical devices preferably have a treatment of 0.1-1 liter.

End blocks 131 and 132 can be constructed of any suitable conducting material. Preferred end blocks are constructed from metal. Particularly preferred end blocks are constructed from copper and subsequently gold plated, or are constructed from tungsten. Annular spacer 135 is constructed from an insulating material that is preferably biocompatible. A preferred material for constructing the annular spacer 135 is tempered glass (e.g. Pyrex® glass). Electrodes 133 and 134 can be constructed from any suitable conducting material, with preferred electrodes being constructed from conducting materials that are biocompatible and which do not release toxic amounts of electro-catalyzed reaction products during application of the electric field to the sample. Particularly preferred electrodes 133 and 134 are constructed from graphite carbon. For embodiments utilizing porous graphite electrodes 133 and 134, the electrodes are preferably degassed after introduction of a pulsing medium or cell suspension into test cell 110 so that bubbles are not released from the electrodes into the medium during application of the PEFs. Degassing can be accomplished by a variety of methods apparent to the skilled practitioner, for example the pulsing medium can be added to the assembled test cell 110 at sub-ambient temperature and subsequently heated to ambient or physiological temperature to release gas bubbles, or the pulsing medium can be added to an assembled treatment cell 110 maintained under vacuum during the adding step. A particularly preferred electrode arrangement that can reduce or eliminate the release of bubbles trapped in the porous matrix is constructed from graphite which is subsequently sealed with a sealing agent so that the surfaces 142 in contact with the pulsed suspensions are rendered essentially non-porous. In preferred embodiments, the porous matrix is sealed with a thin layer of pyrolytic carbon. The test cell 110 is also preferably constructed and arranged so that an essentially spatially uniform electric field is applied to the treatment volume 140. During use, it is important that the suspension undergoing treatment completely fill treatment volume 140 so that there is no meniscus that can distort the electric field distribution. Also, preferred treatment cells 110 are constructed and lapped to have very smooth mating surfaces on components 131, 133, 135, 134, and 132, so that when assembled, the treatment cell 110 is fluid tight without the need for supplemental seals, such as washers or O-rings.

Figure 7:
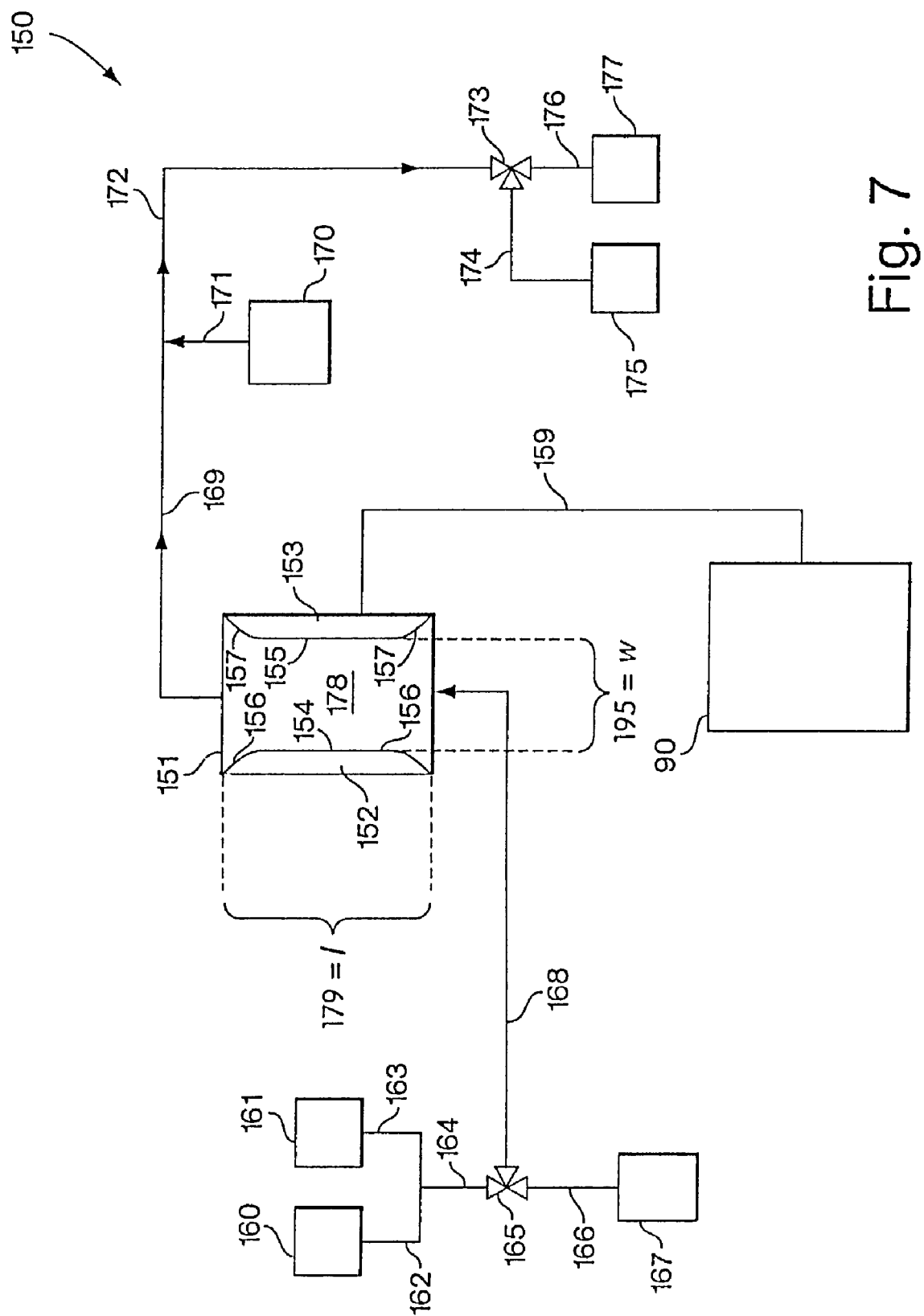
FIG. 7 is a schematic illustration of a continuous flow treatment system according to one embodiment of the invention.

A schematic diagram of a preferred continuous flow PEF system 150 is illustrated in FIG. 7. The system includes a flow-through treatment cell 151 having two electrodes 152 and 153 in fluid contact with a flowing suspension being treated that enters the treatment cell 151 through line 168 and exits through line 169. The electrodes 152 and 153 are electrically coupled to a generating mechanism 90, which can be essentially identical in arrangement as that previously described. System 150 also includes pump 160 for pumping cell-free pulsing medium through the system, and pump 161 for pumping a cell suspension through the system. Pumps 160 and 161 pump fluid via lines 162 and 163 respectively, into line 164, which is in fluid communication with three-way valve 165. Three-way valve 165 can be set to direct the pumped fluid to the treatment cell 151 via line 168 or to a waste container 167 via line 166. Pulsing medium or treated suspension exiting the treatment cell 151 via lines 169 and 172 can be controllably directed to a sample container 177 via line 176 or a waste container 175 through adjustment of three-way valve 173. Particularly preferred embodiments of system 150 also include a supplemental pump 170 which controllably pumps a desired substance into the stream of PEF treated cells via line 171. The desired substance can be a variety of materials useful in the fourth step 64 through the sixth step 66 of the exemplary procedure 60 discussed previously in reference to FIG. 3. For example, the substance supplied by pump 171 can be DNase or be Trypsin, added to inactivate released DNA and reduce cellular debris, or a medium added to raise the ionic strength and/or osmolality of the suspension in order to accelerate or bring about inactivation through colloidal osmotic lysis. The system as arranged allows the treatment cell 151 to be initially primed with pulsing medium before addition of cell suspension, and also allows the treated suspension to be diverted to waste until optimal PEF conditions are established. Also optionally included in the system 150 but not shown are mechanisms downstream of the treatment cell 151 for removing inactivated cells or cellular debris, such as filters or flow cytometers. In addition, for some embodiments, it may be advantageous to provide a cooling system, such as system 98 in FIG. 4, to remove heat from the flow-through treatment cell 151.

The preferred flow-through treatment cell 151 includes graphite electrodes constructed from similar material as discussed for electrodes 133 and 134 previously. The electrodes can be enclosed in a flow chamber constructed of an insulating material such as a plastic, or preferably, Pyrex glass. The electrodes 152 and 153 are elongated in shape and are positioned so that their long axis is parallel to the direction of fluid flow and have extended planar surfaces 154 and 155 in contact with the fluid in treatment volume 178. The electrodes are preferably constructed and arranged so that the electric field applied to the fluid in treatment volume 178 is substantially spatially uniform and so that the electric field strength upstream and downstream of the main electric field treatment region (the region bounded by the portion of the electrodes 152 and 153 that have surfaces, which are in contact with the cell suspension during operation, that are essentially parallel to one another) essentially never exceeds the strength in the main electric field treatment region. In order to accomplish this, preferred electrodes include contoured regions 156 and 157 (scale exaggerated in the Fig.) adjacent the inlet and outlet regions of the test cell 151. Well established electrode profiles exist (e.g. Rogowski, Ernst, or Chang profiles) that can be implemented to obtain the purpose of contours 156 and 157. The treatment volume 178 of the test cell 151 is defined, for rectangularly shaped test cells, as the product of the length 179, the gap width 195, and the height h (into the plane of the figure and not shown) so that $v_{TV} \approx l\,w\,h$, where $v_{TV}$ is the total volumetric capacity of treatment volume 178, l is the length of the test cell 151, and w is smallest gap width 195 between electrodes 152 and 153. These dimensions are chosen for a particular application to yield a desired volumetric throughput having a desired total treatment residence time in the treatment volume 178 and a shear rate below the value that can cause damage to the cells. For a test cell having an essentially uniform rectangular cross-section for flow, the average residence time $\tau_{res}$ of fluid in the treatment volume $v_{TV}$ is:

$$\tau_{res} = v_{TV}/u = l\,W\,h/u \qquad \text{Eq. 17}$$

where u is the volumetric flow rate of the fluid. The maximum laminar shear rate $\Gamma$ can be approximated by:

$$\Gamma = 2u(w+h)/(w\,h)^2 \qquad \text{Eq. 18}$$

The treatment cell dimensions and throughput flow rate should be selected to provide a desired total exposure time t to the electric field for a given applied pulse duration, $\tau_p$, and pulse frequency F. For example, if the desired total treatment time is t, then the necessary pulse frequency would be:

$$F = (u\,t)/(l\,w\,h\,\tau_p) \qquad \text{Eq. 19}$$

For one exemplary embodiment of treatment cell 151, length 179 is 37.3 mm, the gap width 195 is 8 mm, and the height (into the plane of the figure) is 4 mm.

Startup and operation of the flow-through system 150 can proceed as follows. The system, in this exemplary embodiment, employs syringe pumps for pumps 160, 161, and 170. With pump 160 loaded with cell-free pulsing medium, pump 161 loaded with the cell suspension to be treated, and pump 170 loaded with pulsing medium supplemented with DNase, three-way valve 165 is positioned to direct fluid to the treatment cell 151, and three-way valve 173 is positioned to direct fluid to waste container 175, and the lines and treatment cell 151 is flooded with pulsing buffer by activating pump 160 in order to remove bubbles from the system. Next, pump 160 is stopped, three-way valve 165 is repositioned to direct fluid to waste container 167, and pump 161 is activated to pump cell suspension to waste container 167 in order to remove any bubbles from line 163. Three-way valve 165 is then switched to direct the cell suspension to the treatment cell 151 and the generating mechanism 90 is activated to apply PEFs to the treatment volume 178. As soon as it is determined that the system is functioning properly, three-way valve 173 is positioned to direct the treated cell suspension into cell collection container 177. When a desired quantity of cell suspension has been processed, pump 161 is shut off and the generating mechanism 90 is switched off. Pump 170 may be operated as desired during PEF treatment to add DNase to the treated cell suspension to prevent coagulation of any cellular debris. The sequence of events just described is preferably computer controlled and pertinent PEF system data is automatically collected and stored by a data acquisition system. In alternate embodiments of flow through system 150, instead of passing through the treatment cell 151 only once, the cell suspension can be recycled back to the inlet of the treatment cell for a plurality of PEF treatments. Also in some embodiments, instead of supplying a pulsed electric field to the treatment volume 178, the field is maintained at an essentially constant value during the PEF subjecting step, and the average exposure time of the cells in the suspension is simply the average residence time of the cells in the treatment volume 178 determined by the suspension flow rate.

Pulse driver 101 (see FIG. 4) for use in systems 85 and 150 can be any suitable pulse driver known in the art that is capable of producing pulsed electric fields within the PEF treatment volume of sufficient magnitude and duration for inactivating discrete objects of interest. Preferred pulse generators are able to induce an electric field magnitude of at least about 5 kV/cm, more preferably at least about 10 kV/cm, and most preferably at least 20 kV/cm in the treatment volume. Preferred pulse generators are able to supply an electric field pulse duration above a set point electric field strength of between about 2-20 µs at pulse frequencies between about 0 to 10 kHz. Preferred pulse drivers are able to produce a substantially rectangular pulse shape, as previously discussed, with rise and fall times not exceeding about 0.5 µs. Preferred pulse driver mechanisms also include control circuitry to allow the maximum pulse voltage to be controllable by the user and to terminate pulsing upon detection of an electrical short circuit or arc. While pulse drivers based on gas switches, such as thyratrons and spark gaps, can be employed for use in the invention, because of their typically superior durability and reliability, pulse drivers based on all-solid-state switch technology are preferred.

Design specifications for the pulse driver are determined from the required maximum applied electric field strength, maximum required electric field pulse duration, the size of the treatment volume, and the electrical resistivity of the suspensions being treated. The pulse driver for use in a particular application must be designed to supply a maximum pulse energy, $e_p$ (Joules/pulse), determined by:

$$e_p = \tau_p v_{TV} E^2 / \rho_{ps} \qquad \text{Eq. 20}$$

where $\tau_p$ is the maximum pulse duration, $v_{TV}$ is the treatment volume, E is the maximum required electric field strength, and $\rho_{ps}$ is the resistivity of the sample being treated. For impedance matched conditions, the load voltage, $V_l$, is one-half the maximum charge voltage of the pulse driver. The load voltage requirements of the pulse driver can be determined by:

$$V_l = E \, w \qquad \text{Eq. 21}$$

where E is the maximum required electric field strength, and w is the distance between the electrodes (see FIG. 7). The resistance load of the treatment cell which the pulse driver must be able to handle is determined by:

$$R = \rho_{ps} w^2 / v_{TV} \qquad \text{Eq. 22}$$

where R is the impedance load ($\Omega$), $\rho_{ps}$ is the resistivity of the sample being treated, w is the distance between the electrodes, and $v_{TV}$ is the treatment region volume.

Figure 8:
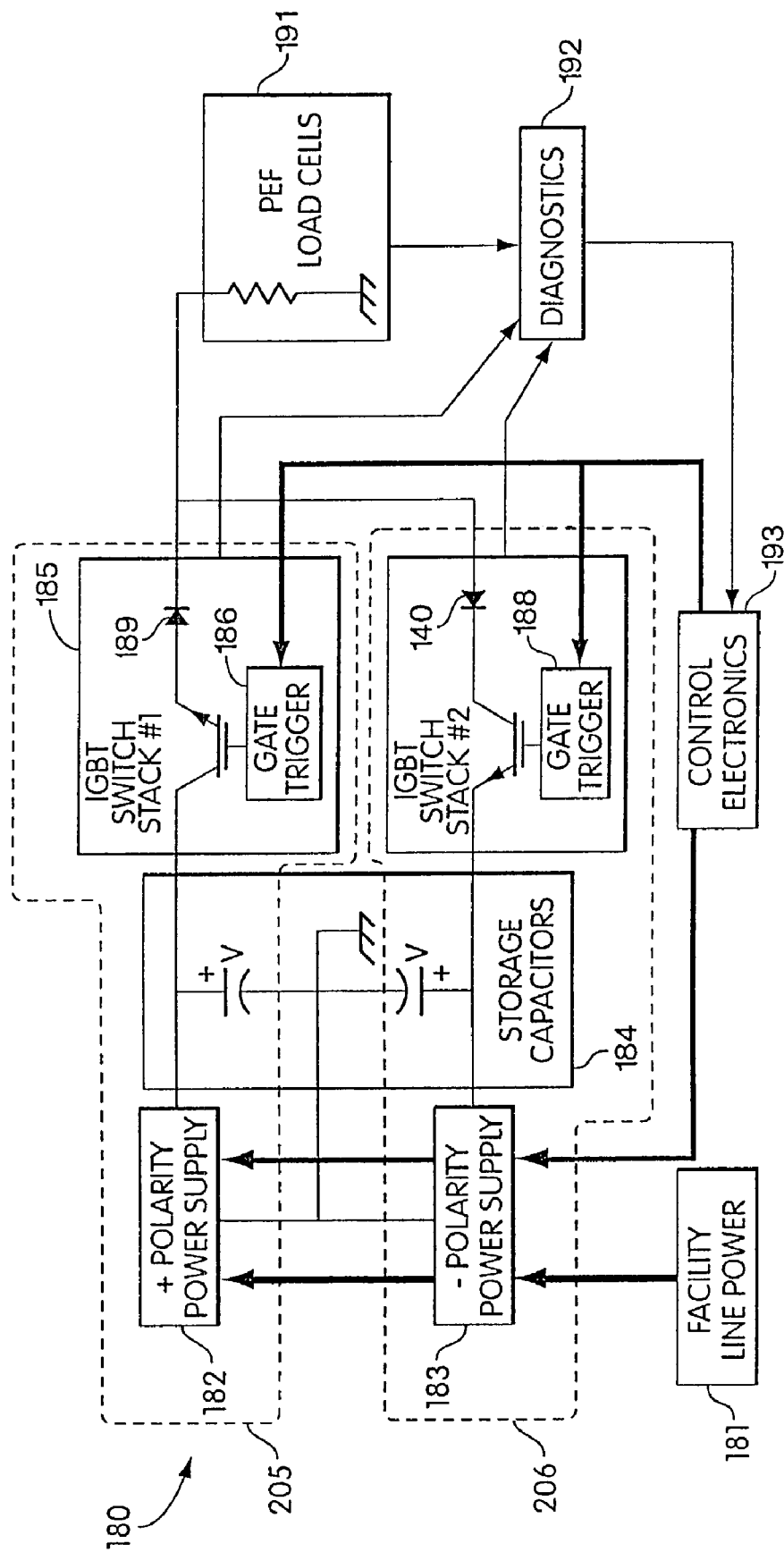
FIG. 8 is a schematic block diagram showing the components of a pulse driver system according to one embodiment of the invention.
Figure 9:
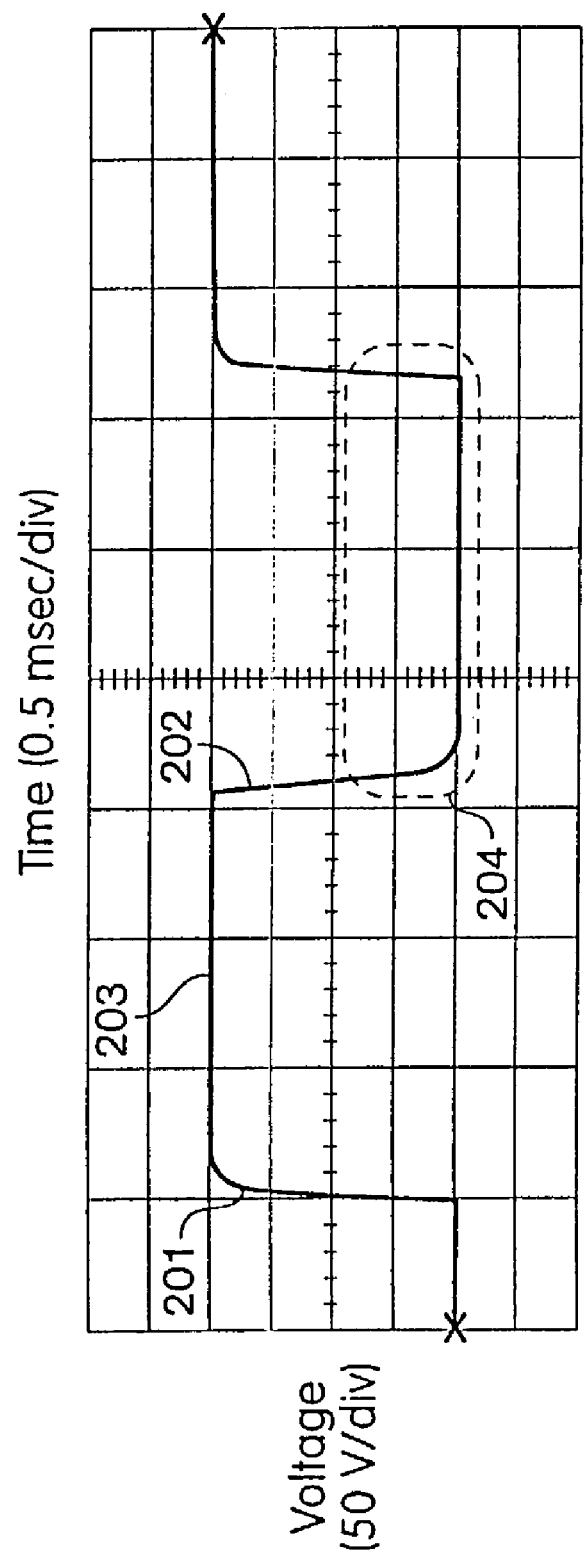
FIG. 9 is a graph showing a bipolar electric field pulse according to one embodiment of the invention.
Figure 10:
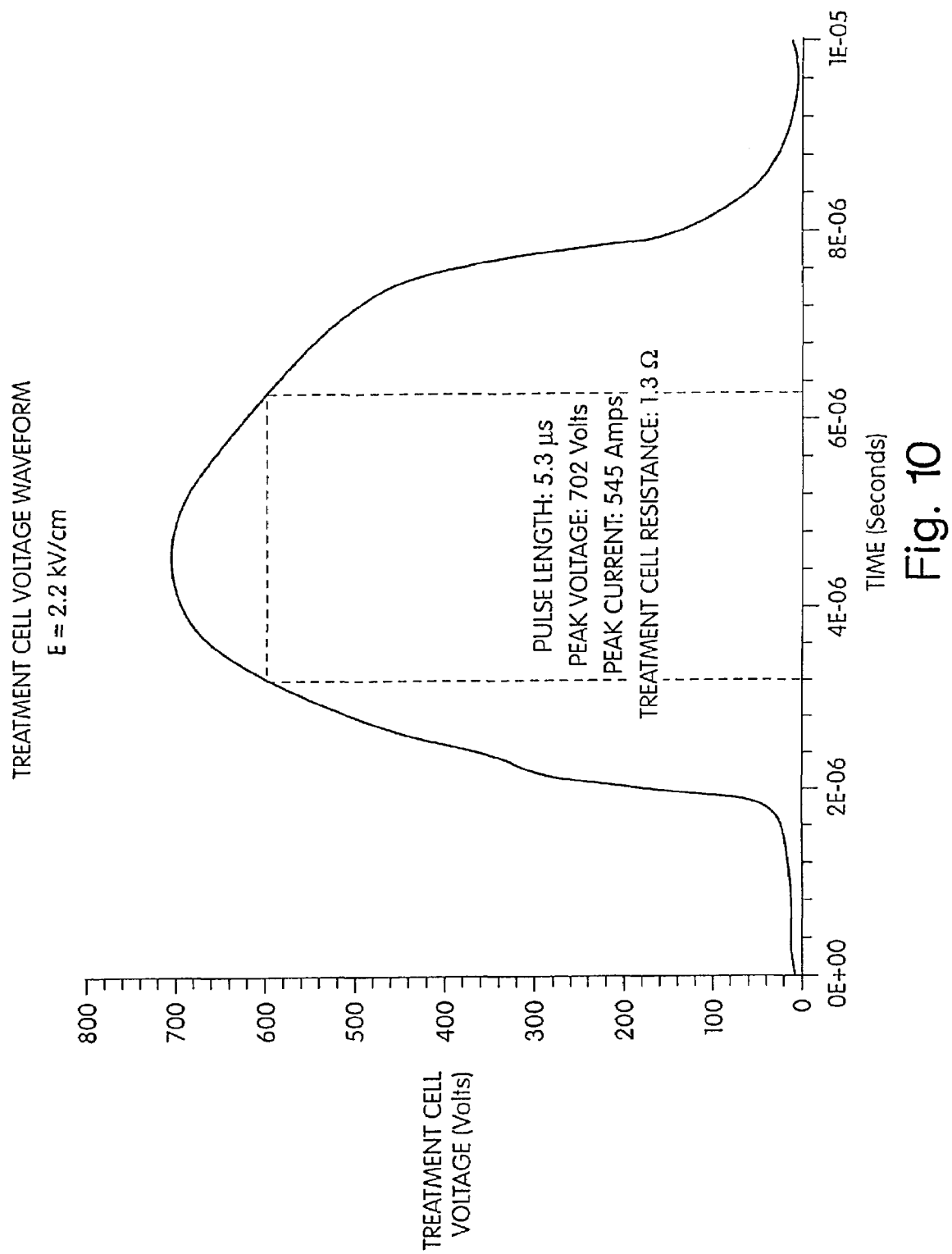
FIG. 10 is a graph showing a unipolar electric field pulse according to one embodiment of the invention.

FIG. 8 is a block diagram of one embodiment of a pulse driver system 180 for use in the inventive PEF systems. The pulse driver 180 produces the substantially rectangular bipolar pulse shown in FIG. 9. The bipolar rectangular pulse shown in FIG. 9 has short rise 201 and fall 202 times separated by flat regions 203 of substantially constant voltage. The trailing opposite polarity segment 204 of the waveform serves to reduce and/or reverse electrochemical reactions that otherwise can produce hydrogen and chlorine bubbles, which can degrade performance and affect suspension pH. In other embodiments, instead of supplying a bipolar pulse as shown in FIG. 9, the pulse generator may instead supply a 30 unipolar pulse, as shown in FIG. 10, while simultaneously supplying a reverse polarity DC current properly matched to essentially equal the time-averaged current of the electrical field pulses. The pulse shape shown in FIG. 10 is not substantially rectangular in shape but is instead in the shape of a half sine-wave. As previously discussed, such pulse shapes will, in general, yield poorer electroporation threshold selectivity than more rectangularly shaped pulses.

The pulse driver system in FIG. 8 that produces the waveform shape shown in FIG. 9 includes two pulse driver circuits 205 and 206, one 205 for a positive polarity voltage pulse, the other 206 for a trailing, negative polarity pulse. Each of the pulse drivers includes a DC power supply (182 and 183), a storage capacitor 184, and a stack of integrated bipolar transistors (IGBTs) 185 and 187, which are solid state switches that apply the electrical energy stored in the storage capacitors 184 to the PEF treatment cell 191. The IGBTs each include a switch stack and gate trigger 186, 188, and a diode 189, 190 on the output line. The IGBTs are stacked in series and parallel combinations to provide enhanced voltage and current capabilities. Power is supplied to the pulse driver system from a source 181 of facility line power. Preferred pulse driver systems also include circuitry 193 for process control and circuitry 192 for system diagnostics and data acquisition as known in the art. In preferred embodiments, the electric field strength developed in the PEF treatment cell 191 is determined by circuitry 192 for system diagnostics and data acquisition by use of a calibrated high voltage probe/oscilloscope system. The current waveform can be measured using a Pearson coil and is, in preferred embodiments, recorded on the same oscilloscope as the voltage waveform. The time integrated product of the current and voltage waveforms can then be used to determine pulse energy. Pulse energy thus determined, together with measurements of the pulse repetition frequency and the temperature of the electrodes in the treatment cell 191 can be used, together with a heat transfer mathematical model describing the heat transfer characteristics of the treatment cell 191, to calculate the temperature evolution of the pulsed suspension. Alternatively, the temperature of the pulsed suspension can be directly measured in a plurality of locations within the treatment volume with suitable temperature probes or thermocouples. Diagnostic 192 and control 193 systems also, in preferred embodiments, include one or more computer elements, for example integrated personal computers, to control system operation and perform data reduction and analysis.

The function and advantage of these and other embodiments of the present invention will be more fully understood from the examples below. The following examples are intended to illustrate the operation of the present invention, but not to exemplify the full scope of the invention.

EXAMPLES

Introduction

The experimental examples that follow, presented as five separate cases, demonstrate pulsed electric field cell-size selectivity, hematopoietic primitive progenitor cell enrichment, and tumor cell purging. Two PEF cell-size selection examples are presented (Cases 1 and 2). In Case 1 PEFs were applied to a suspension of peripheral blood mononuclear cells resulting in a step-wise reduction in size distribution of the PEF treated viable cells as a function of electric field strength and total electric field exposure time. In Case 2 PEFs were applied to a suspension of peripheral blood mononuclear cells, illustrating lymphocyte enrichment by selective inactivation of monocytes in PEF treated specimens as a function of electric field strength and electric field exposure time. Case 3 illustrates the enrichment of hematopoietic stem cells in PEF treated peripheral blood progenitor cell specimens. In Case 3, PEFs were applied to mobilized peripheral blood specimens harvested from a patient by leukopheresis. Case 3 illustrates the dependence of stem cell enrichment on electric field strength for a fixed electric field exposure time. Two cases are presented that illustrate PEF tumor cell purging (Cases 4 and 5). In Case 4, PEFs were applied to a suspension of peripheral blood mononuclear cells seeded with a megakaryocyte tumor cell line (CMK). This case illustrates the selective inactivation of the tumor cells with simultaneous preservation of lymphocyte and monocyte cells as a function of electric field strength and fixed total electric field exposure time. In Case 5 PEFs were applied to a suspension containing only mammary gland breast tumor cells (MCF-7). This case illustrates the PEF inactivation characteristics of this breast tumor line as a function of electric field strength, pulse duration, and total electric field exposure time. The examples given by Cases 1-5 were performed under non-optimized PEF conditions. Thus, these results represent a lower end demonstration of the capability of the PEF cell selection strategy.

Methods and Materials

The methods and materials for the five example cases are given together below and are broken into three categories: cell preparations, cell assays, and PEF apparatus.

Cell Preparations

Four cellular systems were used in the example cases: peripheral blood mononuclear cells (PBMCs), mobilized peripheral blood mononuclear cells (hereafter referred to as peripheral blood progenitor cells, (PBPCs)), megakaryocyte tumor cells (CMKs), and mammary gland breast tumor cells (MCF-7s).

PBMCs were used in Cases 1, 2, and 4. The PBMCs were obtained from healthy donors by harvesting approximately 60 ml of peripheral blood per test day by venipuncture through a 21G, 1 inch needle (Beckton Dickinson, 305175) into a syringe (Beckton Dickinson, 309663) containing 1 ml Heparin (5000U, Elkins-Sinn, Inc., A-0400H). The PBMCs cells were separated from the whole blood using standard density gradient centrifugation techniques. Under sterile conditions, the blood was diluted with twice its volume with 1× phosphate buffered saline (PBS, Mediatech, 21-031-CV) and then aliquoted (30-40 ml) into 50 ml conical centrifuge tubes. Ficoll-Paque (Pharmacia Biotech, 17-0840-03) was slowly dispensed into the bottom of each centrifuge tube, and the tubes were centrifuged (IEC, Centra GP8R, rotor no. 228) at 2000 RPM for 30 minutes with the brake off. The PBMCs at the density interface were collected by aspiration with a 5 ml pipet. The recovered PBMC layers were combined into a single 50 ml centrifuge tube. The resulting PBMC suspension was then diluted 10× using PBS, aliquoting into as many 50 ml centrifuge tubes as required, followed by centrifugation at 1500 RPM for 5 minutes. The supernatant was aspirated, and one pellet was resuspended in 10 ml PBS. This 10 ml suspension was then used to resuspend the pellets of all remaining tubes. PBS was then added to the resulting suspension, bringing the total volume to 50 ml. This 50 ml suspension was centrifuged at 1500 RPM for 5 minutes; the supernatant was aspirated; the pellet was then resuspended in 20 ml IMDM (Sigma, 12762) with 10% fetal calf serum (FCS, Sigma, F 2442), and then transferred to a flask and placed in an incubator at 37° C. overnight in preparation for PEF treatment the next day. The next morning the contents of the flask were transferred to a 50 ml centrifuge tube. The flask was washed three times with 10 ml PBS: these PBS wash volumes were added to the 50 ml tube containing the bulk of the PBMC specimen. The resulting suspension was then centrifuged at 1500 RPM for 5 minutes; the supernatant was aspirated, and the cells were suspended in the desired pulsing buffer. Pulsing and post-PEF treatment buffers are discussed in more detail in a subsequent section.

Cell preparation for Case 3 was identical to that for Cases 1 and 2 with the following exceptions. The cells for Case 3 were obtained by leukopheresis from a cancer patient that had been administered granulocyte colony stimulating factor (G-CSF). More specifically, mobilization of the patient's peripheral blood was effected by administering G-CSF (10 µg per kg body weight per day) subcutaneously for 4-6 days, with apheresis collections beginning on day 4 until $2.5 \times 10^6$ CD34+cells per kg body weight were obtained. The resulting cell suspension contained approximately $2 \times 10^8$ leukocytes in approximately 2 ml PBS. This cell preparation was used, instead of the whole blood in the protocol described above for obtaining PBMC preparations. Before suspending the PBPCs in the pulsing buffer, the resting lymphocyte population was activated to move these cells to their larger, active state in order to improve for stem cell enrichment. To activate the lymphocytes, the PBPC suspension, interleukin-2 (IL-2, 50 IU/ml, R n' D Systems) and PHA (0.25 µg/ml, Sigma) were added to a culture medium (20 ml, IMDM, 10% FCS) and incubated at 37° C. for 36 hours. After activation (incubation), the suspension was centrifuged at 1500 RPM for 5 minutes, the supernatant was aspirated, and the resulting pellet was resuspended in the desired pulsing buffer.

For Case 4, PBMCs, prepared as described above for Cases 1, 2 and 4, were seeded with a megakaryocyte tumor cell line (CMK, Sato T. et al., *Br. J. Haematol.* 1989 June; 72(2): 184-90). For Case 5, a suspension containing only mammary gland tumor cells (MCF-7, ATCC no. HTB-22) was exposed to PEFs. Preparation of the MCF-7s for PEF treatment is described below with modifications to the procedure for the CMK line noted. MCF-7 (ATCC no. HTB-22) cells were thawed under the following conditions. A vial of cells was thawed at 37° C., then transferred to a 50 ml tube (Fisher, 14-959-49A) containing 30 ml of 1× Iscove's medium without glutamine (IMDM, Fisher, MT15 016LV) and centrifuged at 1500 RPM for five minutes at room temperature. The supernatant was discarded and the pellet was resuspended in 20 ml of MCF-7 culture-medium and cultured at 37° C., 5% $CO_2$. The MCF-7 culture medium used was 1× Dulbecco's modification of Eagle's medium, without glutamine, including 4.5 g/L glucose, and supplemented with 2 mM L-glutamine (Fisher/Cellgro, MT-25-005-LI), 50 I.U./ml of penicillin, and 50 µg/ml streptomycin (Fisher/Cellgro, MT-300-01-LI) and 20% FCS. The cells were split upon reaching confluence, typically every three to four days, as follows. Culture supernatant was aspirated and replaced with 5-6 ml of trypsin (2.5 g/L 1:250 in HBSS without calcium or magnesium, Fisher/Cellgro, 25-050-11). After incubation at room temperature for 5 minutes, the flask was rinsed using 10 ml of 1× Dulbecco's Phosphate buffered saline without calcium or magnesium (PBS, Fisher/Cellgro, MT-21-031-CV) supplemented with 1% fetal calf serum (FCS, Sigma, T-2442). The rinse solution was then transferred to a 50 ml tube, and the volume was made up to 50 ml with PBS, supplemented with 1% FCS, before centrifuging the tube, as described above. After centrifugation, the supernatant was discarded and the pellet was resuspended in 10 ml of MCF-7 culture medium. Five milliliters of this suspension was transferred to one of two 75 $cm^2$ flasks, each containing 15 ml of MCF-7 culture-medium, prior to reculture under the above described conditions. If there were more than two flasks to be split, then the excess cells were frozen as follows. The cells were trypsinized and washed as previously described, and then resuspended in 1 ml of freezing medium (10% DMSO, Fisher, D128-500, 90% FCS), per flask and transferred to labeled cryovials (Fisher, 5000-1020) prior to transfer to a −70° C. freezer. MCF-7 PEF treatment commenced the morning after these cells achieved half-confluency in the culture flasks. On the morning of a PEF experiment, the MCF-7s were trypsinized using the above protocol, the recovered cells were then washed using PBS, and the centrifuge pellet was then suspended in pulsing buffer in preparation for PEF treatment.

For the CMK line, the cell suspensions were thawed as previously described for the MCF-7 line and cultured in CMK culture medium at 37° C., 5% $CO_2$. The CMK culture medium comprised 1×RPMI 1640 medium, without glutamine, supplemented with 2 mM L-glutamine (Fisher/Cellgro, MT-25-005-LI), 50 I.U./ml of penicillin, and 50 µg/ml streptomycin (Fisher/Cellgro, MT-300-01-LI) and 20% FCS. The CMKs were split 1:10 every 3-4 days by transferring about 2 ml of the cell suspension to a new 75 $cm^2$ flask containing 18 ml of CMK culture medium. Excess cells were frozen as previously described. On the morning of a PEF treatment experiment, the CMKs were transferred from the culture flasks to 50 ml Falcon tubes (Becton Dickinson, 2098). As part of this transfer, the cells were passed through a separation filter (Miltenyi Biotec, Inc., 414-07) to remove large-scale debris. The cells were then washed in PBS and resuspended in the pulsing buffer in preparation for PEF treatment.

Pulsing Medium

For Cases 1 and 2, IMDM was used as the medium in which the PBMCs were suspended for PEF treatment. After PEF treatment, the treated specimens were combined with an equal volume of IMDM. The resulting specimen remained at room temperature until preparation for flow cytometry analysis.

For Cases 3, 4, and 5, the cells were suspended in a low ionic strength medium (10% v/v PBS, 90% v/v isotonic sucrose solution). This low ionic strength pulsing medium was formulated to be isotonic. After PEF treatment, the treated specimen was combined with an approximately equal volume of IMDM. The inactivation protocol using a low ionic strength pulsing medium, followed by resuspension in a higher ionic strength medium, was used in these cases to investigate whether the combination would result in more extensive post-PEF fragmentation of PEF porated cells by colloidal osmotic lysis. The low ionic strength pulsing buffer was formulated as follows. Twenty milliliters of 1× sterile PBS was combined with 180 ml of distilled/deionized water. To this solution, 16.6 g of powdered sucrose was added (Fisher, BP220-212). This solution was then sterilized by passing it through a 0.2 μm filter (Nalgene, 291-3320). The pH of the resulting solution was checked using a Beckman ($\phi$40 pH meter and was found typically to lie in the range 7.4-7.6. Prior to final preparation of the cellular suspensions for pulsing, trypan blue exclusion using phase contrast microscopy was employed to enumerate the number of viable cells present in PBS suspensions of the various cells. Given the number of cells desired in the cellular suspensions for pulsing, the trypan blue results were used to determine the volume of PBS cell suspension required to provide the desired number of cells, which volume was then centrifuged to pellet the cells. The pellet was then suspended in the required amount of pulsing buffer.

Cell Assays

Pre- and post-PEF cell enumerations were performed using both trypan blue exclusion, using a hemacytometer (Fisher, 02-671-10) under phase contrast optical microscopy, and a wide variety of well established flow cytometry protocols. Trypan blue exclusion was used primarily for determining the number of viable cells to suspend in the pulsing medium for each experiment. Flow cytometry, using a variety of viability and conjugate antibody fluorescent stains, was used to enumerate pre- and post-PEF viable cell numbers, including lymphocytes (B- and T-cells), monocytes, primitive progenitor cells (including stem cells), and tumor cells (CMK and MCF-7). A Becton Dickinson FACScan flow cytometer was used to perform the analytical assays. For Cases 1, 2, 3, and 4, cell viability was determined by flow cytometry using either propidium iodide (PI, Molecular Probes, P-3566) or TO-PRO-3 (Molecular Probes, T-3605) DNA staining combined with light scatter characteristics. Viable lymphocytes were identified as those cells scoring low for the particular DNA viability stain used (either PI or TO-PRO-3) while staining brightly for CD3 (T-cells, Fisher, OB9515-02 or -09) or CD19 (B-cells, Fisher, Becton Dickinson, 340409 or 340364). Viable monocytes were identified as those cells scoring low for the DNA viability stain used while staining brightly for either CD11b (Becton Dickinson, 347557), CD13 (Fisher, OB9555-02 or -09), or CD14 (Fisher, OB9560-02 or -09) and CD45 (leukocytes, Fisher, OB9625-02 or -09). Viable hematopoietic stem cells were identified as those cells scoring low for the DNA viability stain used while staining brightly for CD34 (Fisher, OB9595-02 or -09) and dimly for CD38 (Fisher, OB9610-02 or -09). Viable CMK tumor cells were identified as those cells scoring low for the DNA viability stain used, staining dimly for CD14, and staining brightly for CD45, while also being outside of the light scatter compartments for lymphocytes and monocytes (light scatter gating).

For Case 5, involving the PEF inactivation characteristics of MCF-7 tumor cells, viable MCF-7s were identified as those cells scoring low for both the apoptotic membrane stain Annexin-V (Caltag, Annexin VV01-3) and the DNA stain PI. Light scatter gating was also used to discriminate cells from cell debris that was smaller than the smallest of the MCF-7 cells. Both PI and Annexin-V viability stains were used for MCF-7 analysis based on the following considerations. Propidium iodide is a DNA stain. Thus, for cells with disrupted membranes, yet still containing a nucleus, this dye will stain non-viable cells. Annexin-V, however, stains phosphatidylserine (PS) which migrates from the inside to the outside of the plasma membrane during normal apoptosis. Thus, it is normally used as an indicator of apoptotic, but still viable cells. Whether or not the PS migrates to the external surface of the cell as a result of PEF treatment is unimportant. What is important is that should PEFs result in the discharge of the nucleus from the cell, Annexin-V will stain the PS on the inside of the plasma membrane, since this stain has access to the inside of the cell due to membrane disruption. Thus, ghost cells should have a bright Annexin-V fluorescence signature. Therefore, gating based on both PI and Annexin-V has been found by the inventors to give the best screening for viable MCF-7 cells.

Test and Control Specimens

On a given test day, both control specimens and PEF treated specimens were prepared. Two types of controls were prepared: 1) a stock cell control specimen and 2) a PEF test cell control specimen. Stock cell suspension refers to the cellular suspension in pulsing medium from which fixed volume aliquots were taken for loading into the PEF treatment cells. The stock cell suspension controls were prepared by placing the same volume of stock cell suspension into a 15 ml centrifuge tube as would be loaded into the PEF treatment volume. An additional 5 ml of IMDM was then added to the same tube. The PEF treatment cell controls were prepared by loading a PEF treatment cell with the appropriate volume of cell suspension and allowing it to stand at room temperature for the period of time it would normally take to treat a specimen with PEFs; however, during this time, no PEFs were applied to the PEF treatment cell control specimens. When the standing period expired, the specimen was removed from the PEF treatment cell and placed in a 15 ml centrifuge tube to which 5 ml of IMDM was added. The PEF treated specimens were handled in the same way as the PEF treatment cell controls, except PEFs were applied to the treated specimens.

The control specimens served two purposes. First, a comparison of the total viable cell counts, as provided by flow cytometry, between the stock cell controls and treatment cell controls gave an indication of the fraction of cells lost simply by virtue of residence in the PEF treatment cells. Second, the cytometry counts from the treatment cell controls for each cell type were used to normalize the cytometry counts for each cell type for the PEF treated specimens. This allowed for computation of the surviving percent for each cell type for each set of PEF conditions. To obtain consistent and meaningful cytometry counts, the following general procedure was followed. By virtue of the fact that the PEF treatment cells employed had a fixed volume, and that the stock cell suspension controls were prepared using a stock cell specimen having the same volume as the PEF treatment cells, all of the specimens prepared on a given test day had the same number of input cells. When preparing the control and PEF treated specimens for flow cytometry analysis, all cellular material present prior to PEF treatment was ultimately contained in the aliquot the cytometer drew from when performing the flow cytometry assays. Thus, if the volume of each cytometry aliquot was the same for all specimens on a given test day, then acquiring counts for a fixed acquisition time for all specimens would provide viable counts that could be compared across the specimens prepared on a given test day. Most importantly, the viable counts for the treatment cell controls could then be used to normalize the viable counts for each PEF treated specimen, thereby providing the information needed to compute surviving percent for each PEF-exposed specimen.

Flow Cytometry

The following procedures were used during preparation of the control and PEF-treated specimens for flow cytometry analysis. 100 µl of DNase I (100 mg; 500 Kunitz-units per mg solid, Sigma, DN-25) was added to each specimen to minimize coagulation by released DNA. The specimens were then vortexed and centrifuged for 6 minutes at 1500 RPM. The supernatant was aspirated and the pellet was washed with 5 ml PBS. When preparing for PI and Annexin-V staining, the specimens were centrifuged again for 6 minutes at 1500 RPM; the supernatant was aspirated, and 100 µl of 1× calcium buffer was added (Bender MedSystems, BMS306BB), followed by addition of 150 µl of propidium iodide (PE conjugate) and 5 µl of Annexin-V (FITC conjugate). These specimens were incubated at room temperature for 15 minutes. Next, 300 µl of 1× calcium buffer was added, the sample vortexed, and then the specimens analyzed under flow cytometry. PI/Annexin-V staining was the only staining used for Case 5 where the PEF inactivation characteristics of MCF-7s (with no other cellular species present) is presented. PI staining, in conjunction with other conjugate monoclonal antibody stain, was used for Cases 1 and 2, where the inactivation of PBMCs is presented: Annexin-V viability staining was not used for these cases (Cases 1 and 2). For Case 1, the specimens were also stained using the conjugate monoclonal antibodies CD3 and CD13 in order to enumerate lymphocyte (T-cells) and monocyte/granulocyte cells, respectively. For Case 2, the specimens were also stained with the conjugate monoclonal antibodies CD3 and CD13 in order to enumerate lymphocyte (T-cells) and monocyte cells, respectively. For Case 3, the washed pellets were resuspended in 200 µl PBS, which was then aliquoted to two 100 µl specimens. The conjugate monoclonal antibody stains CD14 and CD45 were added to one of these aliquots for enumeration of lymphocyte and monocyte cells, respectively. The conjugate monoclonal antibody stains CD34 and CD38 were added to the second aliquot for enumeration of primitive progenitor cells (hematopoietic stem cells). Both aliquots were then incubated at room temperature for 15 minutes. These aliquots were then washed with 2 ml PBS, centrifuged for 6 minutes at 1500 RPM; the supernatant was then aspirated, and 500 µl of 1 µg/ml TO-PRO-3 viability stain was added to the tube. The resulting aliquots were then incubated for 15 minutes at room temperature, vortexed, and analyzed under flow cytometry. The staining for Case 4 was very similar to Case 3, except the specimens were not stained with the CD34/CD38 conjugate monoclonal antibodies. Rather, these specimens were stained with the conjugate monoclonal antibodies CD3 and CD19 (in addition to CD14 and CD45) in order to enumerate T- and B-cells, respectively.

When analyzing Cases 1, 2, 4, and 5 under flow cytometry, approximately 100,000 cytometer events were found to give adequate resolution of the cell types of interest (lymphocytes, monocytes, tumor cells). Due to their rare frequency, however, 500,000-1,000,000 cytometer counts were required to identify the CD34+/CD38− stem cell population for Case 3.

PEF Apparatus

The apparatus used for the examples that follow was a batch PEF treatment system, i.e., PEF treatment takes place in a fixed, static PEF treatment volume. The batch PEF system is comprised of a batch PEF treatment cell, an electrode enclosure assembly that holds the PEF treatment volume during exposure to PEFs, an electric field pulse generator that applies voltage pulses to the PEF treatment cell, and a computer control/data acquisition system.

The essential details of the PEF treatment cell used for the examples is illustrated in FIG. 6. The treatment volume is formed by stacking the end blocks 131, 132, graphite disk electrodes 133, 134, and Pyrex annular spacer 135 as shown in FIG. 6. This treatment cell has a sealless design, i.e., no O-ring or gasket seals are employed to seal the PEF treatment volume 140, defined by the mating of the Pyrex annular spacer and graphite disks. Rather, all mating surfaces were lapped to a waviness of no more than 2.5 µm over the diameter (8.26 cm) of the disks involved the assembly. Furthermore, all mating surfaces were lapped to a number 4 surface finish, which had an RMS variation in surface deviations of +/−0.1 µm. The graphite disks were made of ISO-63 graphite, which had an average pore size of 1 µm. The tolerances were chosen to prevent blood cells, which are typically greater than 5 µm, from finding their way into the interface regions of the mating treatment cell components, or penetrating into the pores of the graphite disk electrodes. Nylon screws were employed to hold the treatment cell assembly together. Since all internal surfaces of the treatment cell were either normal to the electric field direction (e.g. conducting surfaces) or were parallel to the electric field direction (e.g. insulating surfaces), the utilized treatment cell geometry provided very uniform electric field strength over the entire treatment volume. The end blocks of the treatment cell were made of gold coated copper. The gold coating was included to minimize surface oxidation and to provide excellent electrical contact with the assembly that holds the treatment cells during PEF treatment. The pulsing suspension was loaded and unloaded from the PEF treatment cell through the radial channel 139 in the Pyrex annular spacer by using a pipetting syringe (pipetting needles, Fisher, 14-825-16N); 10 ml disposable syringes, Fisher, 14-823-2A).

The treatment cell just described was used for Cases 1, 2, 3, and 4. It is referred to hereafter as the Type A test cell. For Case 5, a variant of the Type A test cell was used. This variant is referred to as the Type B test cell (not shown) and was similar to the Type A test cell previously described with the following differences. The type B test cell used tungsten electrodes, rather than graphite and the annular spacer was made of plexiglass that had four radial holes (1 mm I.D.), equally spaced around its perimeter, that penetrated from the outer surface through to the inner surface. A silicon washer, which had an outside diameter equal to the inside diameter of the plexiglass spacer and which was approximately 0.05 mm thicker than the plexiglass annular spacer, was inserted inside the plexiglass spacer during assembly of the Type B test cell, which silicon washer ultimately formed the circumferential bounding wall of the PEF treatment volume. Once the Type B test cells were assembled, they were loaded and unloaded with cell suspension through the 1 mm I.D. holes using A 21G hypodermic needles mated to 1 ml syringes (21G needles, Becton Dickinson, 305176; 1 ml syringes, Becton Dickinson, 5602).

The internal dimensions of the test cells that were critical for the heat transfer and electric field strength calculations, were as follows. For the Type A test cells, the diameter of the cylindrical treatment volume was 4.45 cm, and the gap between graphite electrodes, when the test cell is assembled, was 3.2 mm, which yields a volume of 4.94 ml. For the Type B test cells, the diameter of the cylindrical treatment volume was 10.91 cm, and the gap between graphite electrode was 2.5 mm, which yields a volume of 0.72 ml. The parts making up the test cells were fabricated using standard methods known in the art.

In general, electrochemical reactions take place in the region near the electrode surfaces when a current is passed through the electrodes into an electrolyte solution. For the present application, were thousands of electric field pulses may be applied, gold is not a good electrode candidate. This is because free chlorine ions can react with the gold, forming a gold salt, which dissolves in the electrolyte. Tungsten is a reasonably inert electrode material, but it can react with free oxygen ions to form an oxide layer on the electrodes. Carbon electrodes (graphite) are the preferred electrode material since graphite is substantially inert with respect to the ionic species formed during PEF treatment.

To demonstrate to the importance of controlling electrochemical reactions, separate experiments were performed where electric field pulses were applied to isotonic potassium chloride solutions. Plumes of bubbles were observed to be released from both the anode and cathode electrodes of the Type A test cell. Furthermore, after a thousand pulses, the pH of the solution shifted from 7.0 to 6.0. However, when a DC counter-current was driven through the test cell during pulsing, which had a current equal to and opposite of the time average of the primary electric field pulses, no bubble formation was detected and the swing in pH was undetectable. These experiments illustrated the ability of using a reverse polarity current to control electrochemical reactions in unbuffered aqueous solutions having high (i.e. physiological) ionic strengths. Reverse polarity currents were not employed in the example cases to follow since the pulsing media used for those cases was typically of lower ionic strength and included a buffer to counter the effects of low concentrations of electrochemically produced products.

Once the test cells were loaded with the desired cellular suspension, the test cells were then mounted in an electrode/enclosure assembly that supports the test cell when the PEFs are applied to the test cell. The electrode/enclosure assembly used for the example cases following has essentially the same features as the assembly shown in FIG. 5. This assembly serves three purposes. First, it provides electrical contact between the electric pulse generator and the PEF treatment cell. Second, it provides temperature control for the test cell. Third, it encloses the test cell during PEF treatment, thereby protecting personnel in close proximity to the system from high voltage components. With reference to FIG. 5, the temperature of the test cells were controlled by contact with temperature-controlled cathode 114 and anode 111 supports of the electrode/enclosure assembly 95. The temperature of the cathode and anode supports is controlled by circulating temperature controlled water through these structures using a heater/chiller system (Neslab, RTE-110). This system is capable of setting the temperature of the test cells to +/−0.2° C. over the range 0-50° C. After mounting the test cells in the electrode/enclosure assembly, the test cells were allowed to reach thermal equilibrium with the temperature of the cathode and anode structures in the electrode/enclosure assembly.

The electric pulse generator system used for the examples consisted of an energy storage capacitor (3 kV, 500 µf, Maxwell, 38683), which was connected to an all-solid-state pulse driver designed and fabricated by the inventors for driving a $CO_2$ laser. The pulse driver (electric pulse generator) is referred to as the COLD-I. This driver switches the energy stored in the 500 µf capacitor via solid-state SCR switches to a 20:1 saturable core transformer into an impedance matched load (~8 Ω). This driver, as presently configured, can deliver fixed duration voltage pulses (~5 µs duration) at voltages up to 8 kV. Under these conditions, the deliverable pulse energy is ~80 J. The storage capacitor was charged via a Maxwell (1 kV, 5 kJ/s, CCDS 501P372-208) high voltage charging power supply. Normally, the voltage output of the COLD-I is to high for use for PEF cell selection. This was remedied by using a high power voltage divider circuit, which simply comprised two resistors in series connected to ground. This voltage divider circuit could attenuate the voltage pulses delivered to the PEF test cell by factors of 4-20 simply by changing the resistance of the two resisters in the circuit.

A Pearson coil current transducer was used to monitor the current delivered to the PEF test cell. A second Pearson coil transducer measured the current through a precision 100 Ω resister connected across the PEF test cell. The voltage applied to the test cell was derived from the second Pearson coil transducer signal by multiplying it by 100 Ω. These current and voltage signals were displayed on a LeCroy oscilloscope (9410). FIG. 10 presents the voltage waveform produced by the COLD-I driver when applied to a Type A test cell containing a room temperature isotonic potassium chloride solution, which corresponds to imposing a 2.2 kV/cm electric field in this saline solution.

An IBM personal computer clone was used for system control and data acquisition. During PEF treatment, a control program was run that issued pulse driver trigger signals. The frequency and number of the trigger signals was set by the operator based on the PEF conditions desired. The magnitude of the voltage pulses delivered to the PEF test cell, however, was set by a dial associated with the Maxwell charging power supply. The output trigger signal from the PC control computer was delivered to an opto-isolator circuit, which prevented any electric noise from feeding back to the PC. The output of the opto-isolator circuit was delivered to an HP 214-B trigger generator, which, in turn, sent a 100 volt, 2 µs pulse to the COLD-I driver, which triggered the COLD-I, thereby applying the desired electric field pulse to the PEF test cell.

Upon completion of a PEF treatment experimental trial, the voltage and current waveform data was downloaded from the oscilloscope to the PC computer via a GPIB interface. After the data was downloaded, post-processing computations were performed. More specifically, the following quantities were computed: peak voltages and currents, the resistance of the test cell, the full-width at half-maximum (FWHM) electric field pulse length, and the energy delivered to the test cell per electric field pulse. For the cases that follow, the electric field strengths quoted were those based on the peak voltage of the pulses delivered to the PEF test cell. Furthermore, the electric field pulse lengths quoted were the FWHM values. After computing the single pulse energy deposited to the test cell, the average midplane temperature rise in the PEF test cell and the temperature jump per electric field pulse for a given PEF treatment trial was computed. These temperatures, when quoted in the cases that follow, were derived using Eqs. 14, 14a, and 14b given earlier in the detailed description.

Case 1. Step-Wise PEF Inactivation of PBMCs

The ability of PEFs to selectively inactivate cells in a step-wise, size-dependent manner with increasing electric field strength and exposure time is demonstrated in this case. The stock cell suspension contained PBMCs suspended in IMDM at a concentration of $1.1 \times 10^6$ cells/ml. The pulsing medium was of standard physiological ionic strength. The input cells and stock cell suspension were prepared as previously described. Type A test cells were used in the Case 1 trials. Pulsed electric fields, having strengths in the range 1.4-1.8 kV/cm, were applied to the specimens. The total electric field exposure times were in the range of 0.18-5.97 ms, and the electric field pulse length was about 5.75+/−0.2 μs (FWHM). The total electric field exposure time was varied over the noted range by varying the number of applied electric field pulses over a range of 30-1000 pulses. The single pulse energy deposited to the test cells ranged from 0.54-0.88 J/pulse. The electric field pulses were applied at 1 Hz. The end blocks of the test cells were maintained at 35° C.+/−0.2° C. Based on Eqs. 14, 14a, and 14b, the average midplane temperature varied over the range from about 35.2-35.4° C. and the temperature jump per electric field pulse varied over the range 0.03-0.04° C. One stock cell control specimen and one test cell control specimen were prepared before commencing PEF treatments, and one test cell control specimen was prepared after all PEF treatments had been performed for the test day in question. The control and PEF treated specimens (about 5 ml each) were placed in 15 ml centrifuge tubes after preparation, to which an approximately equal volume of IMDM was added as previously described. These specimens were then analyzed by flow cytometry for enumeration of viable cell types and numbers as also previously described.

Figure 11:
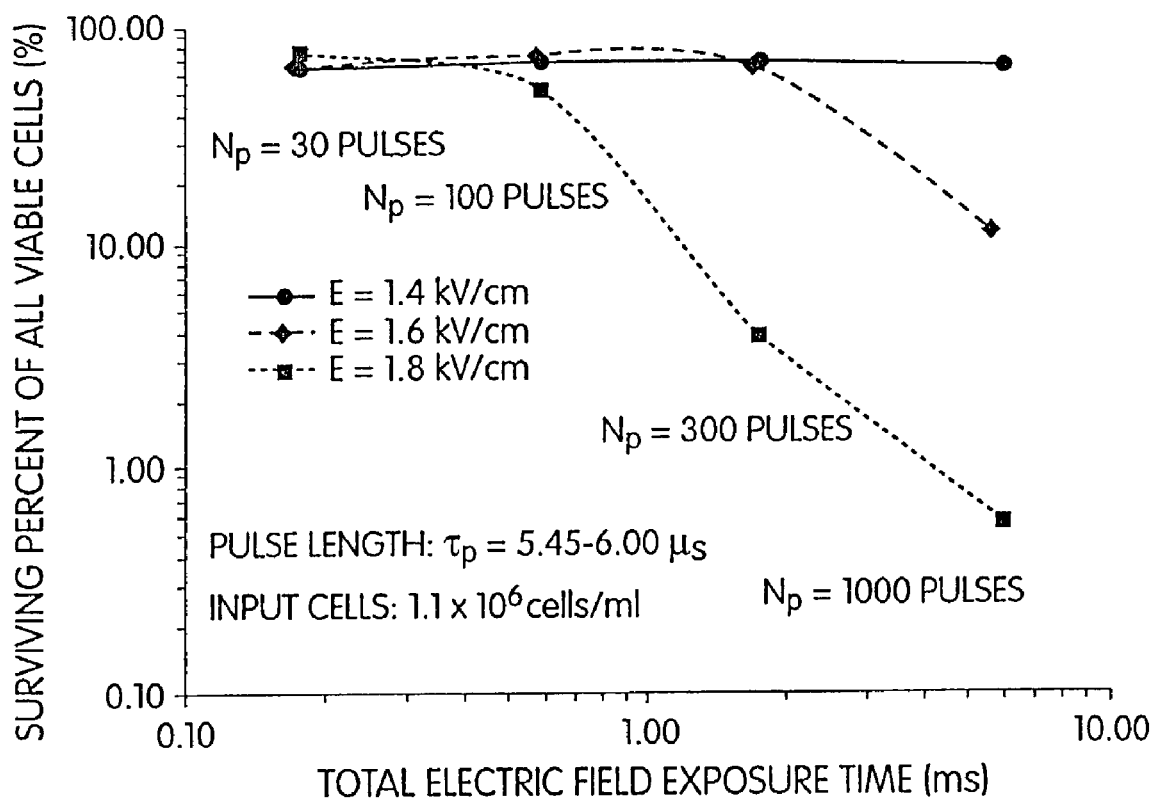
FIG. 11 is a graph showing surviving cells as a function of PEF electric field exposure time and magnitude for cells treated according to one embodiment of the invention.

FIG. 11 presents total surviving percent of all viable cells, on the y-axis, as a function of total electric field exposure time, for three different electric field strengths. These results indicate that PEF lethality, expressed as surviving percent, increased with increasing electric field strength and total electric field exposure time as predicted by Eq. 8. Further, FIG. 11 indicates that the onset of significant cell inactivation occurred at approximately 1.8 kV/cm. This measured threshold strength is in reasonable agreement with the threshold strength for the resting lymphocytes given in Table 2, which would be expected since the most abundant population of cells in the PBMC specimens were resting lymphocytes.

Figure 12A:
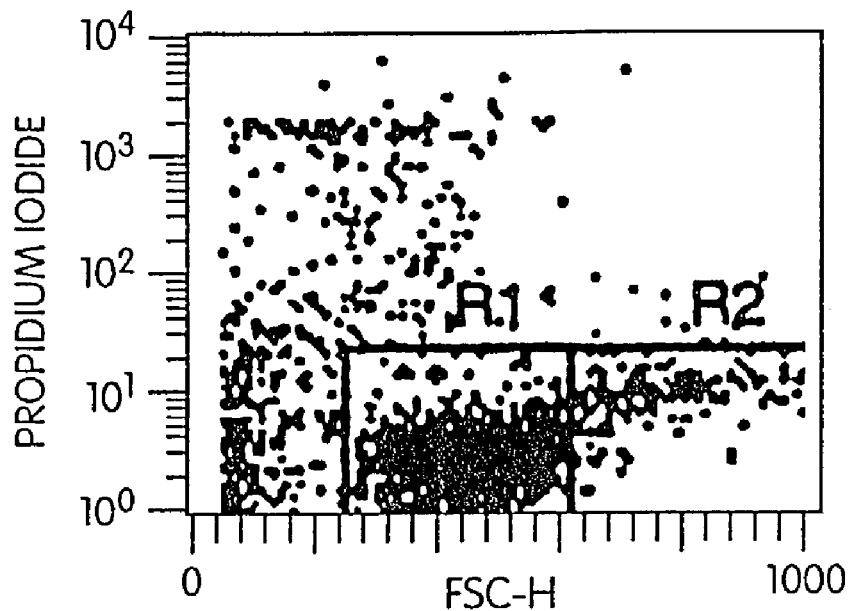
FIG. 12a is a viability scatter plot derived from flow cytometry data for a control cell specimen.
Figure 12B:
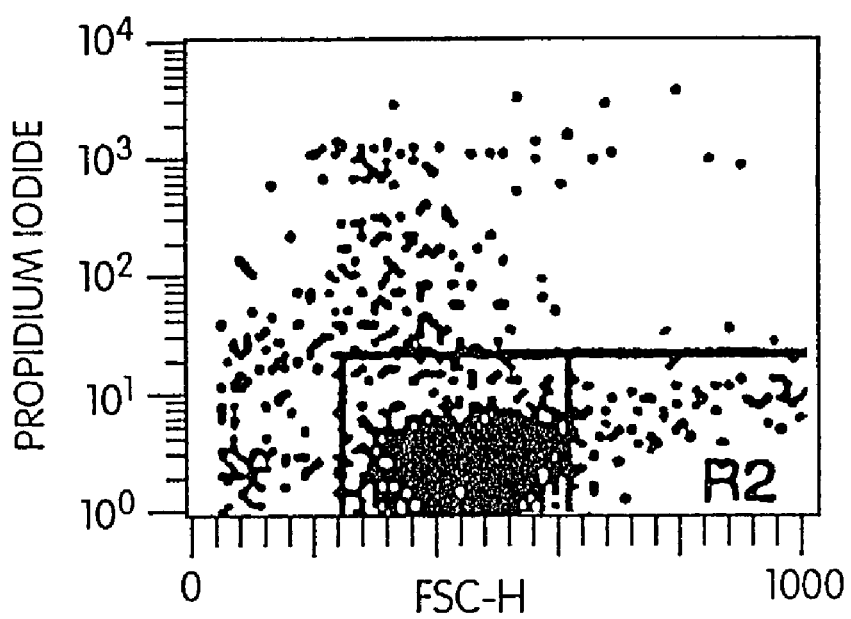
FIG. 12b is a viability scatter plot derived from flow cytometry data for a PEF-treated cell specimen for cells treated according to one embodiment of the invention.
Figure 12C:
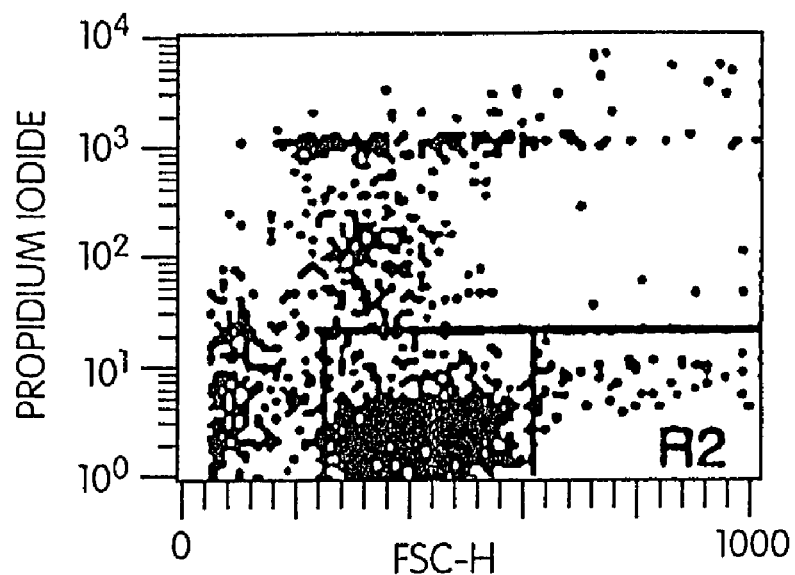
FIG. 12c is a viability scatter plot derived from flow cytometry data for a PEF-treated cell specimen for cells treated according to one embodiment of the invention.
Figure 12D:
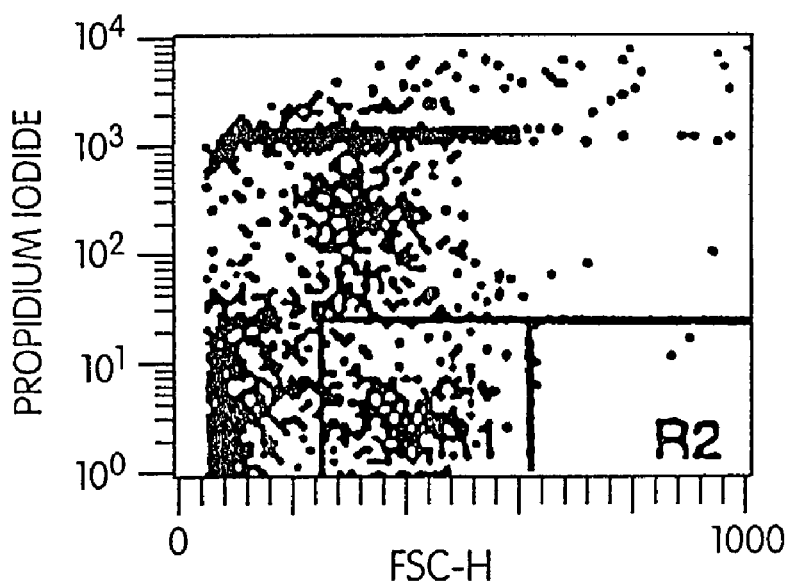
FIG. 12d is a viability scatter plot derived from flow cytometry data for a PEF-treated cell specimen for cells treated according to one embodiment of the invention.

FIGS. 12a-12d show viability scatter plots that were derived from flow cytometry assays of the specimens for this case. The results given in these figures were generated for specimens exposed to a fixed electric field strength of 1.8 kV/cm. FIG. 12a shows the scatter plot for the test cell control specimen, whereas FIGS. 12b, 12c, and 12d show the scatter plots for 30, 100, and 300 applied electric field pulses respectively. The y-axes in these figures show relative propidium iodide (PI) intensity, and the x-axes show forward scattered (FSC-H) light angles, which are proportional to cell size. High PI values are indicative of nonviable cells. High FSC-H values are large cells. Regions represented by R1 and R2 in these figures correspond to viable cells. In FIG. 12a, the viable cells in R1 and R2 form a pattern that looks like a pan with a handle. It can be seen that as one scans from FIGS. 12a to 12d, the handle (i.e. viable cells in R2) disappears. These figures also show that the fraction of cells that scored high for PI increased with increasing total electric field exposure time (total number of applied pulses). Thus, for a field strength of 1.8 kV/cm, FIGS. 12a-12d indicate that the applied PEFs were selectively killing the larger cells.

Figure 13A:
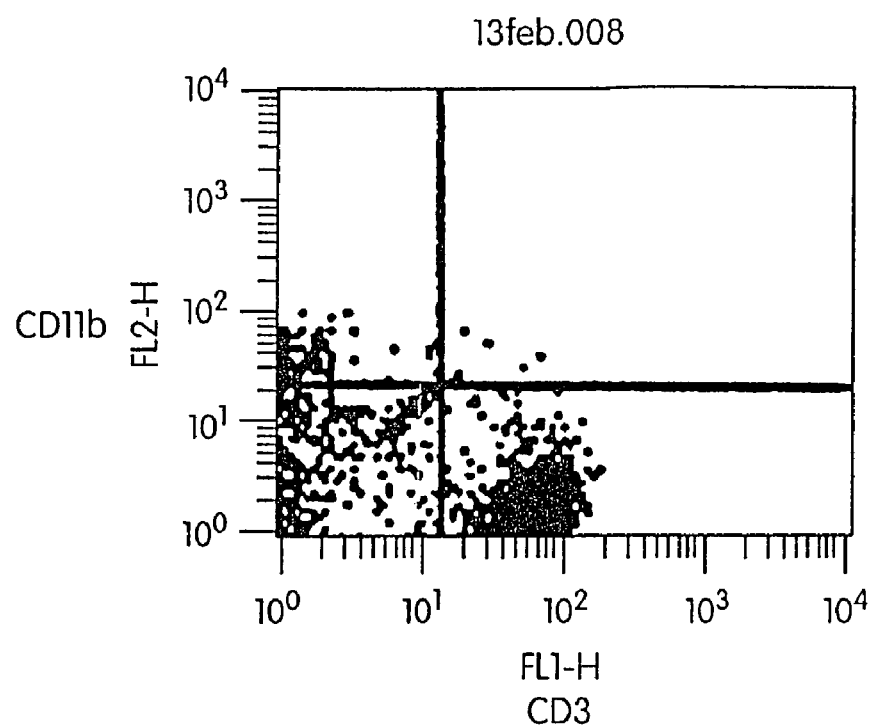
FIG. 13a is a scatter plot of data obtained with flow cytometry for a control cell suspension.
Figure 13B:
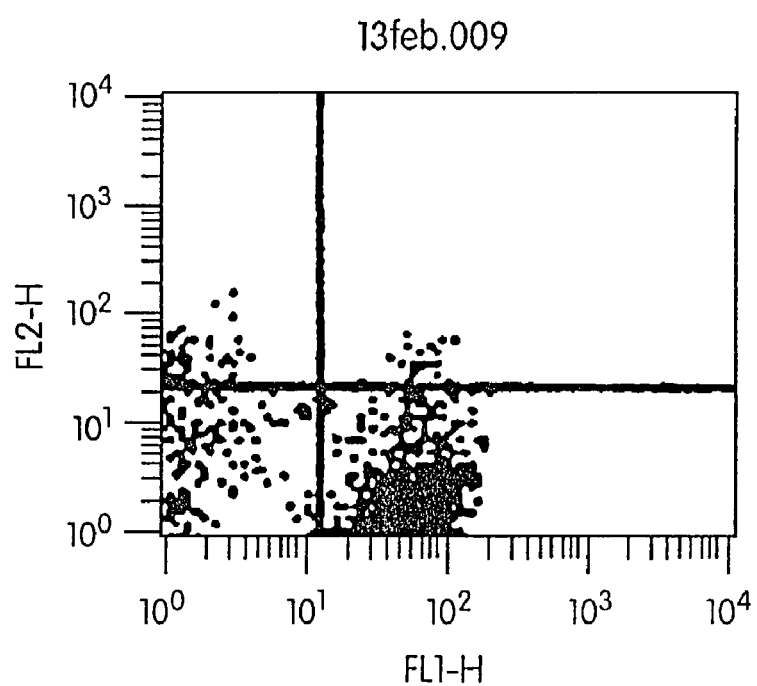
FIG. 13b is a scatter plot of data obtained with flow cytometry for a PEF-treated cell suspension for cells treated according to one embodiment of the invention.
Figure 13C:
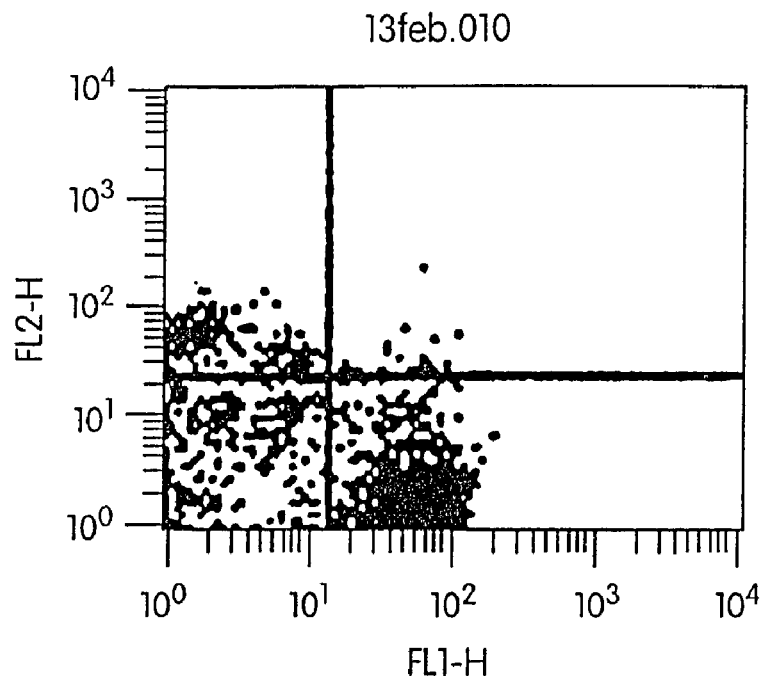
FIG. 13c is a scatter plot of data obtained with flow cytometry for a PEF-treated cell suspension for cells treated according to one embodiment of the invention.
Figure 13D:
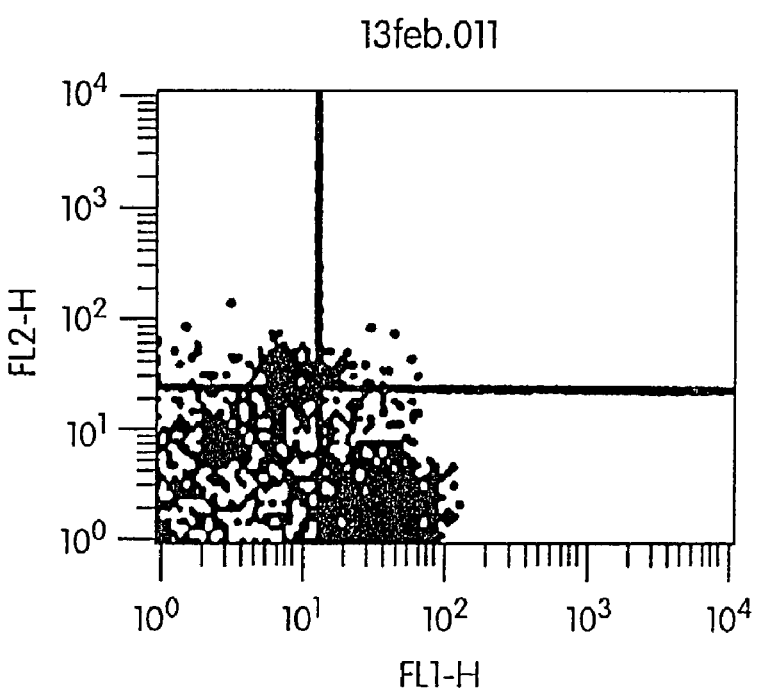
FIG. 13d is a scatter plot of data obtained with flow cytometry for a PEF-treated cell suspension for cells treated according to one embodiment of the invention.

FIGS. 13a-13c present CD11b/CD3 flow cytometry scatter plots for the corresponding specimens shown in FIGS. 12a-12d. FIG. 13a shows results for the control specimen. Relative intensity of CD11b staining is shown on the y-axes, and relative intensity of CD3 staining is shown on the x-axes. FIGS. 13b, 13c, and 13d correspond to PEF treated specimens that received 30, 100, and 300 electric field pulses of 1.8 kV/cm strength respectively. Cells scoring high for CD11b are predominately monocytes. Those scoring high for CD3 are predominately T-cells. Based on Table 2, the T-cells (a subset of lymphocytes) are typically about 7 μm in size, whereas the monocytes are typically about 15 μm in size. The upper left quadrant of FIG. 13a displays a distinct monocyte population that diminishes significantly as one scans from FIG. 13a to FIG. 13b to FIG. 13c and finally to FIG. 13d. In contrast, however, the T-cell population (lower right quadrant) has not been reduced as significantly as the monocyte population. Thus, the 1.8 kV/cm PEFs have selectively depleted the monocyte cells while preserving a significant fraction of the T-cells.

Case 2. PEF Enrichment of Lymphocytes Over Monocytes

The ability of PEFs to enrich a PBMC specimen in lymphocytes by selective inactivation of the larger monocytes was demonstrated in this case. The stock cell suspension contained PBMCs suspended in IMDM at a concentration of $1.5 \times 10^6$ cells/ml. The pulsing medium was of standard physiological ionic strength. The input cells and stock cell suspension were prepared as previously described. Type A test cells were used for the Case 2 trials. Pulsed electric fields, having strengths in the range 1.2-1.6 kV/cm, were applied to the specimens. The total electric field exposure times were in the range 0.15-5.70 ms, and the electric field pulse length was about 5.17+/−0.3 μs (FWHM). The total electric field exposure time was varied over the noted range by varying the number of applied electric field pulses over a range of 30-1000 pulses. The single pulse energy deposited to the test cells ranged from 0.36-0.77 J/pulse. The electric field pulses were applied at 1 Hz. The end blocks of the test cells were maintained at 35° C.+/−0.2° C. Based on Eqs. 14, 14a, and 14b, the average midplane temperature varied over the range 35.1-35.3° C. and the temperature jump per electric field pulse varied over the range 0.02-0.04° C. One stock cell control specimen and one test cell control specimen were prepared before commencing PEF treatments, and one test cell control specimen was prepared after all PEF treatments had been performed for the test day in question. The control and PEF treated specimens (about 5 ml EACH) were placed in 15 ml centrifuge tubes after preparation, to which an approximately equal volume of IMDM was added as previously described. These specimens were then analyzed by flow cytometry for enumeration of viable cell types and numbers as also previously described.

Figure 14:
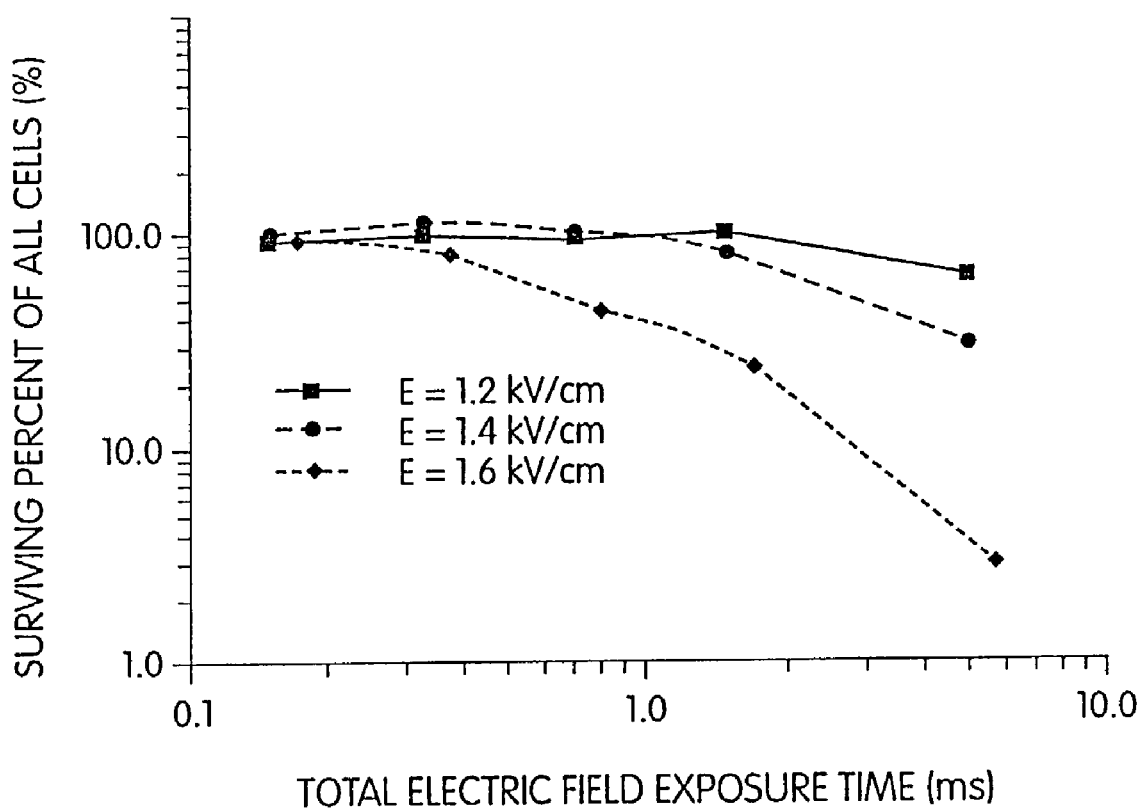
FIG. 14 is a graph showing surviving cells as a function of PEF electric field exposure time and magnitude for cells treated according to one embodiment of the invention.

The data in FIG. 14 is presented in the same format as shown previously in FIG. 11. The results indicate that PEF lethality, inversely proportional to surviving percent, increased with increasing electric field strength and total electric field exposure time as predicted by Eq. 8. The results presented in this figure exhibit the same trends as the data presented FIG. 11 for Case 1.

Using light scatter, viability stain gating, and CD3 and CD13 antibody fluorescence, viable lymphocyte and monocyte cells populations were enumerated independently. FIGS.

Figures 15A, 15B, 15C, 15D, 15E, 15F, 15G, 15H, 15I, 15J:
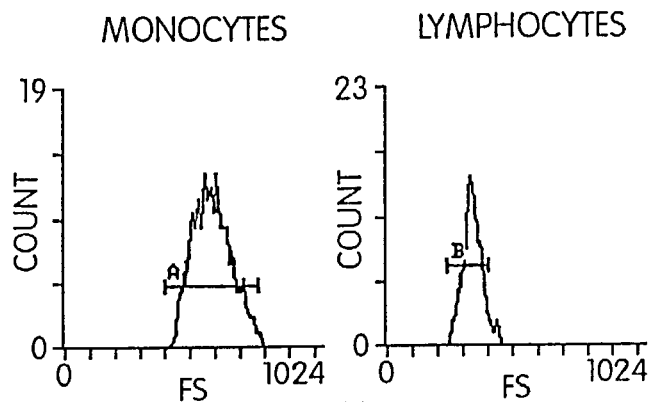
FIG. 15a is a forward scatter histogram derived from flow cytometry data for monocytes in a control cell suspension.
FIG. 15b is a forward scatter histogram derived from flow cytometry data for monocytes in a PEF-treated cell suspension for cells treated according to one embodiment of the invention.
FIG. 15c is a forward scatter histogram derived from flow cytometry data for monocytes in a PEF-treated cell suspension for cells treated according to one embodiment of the invention.
FIG. 15d is a forward scatter histogram derived from flow cytometry data for monocytes in a PEF-treated cell suspension for cells treated according to one embodiment of the invention.
FIG. 15e is a forward scatter histogram derived from flow cytometry data for monocytes in a PEF-treated cell suspension for cells treated according to one embodiment of the invention.
FIG. 15f is a forward scatter histogram derived from flow cytometry data for lymphocytes in a control cell suspension.
FIG. 15g is a forward scatter histogram derived from flow cytometry data for lymphocytes in a PEF-treated cell suspension for cells treated according to one embodiment of the invention.
FIG. 15h is a forward scatter histogram derived from flow cytometry data for lymphocytes in a PEF-treated cell suspension for cells treated according to one embodiment of the invention.
FIG. 15i is a forward scatter histogram derived from flow cytometry data for lymphocytes in a PEF-treated cell suspension for cells treated according to one embodiment of the invention.
FIG. 15j is a forward scatter histogram derived from flow cytometry data for lymphocytes in a PEF-treated cell suspension for cells treated according to one embodiment of the invention.

15a-15j present the results in forward scatter histogram format with relative numbers of cells on the y-axes and size on the x-axes. FIGS. 15a and 15f show the monocyte (FIG. 15a) and lymphocyte (FIG. 15f) histograms for the control specimens. Similarly, FIGS. 15b and 15g, 15c and 15h, 15d and 15i, and 15e and 15j show the monocyte and lymphocyte histograms, respectively within each pair of Figs., for an electric field strength of 1.4 kV/cm and total electric field exposure times of 0.15 ms (30 pulses, FIGS. 15b and 15g), 0.33 ms (65 pulses, FIGS. 15e and 15h), 0.70 ms (140 pulses, FIGS. 15d and 15i), 1.50 ms (300 pulses, FIGS. 15e and 15i). The size difference between the monocytes and lymphocytes can be inferred by considering the location of the corresponding distributions on the forward scatter axis: the monocytes are farther to the right (i.e. larger) relative to the lymphocytes (compare FIGS. 15a and 15f for example). Progressively comparing corresponding pairs of Figs. for related PEF treatment conditions and increasing electric field exposure times (i.e. comparing FIGS. 15a and 5f, then FIG. 15b and FIG. 15g, etc.), indicates that as total electric field exposure time increased, there was a large reduction in the number of monocytes, with only a minor reduction in the number of lymphocytes. (Note that the scale for the monocyte histograms changes from FIG. 15b to FIG. 15c, and again from FIGS. 15d to 15e). FIGS. 15a-15j clearly demonstrate the size selective inactivation characteristics of PEFs for this cellular system. It is also noteworthy that the steepness of the tail on the right hand side of the lymphocyte distributions increases with increasing electric field exposure time, an indication that the larger lymphocytes were inactivated before the smaller ones.

Figure 16:
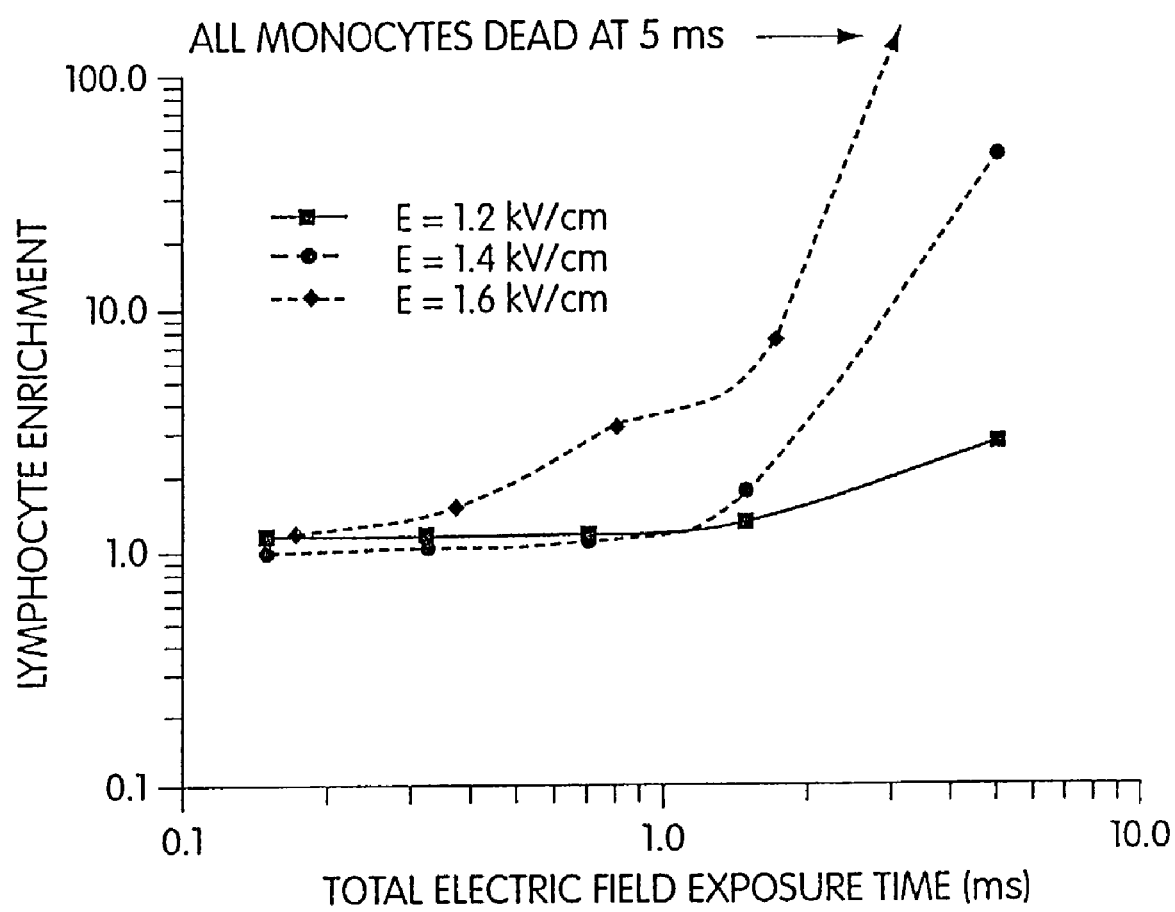
FIG. 16 is a graph showing lymphocyte enrichment as a function of electric field exposure time and magnitude for cells treated according to one embodiment of the invention.

The results for this case have been replotted in FIG. 16 as lymphocyte enrichment (y-axis) as a function of total electric field exposure time x-axis) for three different electric field strengths. Lymphocyte enrichment was defined as the ratio of lymphocytes to monocytes for the control specimen divided by this ratio for the PEF treated specimens. This figure clearly shows that lymphocyte enrichment increased with both electric field strength and total electric field exposure time. At a field strength of 1.6 kV/cm and a total electric field exposure time of ~5 ms, essentially no monocytes were detected by flow cytometry thereby yielding an essentially infinite value for lymphocyte enrichment.

Case 3. PEF Enrichment of Stem Cells in PBPC Preparations

The ability of PEFs to enrich PBPC specimens for hematopoietic stem cells by selective inactivation of the larger cells present in heterogeneous PBPC mixtures was demonstrated in this case. The stock cell suspension contained PBPCs suspended in a low ionic strength pulsing medium (10% v/v PBS, 90% v/v isotonic sucrose solution) at a concentration of 6.6× $10^6$ cells/ml. The PBPCs were harvested from patients, by leukopheresis, that had received G-CSF treatments as previously discussed. Prior to PEF treatment, the resting lymphocytes in the PBPC preparation were activated, as previously discussed, thereby stimulating these cells to their active state which nearly doubled their size. Type A test cells were used for the Case 3 trials. Pulsed electric fields, having strengths of 1.7, 1.8, and 1.9 kV/cm, were applied to the specimens. The total electric field exposure time was 5.30 ms (1000 applied pulses), and the electric field pulse length was 5.30 µs (FWHM). The single pulse energy deposited in the test cells ranged from 0.11-0.15 J/pulse. The electric field pulses were applied at 1 Hz. The end blocks of the test cells were maintained at about 35° C.+/−0.2° C. Based on Eqs. 14, 14a, and 14b, the average midplane temperature varied from about 35.0-35.1° C., and the temperature jump per electric field pulse varied from about 0.005-0.007° C. One stock cell control specimen and one test cell control specimen were prepared before commencing PEF treatments, and one test cell control specimen was prepared after all PEF treatments had been performed The controls and PEF treated specimens (each about 5 ml) were placed in 15 ml centrifuge tubes after preparation, to which an equal volume of IMDM was added as previously described. The specimens were then analyzed by flow cytometry for cell identification and enumeration as previously described.

Figure 17:
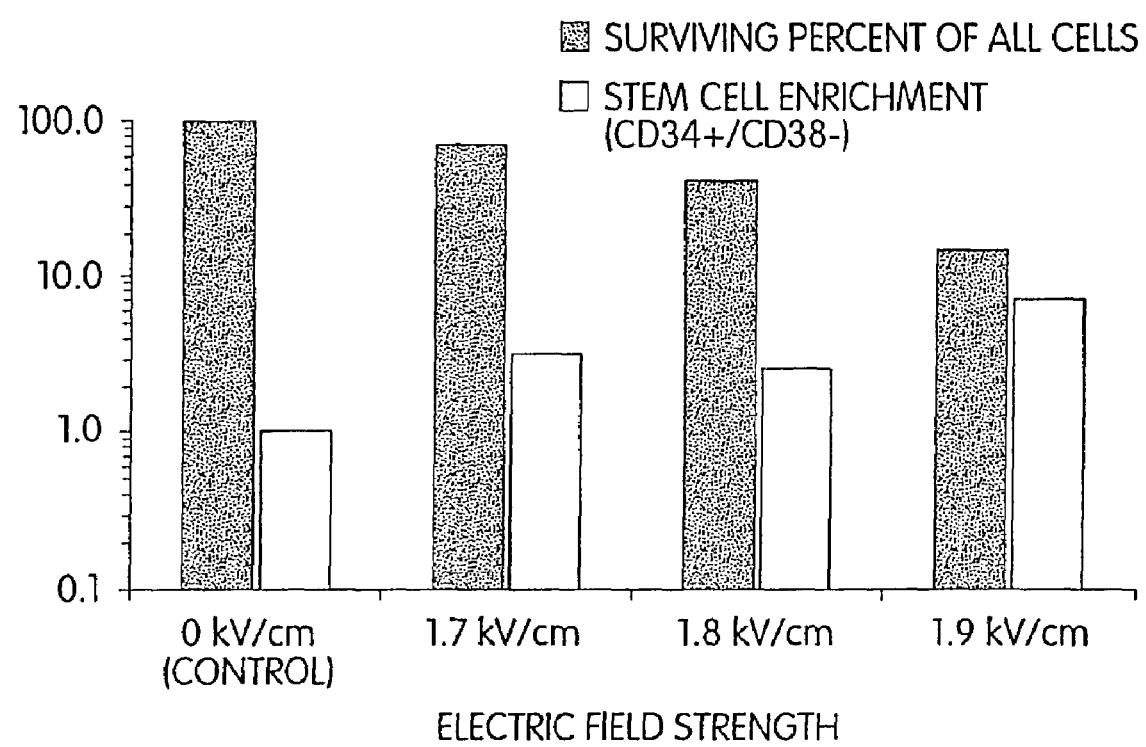
FIG. 17 is a bar chart showing surviving fraction of cells and stem cell enrichment as a function of electric field strength for cells treated according to one embodiment of the invention.

Using viability (TO-PRO-3) and CD34, and CD38 antibody staining, viable primitive progenitor cells were enumerated in the control and PEF treated specimens. Hematopoietic stem cells were identified as those viable cells that scored low for the viability stain, high for the CD34 fluorescence marker, and low for the CD38 marker (i.e., CD34+/CD38− or CD34 single positive cells). The results for this case are presented in FIG. 17 in bar chart format. The shaded bars in FIG. 17 correspond to the surviving percent of all cells in the suspension. The unshaded bars correspond to stem cell enrichment, which was defined as the ratio of viable stem cells to total viable cells in the PEF treated specimens normalized by the same ratio for the control specimens. FIG. 17 shows that the total surviving percent of cells decreased with increasing electric field strength. However, stem cell enrichment increased with increasing electric field strength. In fact, at 1.9 kV/cm, enrichment approached 1 log. Significantly, the enrichment increased inversely proportional to the decrease in total surviving percent. This indicates that the stem cell population was being preserved and demonstrates the ability of PEF's to enrich PBPC specimens for stem cells.

It should be re-emphasized that these results were obtained under conditions that were not optimized for stem cell enrichment. More specifically, the electric field waveform shape used for this case (see FIG. 10) was Gaussian in shape, rather than rectangular, and the length of the pulse (~5 µs) was very short. As discussed previously, the electric field waveform shape is preferably rectangular (with very short rise/fall times and with an essentially constant field strength between rise and fall) for obtaining more optimal size selectivity. Also, as discussed previously, short electric field pulses, such as the 5 µs pulses used in the present case are generally less effective for cell inactivation than pulse durations greater than about 10 µs.

Case 4. PEF Purging of CMK Tumor Cells in PBMCs

Figure 18A:
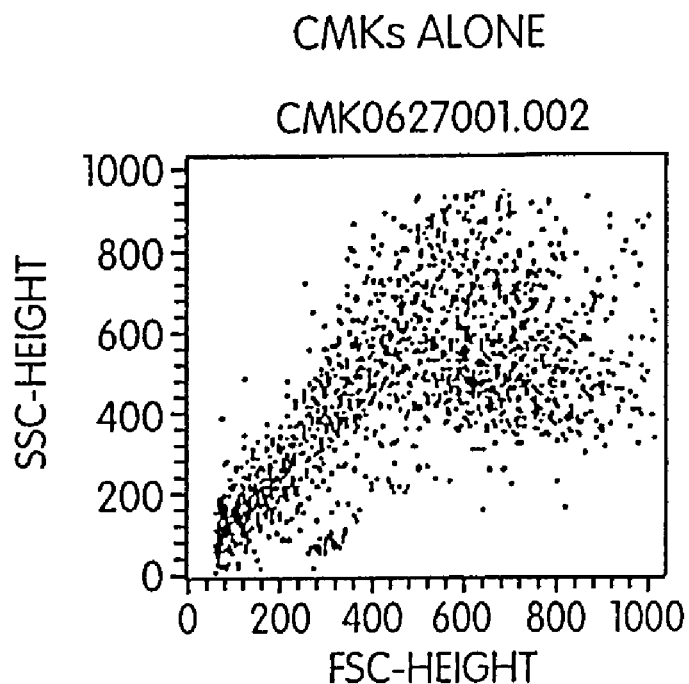
FIG. 18a is a light scatter plot derived from flow cytometry data for input CMK cells to be treated according to one embodiment of the invention.
Figure 18B:
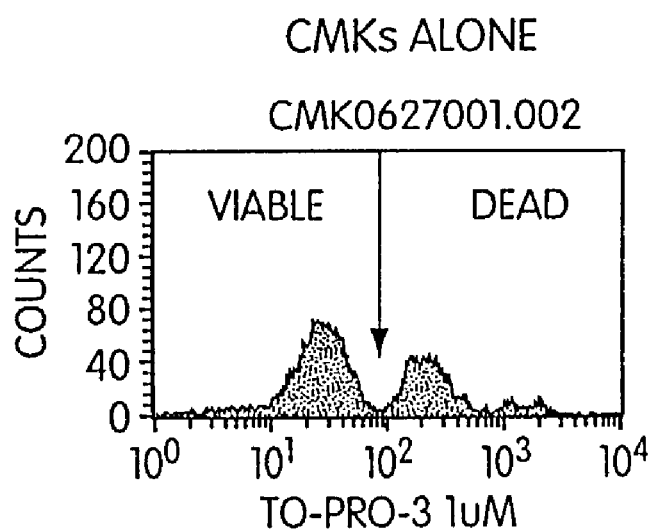
FIG. 18b is a viability stain histogram derived from flow cytometry data for input CMK cells to be treated according to one embodiment of the invention.
Figure 18C:
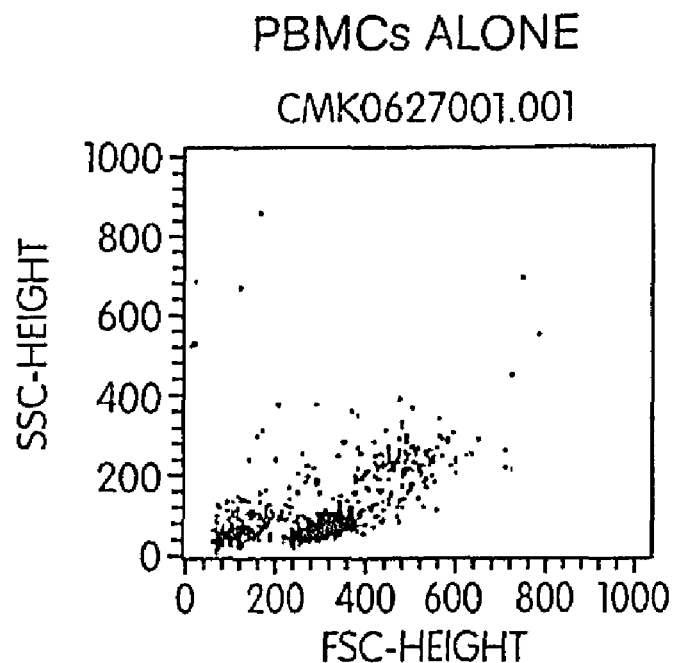
FIG. 18c is a light scatter plot derived from flow cytometry data for input PBMC cells to be treated according to one embodiment of the invention.
Figure 18D:
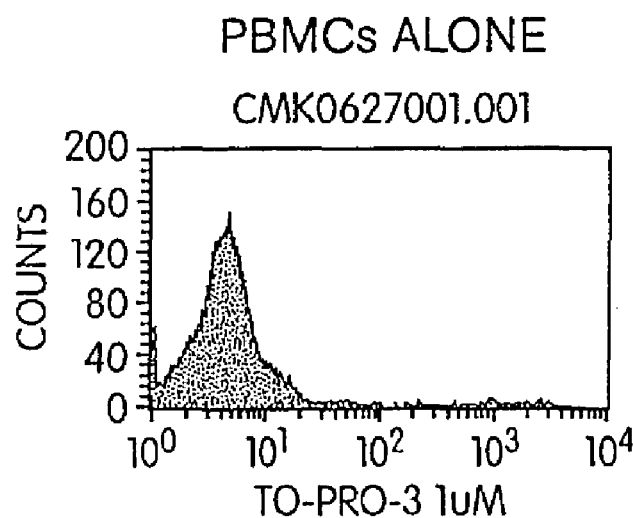
FIG. 18d is a viability stain histogram derived from flow cytometry data for input PBMC cells to be treated according to one embodiment of the invention.
Figure 18E:
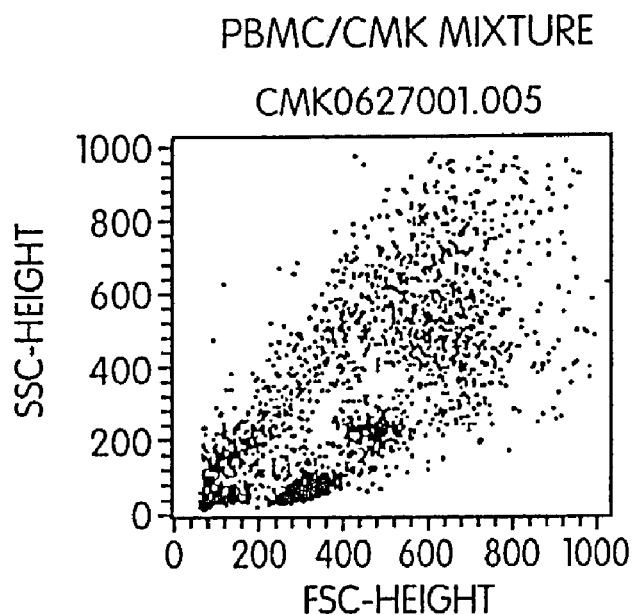
FIG. 18e is a light scatter plot derived from flow cytometry data for an input CMK/PBMC cell mixture to be treated according to one embodiment of the invention.
Figure 18F:
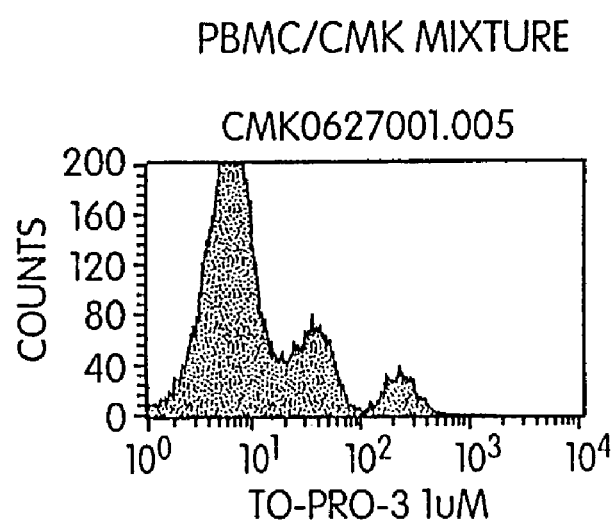
FIG. 18f is a viability stain histogram derived from flow cytometry data for an input CMK/PBMC cell mixture to be treated according to one embodiment of the invention.

This case demonstrates the ability of PEFs to purge PBMC suspensions of tumor cells. The stock cell suspension included PBMCs and CMK tumor cells suspended in a low ionic strength pulsing medium (10% v/v PBS, 90% v/v isotonic sucrose solution) at 2.5×$10^6$ cells/ml. The CMK tumor cells represented about 14% of the total number of cells. The CMKs are a megakaryocyte line whose size approximates epithelial tumor cell types. The PBMCs and CMKs were prepared as previously described. Type A test cells were used for the Case 4 trials. Pulsed electric fields, having strengths in the range 1.2-1.8 kV/cm, were applied to the specimens. The total electric field exposure time was 3.6 ms (1000 applied pulses), and the electric field pulse length was 3.6 µs (FWHM). The single pulse energy deposited to the test cells ranged from 0.04-0.10 J/pulse, and the electric field pulses were applied at 1 Hz. The end blocks of the test cells were maintained at 35° C.+/−0.2° C. Based on Eqs. 14, 14a, and 14b, the average midplane temperature varied from about 35.02-35.04° C. and the temperature jump per electric field pulse varied from about 0.002-0.005° C. One stock cell control specimen and one test control specimen were prepared before commencing PEF treatments, and one test cell control specimen was prepared after all PEF treatments had been performed. The controls and PEF treated specimens (each about 5 ml) were placed in 15 ml centrifuge tubes after preparation, to which an approximately equal volume of IMDM was added as previously described. The specimens were then analyzed by flow cytometry for cell identification and enumeration as previously described. FIGS. 18a-18f show the flow cytometry data from the analysis of the input cells for this case. FIGS. 18a, 18c, and 18e are the light scatter plots (no viability stain gating) for the CMK cells alone, the PBMCs alone, and the CMK/PBMC mixture, respectively. FIGS. 18b, 18d, and 18f are viability stain histograms for the CMKs alone, the PBMCs alone, and the CMK/PBMC mixture respectively. Cells staining for the viability stain (TO-PRO-3) with an intensity greater than $10^2$ were considered dead. FIG. 18b indicates that the CMK cells had a component (i.e. that population above $10^2$ on the x-axis) that was either dead or represented cell debris. These dead cells or debris showed up in the light scatter plot (FIG. 18a) as a band of dots that extend up and to the right from the origin. The viable CMK population appeared as a cluster of dots that is centered vertically in FIG. 18a and slightly to the right of center horizontally. FIG. 18c indicates that were three clusters of dots for the PBMCs. The cluster near the origin represents fine cell debris. The next cluster to the right represents the lymphocyte population, and the cluster furthest to the right represents the monocyte population. The lymphocyte, monocyte, and CMK clusters are evident in FIG. 18e.

Figure 19A:
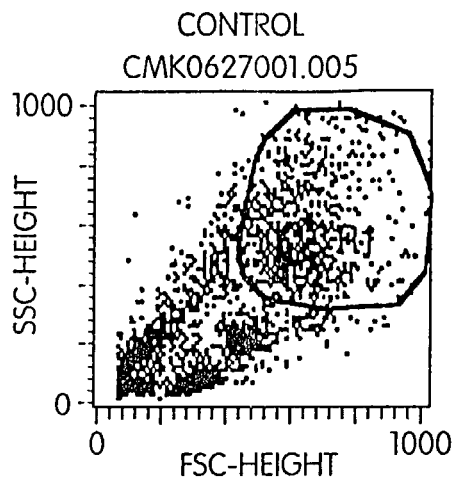
FIG. 19a is a light scatter plot derived from flow cytometry data for a control cell specimen containing a CMK/PBMC cell mixture.
Figure 19B:
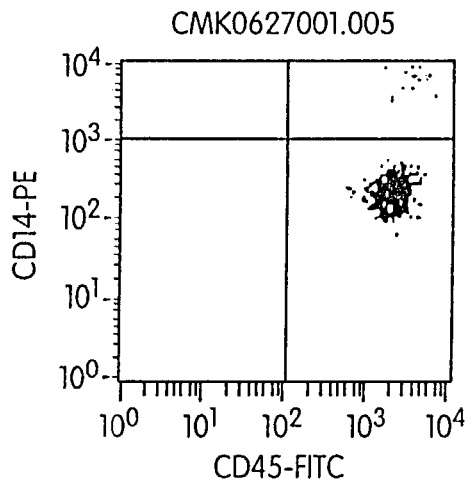
FIG. 19b is a bivariate plot derived from flow cytometry data for a control cell specimen containing a CMK/PBMC cell mixture.
Figure 19C:
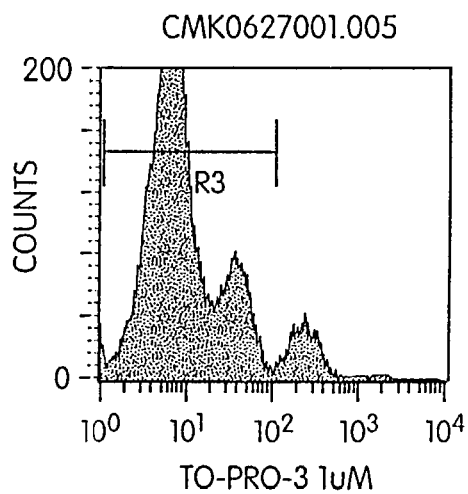
FIG. 19c is a viability histogram derived from flow cytometry data for a control cell specimen containing a CMK/PBMC cell mixture.
Figure 19D:
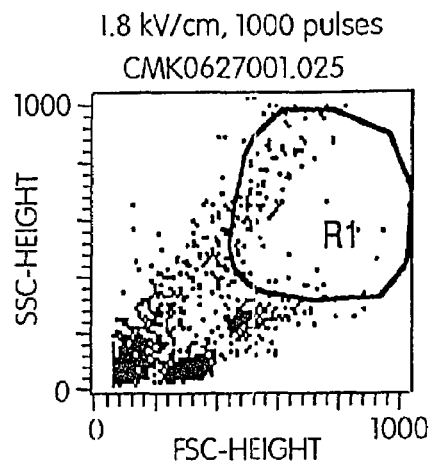
FIG. 19d is a light scatter plot derived from flow cytometry data for a PEF-treated cell specimen containing a CMK/PBMC cell mixture for cells treated according to one embodiment of the invention.
Figure 19E:
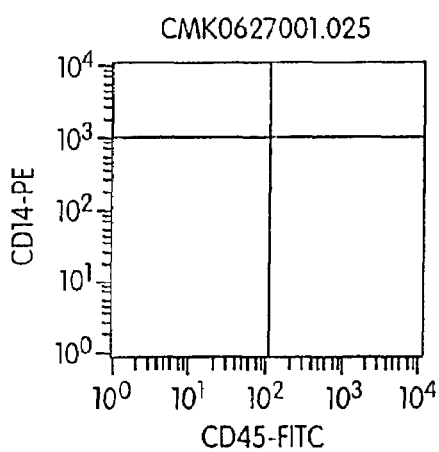
FIG. 19e is a bivariate plot derived from flow cytometry data for a PEF-treated cell specimen containing a CMK/PBMC cell mixture for cells treated according to one embodiment of the invention.
Figure 19F:
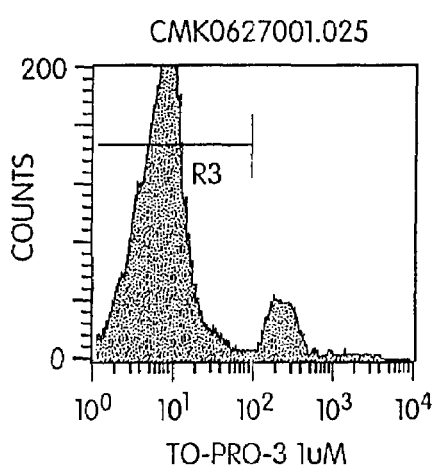
FIG. 19f is a viability histogram derived from flow cytometry data for a PEF-treated cell specimen containing a CMK/PBMC cell mixture for cells treated according to one embodiment of the invention.

FIGS. 19a-19f qualitatively illustrate the effect of applying 1000 electric field pulses, each with a strength of 1.8 kV/cm, to the CMK/PBMC mixture. FIGS. 19a, 19b, and 19c are a light scatter plot, CD14/CD45 bivariate plot, and TO-PRO-3 viability histogram, respectively for the control specimen. FIGS. 19d, 19e, and 19f present the same corresponding information as FIGS. 19a, 19b, and 19c respectively, for the specimen treated with 1000 electric field pulses, each having a strength of 1.8 kV/cm. As in FIG. 18e, the lymphocyte, monocyte, and CMK populations are evident in FIG. 19a. Circled region R1 (in FIGS. 19a and 19d) enclose the CMK population. Bracketed region R3 (in FIGS. 19c and 19f) defines viable cells as judged by TO-PRO-3 viability staining intensity. Scatter plots shown in FIGS. 19b (control) and 19e (PEF treated specimen) were gated on both R1 and R3, so the cells appearing in these two figures represent viable cells in the R1 light scatter compartment, which is dominated by the CMK tumor cells. The lower right quadrant of FIG. 19b shows a well defined CMK population. The upper right quadrant, however, shows that the R1 region also contained a small number of monocytes. FIG. 19e shows that both the CMKs and monocytes were eliminated by application of 1000 electric field pulses of 1.8 kV/cm strength. However, the light scatter plot (FIG. 19d) for the PEF treated specimen indicates that the specimen still contained healthy lymphocyte and monocyte populations. The change in the TO-PRO-3 viability histograms (FIG. 19c and FIG. 19f) also indicates that only the CMK population had been affected by PEF treatment (the central peak in FIG. 19c, which is missing in FIG. 19f corresponds to the CMK population, which was derived by considering FIG. 18b).

Figure 20A:
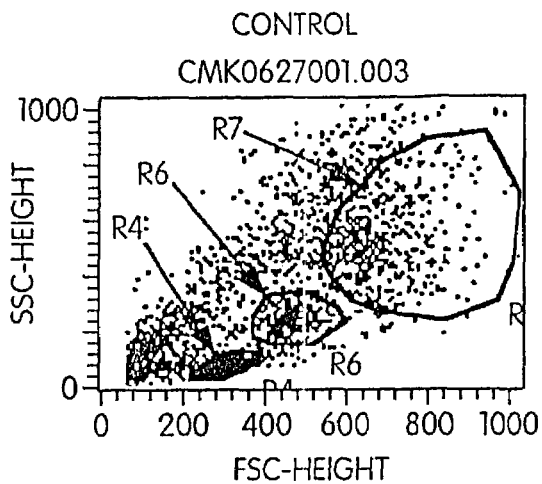
FIG. 20a is a light scatter plot derived from flow cytometry data for a control cell specimen containing a CMK/PBMC cell mixture.
Figure 20B:
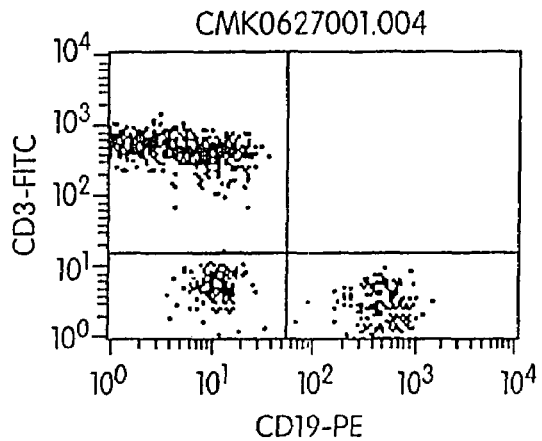
FIG. 20b is a bivariate plot derived from flow cytometry data for a control cell specimen containing a CMK/PBMC cell mixture.
Figure 20C:
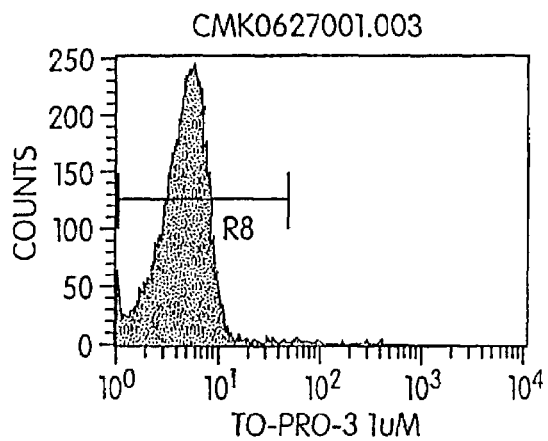
FIG. 20c is a viability histogram derived from flow cytometry data for a control cell specimen containing a CMK/PBMC cell mixture.
Figure 20D:
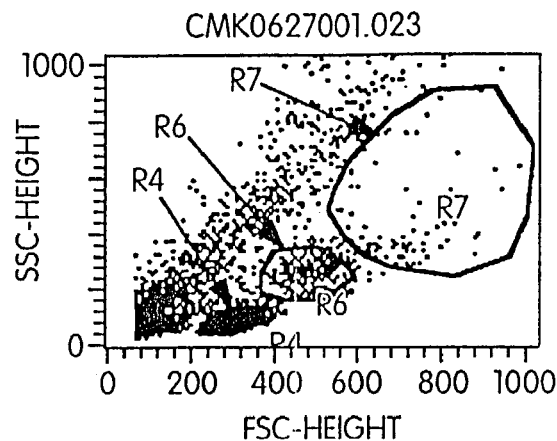
FIG. 20d is a light scatter plot derived from flow cytometry data for a PEF-treated cell specimen containing a CMK/PBMC cell mixture for cells treated according to one embodiment of the invention.
Figure 20E:
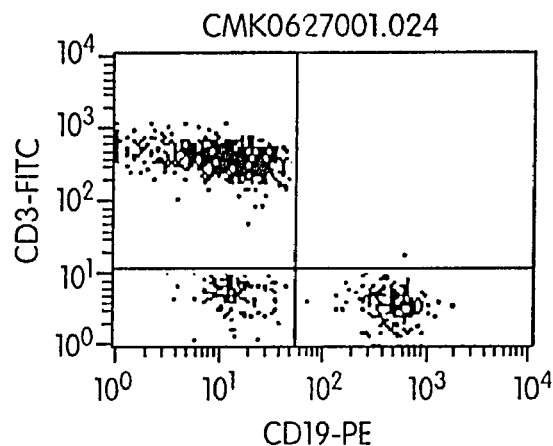
FIG. 20e is a bivariate plot derived from flow cytometry data for a PEF-treated cell specimen containing a CMK/PBMC cell mixture for cells treated according to one embodiment of the invention.
Figure 20F:
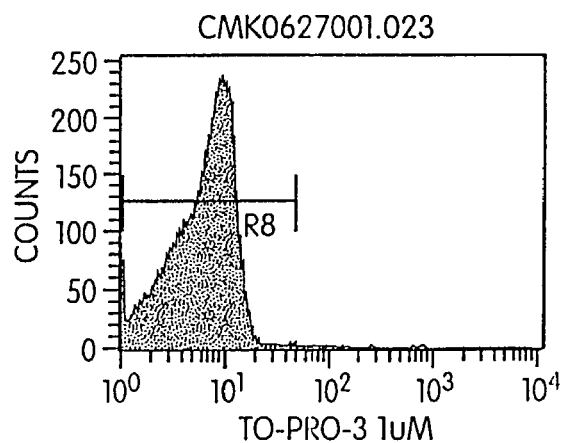
FIG. 20f is a viability histogram derived from flow cytometry data for a PEF-treated cell specimen containing a CMK/PBMC cell mixture for cells treated according to one embodiment of the invention.

FIGS. 20a-20f examine the effect of PEFs on the lymphocyte population. FIGS. 20a, 20b, and 20c are light scatter, CD3/CD19 bivariate plots, and TO-PRO-3 viability histograms, respectively, for the control specimen. FIGS. 20d, 20e, and 20f are the light scatter, CD3/CD19 bivariate plots, and TO-PRO-3 viability histograms, respectively, for the specimen that was treated with 1000 electric field pulses, each having a strength of 1.8 kV/cm. In FIG. 20a and FIG. 20d, regions labeled R4, R6, and R7 correspond to the light scatter compartments that enclose the lymphocytes, inonocytes, and CMKs, respectively. The TO-PRO-3 viability histograms in FIG. 20c and FIG. 20f were gated on R4, which means that only events in the lymphocyte compartments in the light scatter plots are displayed in FIG. 20c and FIG. 20f. FIGS. 20b and 20e are gated on R8 (the TO-PRO-3 viability ranges in either FIG. 20c or FIG. 20d) and R4 (the lymphocyte compartment in either FIG. 20a and FIG. 20d). Thus, FIG. 20b and FIG. 20e display only the viable cells from the lymphocyte light scatter compartments. The conjugate monoclonal antibody fluorescence marker CD3 stains T-cells, a subset of lymphocytes. The fluorescence marker CD19 stains B-cells. Thus, the upper left quadrants in FIG. 20b and FIG. 20e contain viable T-cells, whereas the lower right quadrants contain viable B-cells. Comparison of FIG. 20b and FIG. 20e indicates there was little difference in the abundance of viable T- and B-cells for the control and PEF treated specimens. However, FIGS. 19b and 19e clearly show that the CMK cells had been almost entirely eliminated under the same PEF conditions.

Figure 21:
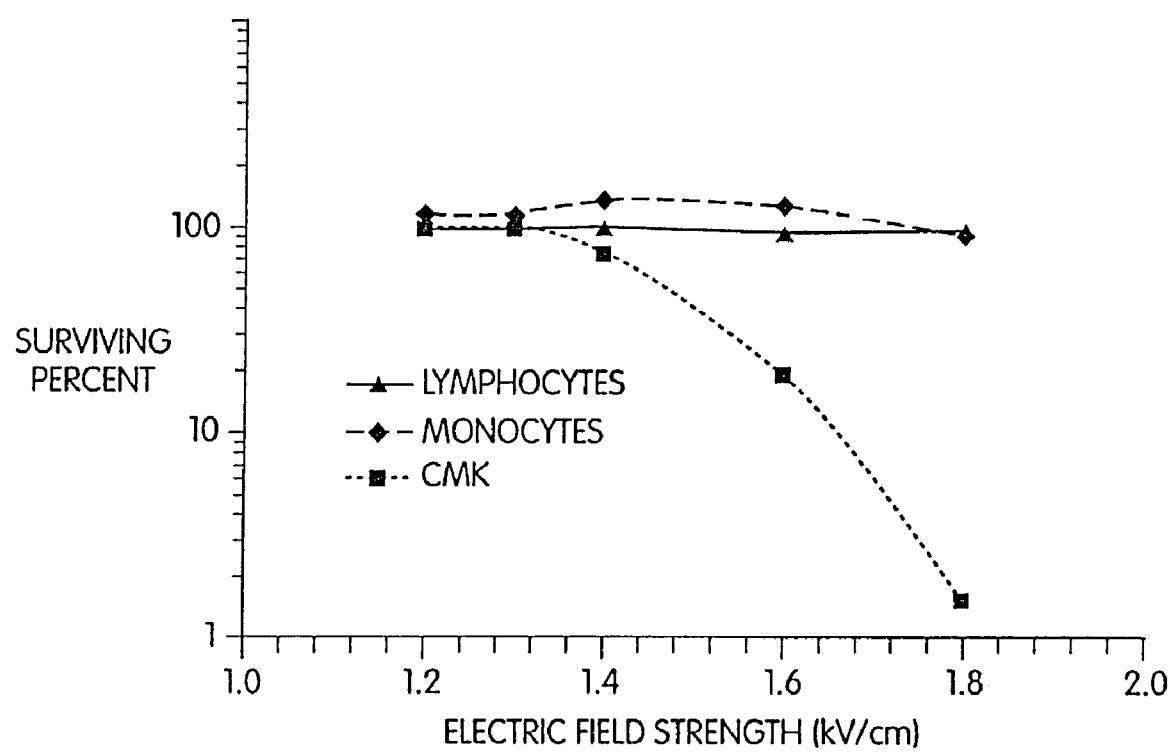
FIG. 21 is a graph showing surviving cells as a function of PEF electric field magnitude for three types of cells for cells treated according to one embodiment of the invention.

FIG. 21 presents the full set of data collected for this case. In this figure, the surviving percents of the relevant cell types (y-axis) are presented as a function of electric field strength (x-axis). Recall that the total electric field exposure time was constant for each field strength and was produced by applying 1000 electric field pulses. The total electric field exposure time was 3.6 ms. This figure clearly shows that an almost 2-log reduction in CMKs was achieved at 1.8 kV/cm without impacting the viability of the lymphocytes. Also, it is evident that the monocytes were just beginning to be affected at 1.8 kV/cm, since the monocyte surviving percent curve is beginning to decrease at this field strength. Comparing the PBMC total surviving percent curves presented in FIGS. 11 and 14 with the lymphocyte surviving percent curve in FIG. 21, shows the lethal effects of PEFs occurs at lower electric field strengths in FIGS. 11 and 14. As already indicated, the results presented in these examples have been acquired under non-optimized conditions. The differences in PEF efficacy found by comparing FIGS. 11 and 14 with FIG. 21 may be due to pulse length and pulsing medium ionic strength differences. The pulse length for the results in FIG. 21 was approximately 30% shorter than for the results in FIGS. 11 and 14. Further, the results in FIG. 21 were obtained using a low ionic strength pulsing medium, rather than a standard physiological ionic strength medium as used for the results presented in FIGS. 11 and 14.

As noted, the pulsing medium used for this case was a low ionic strength pulsing buffer (10% v/v PBS, 90% v/v isotonic sucrose solution). This low ionic strength pulsing medium was used for two reasons. First, as previously discussed, application of PEFs to cells in a low ionic strength pulsing medium, followed by resuspension in a standard physiological strength buffer, can lead to more extensive fragmentation of the of the PEF porated cells. It was observed during PEF cell selection experiments that post-PEF specimens that were treated with PEFs in a low ionic strength pulsing medium, followed by resuspension in a higher ionic strength medium, included far fewer trypan blue stained cells than when treated with PEFs under conditions where the pulsing buffer was of standard physiological ionic strength, even though the reductions in viable cells were comparable. This result indicates that the combination of a low ionic strength pulsing buffer and a higher ionic strength post-PEF resuspension buffer led to greater fragmentation of the PEF porated cells by colloidal osmotic cell lysis than for conditions where the pulsing buffer was of standard physiological ionic strength. Secondly, a lower ionic strength pulsing medium requires lower energy input to achieve the same electric field strengths.

Case 5. PEF Inactivation Characteristics of Breast Tumor Cells

The efficacy of PEF inactivation of breast tumor cells was investigated in this case. The stock cell suspension contained only breast tumor cells (MCF-7), which were suspended in a low ionic strength pulsing medium (10% v/v PB5, 90% v/v isotonic sucrose solution) at a total concentration of $1.2 \times 10^6$ cells/ml. The MCF-7s were prepared as previously described. Type B test cells were used for the Case 5 experiments. Pulsed electric fields, having field strengths in the range of 1.0-2.0 kV/cm were applied to the specimens. Two electric field pulse lengths were used for this case: 3.50 and 5.25 µs (FWHM). The total electric field exposure time was 3.5 ms (1000 applied pulses) for the shortest electric field pulse length, whereas the total electric field exposure time for the longest electric field pulse was 4.7 ms (900 pulses). The slight reduction in pulse number for the longer pulse length experiments was included to keep the total electric field exposure time for the longer pulse length experiments, based on the pulse length at 95% of the peak electric field strength, approximately the same as for the shorter pulse length experiments. The single pulse energy deposited to the test cells was in the range of 0.003-0.020 J/pulse. The electric field pulses were applied at 1 Hz. The end blocks of the test cells were maintained at about 35° C.+/−0.2° C. Based on Eqs. 14, 14a, and 14b, the average midplane temperature varied over the range from 35.01-35.04° C., and the temperature jump per electric field pulse varied over the range 0.001-0.007° C. One stock cell control specimen and test cell control specimen were prepared before commencing PEF treatments, and one test cell control specimen was prepared after all PEF treatments had been performed for each set of tests. The controls and PEF treated specimens (each about 0.72 ml) were placed in 15 ml centrifuge tubes, to which about 5 ml of IMDM was added as previously described. These specimens were then analyzed by flow cytometry for enumeration of viable MCF-7s, also as previously described.

Figure 22:
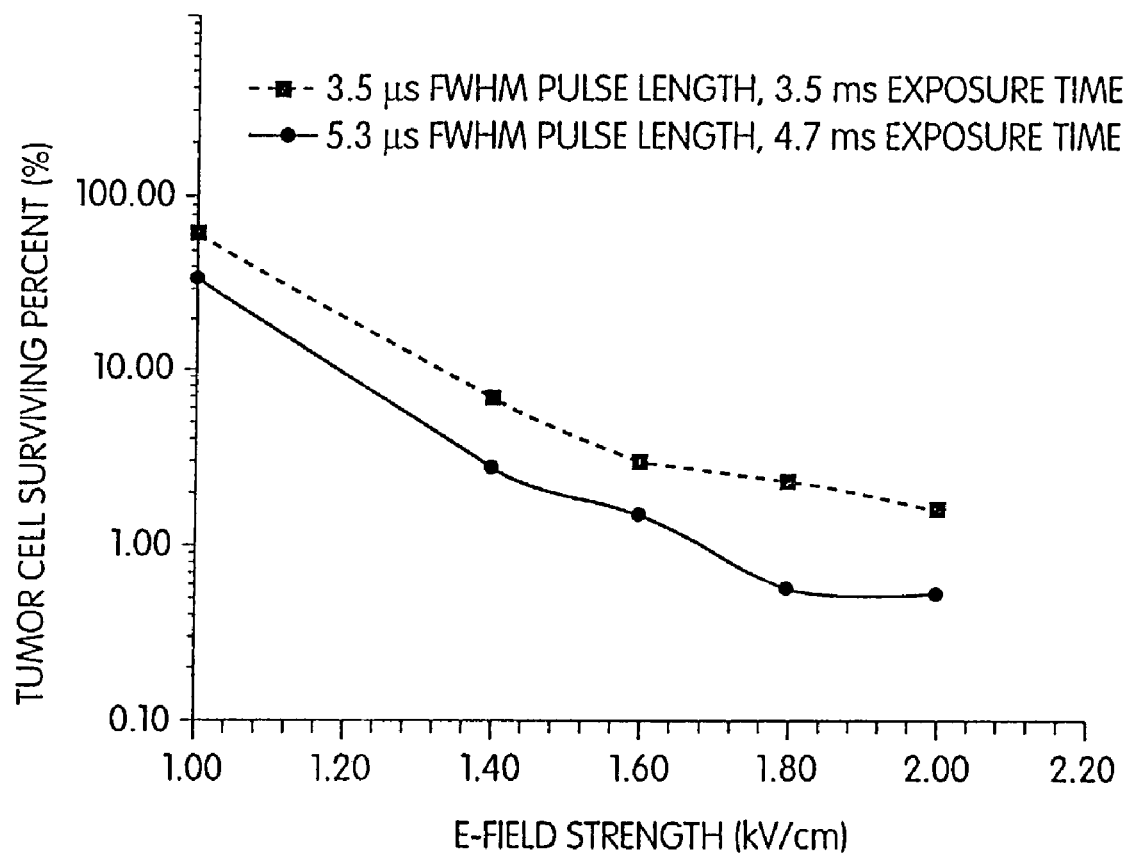
FIG. 22 is a graph showing surviving cells as a function of PEF electric field magnitude and pulse duration for cells treated according to one embodiment of the invention.

For this case, viable MCF-7s were identified as those cells that fluoresced dimly for both propidium iodide (PI) and Annexin-V stains. FIG. 22 presents results typical of PEF inactivation experiments using the MCF-7 cell line. More specifically, this figure illustrates the combined effect of increasing electric field pulse length and exposure time, as well as electric field strength. The curve shown by the dashed line represents data obtained by applying 1000 electric field pulses, each pulse having a 3.5 µs FWHM pulse length. The curve shown by the solid line represents data obtained by applying 900 electric field pulses, each pulse having a 5.3 µs FWHM pulse length. Thus, the total electric field exposure time for the dashed curve was 3.5 ms, whereas the total electric field exposure time for the solid curve was 4.7 ms.

FIG. 22 clearly shows that increasing PEF pulse length and exposure time resulted in increased tumor cell purging efficacy. Further, the 5.3 µs pulse length produced about a 2.3 log reduction in viable tumor cells. It is important to note that the 2.3 log reduction shown may significantly understate the efficacy of the PEF process. Optical microscopy indicated that the input cell population included clumps of agglomerated cells, each clump containing from about 3-10 cells. Thus, the number of viable MCF-7 cells in the control specimens, which were used to normalize the data for viable cells contained in the PEF-treated specimens, could be low by about a factor of 3-10. Thus, the surviving percents reported for the PEF-treated specimens could be high by a factor of 3-10. In addition, application of PEFs to this cell line had two effects: 1) the PEFs breakup the clumps of aggregated cells, and 2) inactivation of the cells. The breakup of cells was clearly observed by the increase in total events recorded by the cytometer. Total events were observed to increase by at least a factor of two once PEFs had been applied to a specimen. It is also believed the inflection points in the curves of FIG. 22 could be due to an increase in cell numbers due to disaggregation by the PEFs, followed by subsequent inactivation. Significantly, some of the cells in clumps will be shielded from the PEFs until such clumps are completely reduced to monodispersed cells. Once monodispersed, they can then be inactivated by the PEFs. Thus the presence of clumped cells in the cell suspension before treatment would imply that not all of the cells in the specimens experienced the same effective electric field exposure time. Thus, increasing the electric field pulse length, may be an effective way to lead to more efficient PEF clump disaggregation, which, in turn, could allow the use of lower field strengths and possibly shorter exposure times to achieve inactivation of cells that tend to clump, like the MCF-7 tumor cells. The MCF-7 tumor cell inactivation results presented here show that at least a 2.3 log reduction in this breast cancer line was achieved at PEF conditions which led to a 1 log enrichment of stem cells, without significant loss of viable stem cells, in Case 3 presented above.

Case 6: Enzymatic Removal of a Glycocalyx Membrane Layer

A small fraction of the cells within a given epithelial cell line, such as the MCF-7 line, secrete a mucopolysaccharide (mucin), which can coat the cell plasma membrane. This mucin coat can function to increase the effective thickness of the membrane of these cells, which can, in turn, require higher electric field strengths for their inactivation. The inventors have experimentally determined, using standard mucin stains and optical microscopy, that a fraction of the MCF-7 cells have a mucin coat and that the coat can be removed by enzyme digestion. To achieve this, the MCF-7s were subjected to a hyaluronidase digestion protocol just prior to their suspension in the pulsing medium. The mucin digestion protocol involved resuspending the trypsinized cells in a digestion solution (500 ug/ml hyaluronidase, Sigma, H4272 30 mg; 94 mM potassium phosphate monobasic, Sigma, P8416; 6 mM Sodium phosphate dibasic, Sigma, S-5136) and incubating the solution for 30 minutes at 37° C. Using standard techniques for mucin staining under optical microscopy it was found that this digestion protocol essentially entirely removed the extracellular mucin coats.

While the invention has been shown and described above with reference to various embodiments and specific examples, it is to be understood that the invention is not limited to the embodiments or examples described and that the teachings of this invention may be practiced by one skilled in the art in various additional ways and for various additional purposes.

What is claimed is:

1. A system for creating, from a biological sample having a given cell population of at least a first and a second cell type, a suspension containing a viable subpopulation of said given cell population, the system including:

a generating mechanism configured to generate an electric field of a selected, essentially uniform magnitude for a selected duration sufficient to irreversibly porate a substantial fraction of cells of said first cell type while maintaining substantially viable cells of said second cell type; and a treatment cell comprising an electrode electrically connected to said generating mechanism and adapted to contain a cell suspension, wherein said electrode is constructed of porous graphite and sealed with pyrolytic carbon.

2. A system as in claim 1, wherein said generating mechanism includes an electric pulse driver.

3. A system as in claim 1, wherein said generating mechanism generates a magnetic field that induces said electric field.

4. A system as in claim 1, wherein said treatment cell is constructed and arranged to provide a treatment volume for batch treatment of a cell suspension therewithin.

5. A system as in claim 1, wherein said system includes a cooling system constructed and arranged to control the operating temperature of said treatment cell.

6. A system as in claim 5, further comprising a cooling fluid contained within the cooling system.

7. A system as in claim 1, wherein said treatment cell is constructed and assembled without the need for supplemental seals.

8. A system as in claim 1, further including a mechanism operative on the suspension to remove inactivated cells and cell debris therefrom.

9. A system as in claim 1, wherein said first and second cell types have a difference in at least one property affecting a characteristic electroporation threshold.

10. A system as in claim 9, wherein said property affecting a characteristic electroporation threshold of said selected viable subpopulation is an average characteristic cell size that is less than or equal to a predetermined threshold size, said predetermined threshold size being less than the average characteristic cell size of said first cell type.

11. A system as in claim 1, wherein the average characteristic cell size of said first cell type is greater than the average characteristic cell size of said second cell type.

12. A system as in claim 1, wherein the treatment cell is constructed and arranged such that, when said electric field is applied to said biological sample by said generating mechanism, at least 90% of the cells of said first cell type are selectively inactivated while a substantial fraction of the cells of said second cell type remain substantially viable, thereby creating the viable subpopulation of said given cell population.

13. The system of claim 1,
wherein the treatment cell has a shape such that no meniscus is formed that can distort the electric field when the treatment cell is completely filled with a pulsing medium, wherein said treatment cell includes a flow path having an inlet and an outlet and is constructed and arrange to provide a treatment volume for continuous flow treatment of a cell suspension therewithin.

14. The system of claim 1,
wherein the generating mechanism is configured to generate a bipolar electric field.

15. A system as in claim 1, further comprising:
a cooling system comprising a circulation system for a fluid configured to circulate cooling fluid in thermal communication with said electrode; and
a control system able to determine temperature of the suspension and able to control the temperature of the suspension by controlling the cooling system.

16. A system as in claim 15, wherein the control system further comprises one or more temperature probes and/or thermocouples.

17. A system as in claim 1, wherein the electrode is shaped to generate electric field strengths outside of a main electric field treatment region that do not exceed the electric field strengths in the main electric field treatment region.

18. A system as in claim 1, wherein the treatment cell is a flow-through treatment cell having an inlet and an outlet.

19. A system as in claim 1, wherein the generating mechanism is able to generate electric field pulses at a pulse frequency of less than 10 kHz.

20. A system as in claim 1 wherein the generating mechanism is able to generate an electric field pulse having a substantially rectangular pulse shape.

* * * * *